(12) United States Patent
Cheng et al.

(10) Patent No.: US 7,956,069 B2
(45) Date of Patent: Jun. 7, 2011

(54) COMPOUNDS

(75) Inventors: Yun-Xing Cheng, St. Laurent (CA); Mehrnaz Pourashraf, St. Laurent (CA); Miroslaw Tomaszewski, St. Laurent (CA)

(73) Assignee: AstraZeneca AB (SE)

( * ) Notice: Subject to any disclaimer, the term of this patent is extended or adjusted under 35 U.S.C. 154(b) by 923 days.

(21) Appl. No.: 11/760,011

(22) Filed: Jun. 8, 2007

(65) Prior Publication Data

US 2007/0287695 A1 Dec. 13, 2007

Related U.S. Application Data

(60) Provisional application No. 60/812,209, filed on Jun. 9, 2006.

(51) Int. Cl.
A61K 31/454 (2006.01)
C07D 403/14 (2006.01)
(52) U.S. Cl. .......... 514/322; 514/210.21; 514/316; 546/187; 546/199
(58) Field of Classification Search .......... 514/210.21, 514/316, 322; 546/187, 199
See application file for complete search history.

(56) References Cited

U.S. PATENT DOCUMENTS

| | | | |
|---|---|---|---|
| 5,665,719 A | 9/1997 | Bock et al. | |
| 5,756,497 A | 5/1998 | Bell et al. | |
| 5,756,508 A | 5/1998 | Thompson et al. | |
| 6,258,811 B1 | 7/2001 | Yamauchi et al. | |
| 6,812,226 B2 | 11/2004 | Baxter et al. | |
| 7,273,857 B2 * | 9/2007 | Kelly et al. | 514/183 |
| 2007/0259888 A1 | 11/2007 | Cheng et al. | |
| 2009/0076078 A1 * | 3/2009 | Cheng et al. | 514/316 |
| 2009/0221567 A1 | 9/2009 | Cheng et al. | |
| 2009/0221642 A1 | 9/2009 | Jin et al. | |
| 2009/0275574 A1 | 11/2009 | Cheng et al. | |
| 2010/0173935 A1 | 7/2010 | Cheng et al. | |

FOREIGN PATENT DOCUMENTS

| | | |
|---|---|---|
| EP | 0029707 B1 | 2/1984 |
| EP | 0608858 A1 | 1/1994 |
| EP | 1386920 A1 | 2/2004 |
| EP | 1221443 B1 | 9/2004 |
| EP | 1790637 A1 | 5/2007 |
| JP | 2000323278 | 11/2000 |
| JP | 2002302675 | 10/2002 |
| WO | 9502405 A1 | 1/1995 |
| WO | 9613262 A1 | 5/1996 |
| WO | 9811128 A1 | 3/1998 |
| WO | 9929686 A1 | 6/1999 |
| WO | 9932481 A1 | 7/1999 |
| WO | 0144213 A1 | 6/2001 |
| WO | 0214315 A2 | 2/2002 |
| WO | 02085357 A1 | 10/2002 |
| WO | 02085361 A1 | 10/2002 |
| WO | 03037890 A2 | 5/2003 |
| WO | 03088967 A1 | 10/2003 |
| WO | 03105781 A2 | 12/2003 |
| WO | 2004069828 A1 | 8/2004 |
| WO | 2004089942 A2 | 10/2004 |
| WO | 2004099159 A1 | 11/2004 |
| WO | 2005060711 A2 | 7/2005 |
| WO | 2005060947 A2 | 7/2005 |
| WO | 2005117883 A1 | 12/2005 |
| WO | 2006037052 A2 | 4/2006 |
| WO | 2006038594 A1 | 4/2006 |
| WO | 2006130469 A1 | 12/2006 |

OTHER PUBLICATIONS

English abstract for JP 2000-323278.
English abstract for JP 2002-302675.
English abstract for EP 0608858.
English abstract for WO 9811128.
English abstract for WO 2004069828.
English abstract for WO 2006038594.
International Search Report issued for PCT/SE2007/000554 on Sep. 20, 2007.
Cecil Textbook of Medicine, 20th Edition, vol. 2, 1996, pp. 1992-1996.
PubMed Abstract 12621313; J. Cereb Blood Flow Metab., Mar. 2003, 23(3), 381-4.
PubMed Abstract 12910626; J. Soc. Biol., 2003, 197(2), 113-22.
PubMed Abstract 14511112; J. Neurochem, Oct. 2003, 87(2), 344-52.
PubMed Abstract 14561158; Curr. Drug Targets Inflamm Allergy, Sep. 2003, 2(3), 232-41.
Ferrari et al., "Extracellular ATP Triggers IL-1 Release by Activating the Purinergic P2Z Receptor of Human Macrophages," Journal of Immunology, vol. 159(3), 1997, pp. 1451-1458.
Ferrari et al., "Purinergic Modulation of Interleukin-1 Release from Microglial Cells Stimulated with Bacterial Endotoxin," J. Exp. Med., vol. 185(3), 1997, pp. 579-582.

(Continued)

*Primary Examiner* — Celia Chang
(74) *Attorney, Agent, or Firm* — Connolly Bove Lodge & Hutz, LLP

(57) ABSTRACT

Compounds of Formulae I, or pharmaceutically acceptable salts thereof:

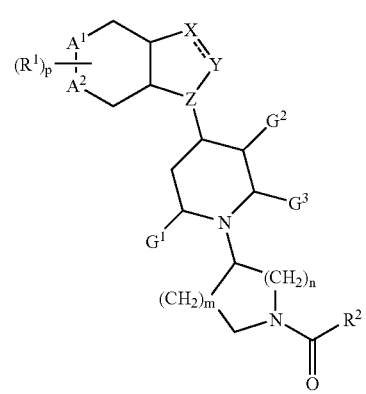

I wherein $A^1$, $A^2$, $G^1$, $G^2$, $G^3$, $R^1$, $R^2$, X, Y, Z, m, n and p are as defined in the specification as well as salts and pharmaceutical compositions including the compounds are prepared. They are useful in therapy, in particular in the management of pain.

2 Claims, No Drawings

OTHER PUBLICATIONS

Henderson et al., "Inhibition of Interleukin-1-Induced Synovitis and Articular Cartilage Proteoglycan Loss in the Rabbit Knee by Recombinant Human Interleukin-1 Receptor Antagonist," Cytokine, vol. 3(3), 1991, pp. 246-249.

Kadota et al., "Significance of IL-1 and IL-1 Receptor Antagonist (IL-1Ra) in Bronchoalveolar Lavage Fluid (BALF) in Patients with Diffuse Panbronchiolitis (DPB)," Clin. Exp. Immunol., vol. 103, 1996, pp. 461-466.

Otterness et al., "Possible Role of IL-1 in Arthritis: Effects of Prostaglandins in the Regulation of IL-1 Synthesis and Actions," Joint Destruction in Arthritis and Osteoarthritis, Agents and Actions Supplements, vol. 39, 1993, pp. 109-120.

Sakito et al., "Interleukin 1, Tumor Necrosis Factor Alpha, and Interleukin 8 in Bronchoalveolar Lavage Fluid of Patients with Diffuse Panbronchiolitis: A Potential Mechanism of Macrolide Therapy," Respiration, vol. 63, 1996, pp. 42-48.

Yu et al., "Inhibition of IL-1 Release from Human Monocytes and Suppression of Streptococcal Cell Wall and Adjuvant-induced Arthritis in Rats by an Extract of Tripterygium Wilfordii Hook," General Pharmacology, vol. 25(6), 1994, pp. 1115-1122.

* cited by examiner

COMPOUNDS

The present application claims the benefit of U.S. Provisional Application 60/812,209, filed Jun. 9, 2006 under 35 U.S.C. §119(e), the entirety of which is incorporated herein by reference.

BACKGROUND OF THE INVENTION

1. Field of the Invention

The present invention relates to agonists of muscarinic receptors. The present invention also provides compositions comprising such agonists, and methods therewith for treating muscarinic receptor mediated diseases. Particularly, the present invention is related to compounds that may be effective in treating pain, Alzheimer's disease, and/or schizophrenia.

2. Discussion of Relevant Technology

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs) and show a remarkably high degree of homology across species and receptor subtype. These M1-M5 muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors-Characterization, Coupling, and Function," Pharmacol. Ther., 58, pp. 319-379 (1993); Caulfield, M. P. et al., International Union of Pharmacology. XVII. Classification of Muscarinic Acetylcholine Receptors," Pharmacol. Rev., 50, pp. 279-290 (1998).

The Muscarinic family of receptors is the target of a large number of pharmacological agents used for various diseases, including leading drugs for COPD, asthma, urinary incontinence, glaucoma, schizophrenia, Alzheimer's (AchE inhibitors), and Pain.

For example, direct acting muscarinic receptor agonists have been shown to be antinociceptive in a variety of animal models of acute pain (Bartolini A., Ghelardini C., Fantetti L., Malcangio M., Malmberg-Aiello P., Giotti A. Role of muscarinic receptor subtypes in central antinociception. Br. J. Pharmacol. 105:77-82, 1992; Capone F., Aloisi A. M., Carli G., Sacerdote P., Pavone F. Oxotremorine-induced modifications of the behavioral and neuroendocrine responses to formalin pain in male rats. Brain Res. 830:292-300, 1999).

A few studies have examined the role of muscarinic receptor activation in chronic or neuropathic pain states. In these studies, the direct and indirect elevation of cholinergic tone was shown to ameliorate tactile allodynia after intrathecal administration in a spinal ligation model of neuropathic pain in rats and these effects again were reversed by muscarinic antagonists (Hwang J.-H., Hwang K.-S., Leem J.-K., Park P.-H., Han S.-M., Lee D.-M. The antiallodynic effects of intrathecal cholinesterase inhibitors in a rat model of neuropathic pain. Anesthesiology 90:492-494, 1999; Lee E. J., Sim J. Y. Park J. Y., Hwang J. H., Park P. H., Han S. M. Intrathecal carbachol and clonidine produce a synergistic antiallodynic effect in rats with a nerve ligation injury. Can J Anaesth 49:178-84, 2002). Thus, direct or indirect activation of muscarinic receptors has been shown to elicit both acute analgesic activity and to ameliorate neuropathic pain. Muscarinic agonists and ACHE-Is are not widely used clinically owing to their propensity to induced a plethora of adverse events when administered to humans. The undesirable side-effects include excessive salivation and sweating, enhanced gastrointestinal motility, and bradycardia among other adverse events. These side-effects are associated with the ubiquitous expression of the muscarinic family of receptors throughout the body.

DESCRIPTION OF THE EMBODIMENTS

To date, five subtypes of muscarinic receptors (M1-M5) have been cloned and sequenced from a variety of species, with differential distributions in the body.

Therefore, it was desirable to provide molecules would permit selective modulation, for example, of muscarinic receptors controlling central nervous function without also activating muscarinic receptors controlling cardiac, gastrointestinal or glandular functions.

There is also a need for methods for treating muscarinic receptor-mediated diseases.

There is also a need for modulators of muscarinic receptors that are selective as to subtypes M1-M5.

The term "$C_{m-n}$" or "$C_{m-n}$ group" refers to any group having m to n carbon atoms.

The term "alkyl" refers to a saturated monovalent straight or branched chain hydrocarbon radical comprising 1 to about 12 carbon atoms. Illustrative examples of alkyls include, but are not limited to, $C_{1-6}$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl can be unsubstituted or substituted with one or two suitable substituents.

The term "alkenyl" refers to a monovalent straight or branched chain hydrocarbon radical having at least one carbon-carbon double bond and comprising at least 2 up to about 12 carbon atoms. The double bond of an alkenyl can be unconjugated or conjugated to another unsaturated group. Suitable alkenyl groups include, but are not limited to $C_{2-6}$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl can be unsubstituted or substituted with one or two suitable substituents.

The term "cycloalkyl" refers to a saturated monovalent ring-containing hydrocarbon radical comprising at least 3 up to about 12 carbon atoms. Examples of cycloalkyls include, but are not limited to, $C_{3-7}$cycloalkyl groups, such as cyclopropyl, cyclobutyl, cyclopentyl, cyclohexyl, and cycloheptyl, and saturated cyclic and bicyclic terpenes. A cycloalkyl can be unsubstituted or substituted by one or two suitable substituents. Preferably, the cycloalkyl is a monocyclic ring or bicyclic ring.

The term "cycloalkenyl" refers to a monovalent ring-containing hydrocarbon radical having at least one carbon-carbon double bond and comprising at least 3 up to about 12 carbon atoms.

The term "aryl" refers to a monovalent hydrocarbon radical having one or more polyunsaturated carbon rings having aromatic character, (e.g., 4n+2 delocalized electrons) and comprising 5 up to about 14 carbon atoms.

The term "heterocycle" refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroaromatic" refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" refers to a radical derived from a heterocycle by removing one or more hydrogens therefrom.

The term "heterocyclyl" refers a monovalent radical derived from a heterocycle by removing one hydrogen therefrom.

The term "heterocyclylene" refers to a divalent radical derived from a heterocycle by removing two hydrogens therefrom, which serves to links two structures together.

The term "heteroaryl" refers to a heterocyclyl having aromatic character.

The term "heterocylcoalkyl" refers to a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $C_{3-6}$heterocycloalkyl.

The term "heteroarylene" refers to a heterocyclylene having aromatic character.

The term "heterocycloalkylene" refers to a heterocyclylene that does not have aromatic character.

The term "six-membered" refers to a group having a ring that contains six ring atoms.

The term "five-membered" refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4- benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

Halogen includes fluorine, chlorine, bromine and iodine.

"RT" or "rt" means room temperature.

In one aspect, an embodiment of the invention provides a compound of Formula I, a pharmaceutically acceptable salt thereof, diastereomer, enantiomer, or mixture thereof:

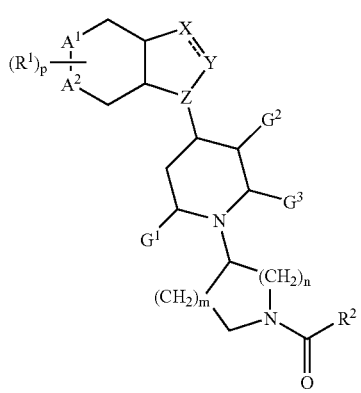

I wherein $A^1$ and $A^2$ are independently selected from —$CH_2$—, —CH(R)—, —N(R)—, and —O—;

$G^1$, $G^2$ and $G^3$ are independently selected from hydrogen, halogen, $C_{1-6}$alkyl, $C_{1-6}$alkoxy, hydroxy-$C_{1-6}$alkyl, —$CH_2$—OR, halogenated $C_{1-6}$alkyl, —$CONR^2$; or any two of $G^1$, $G^2$ and $G^3$ are linked together to form a $C_{1-4}$alkylene bridge and the other one of $G^1$, $G^2$ and $G^3$ is as defined above;

$R^1$ is independently selected from hydrogen, halogen, $C_{1-6}$alkyl, $C_{2-6}$alkenyl, —CN, —C(=O)—OR, —C(=O)—$NR_2$, hydroxy, and $C_{1-6}$alkoxy;

$R^2$ is selected from hydrogen, $C_{1-6}$alkyl, $C_{2-6}$alkenyl, $C_{1-6}$alkoxy, $C_{1-6}$alkylamino, di-$C_{1-6}$alkylamino, $C_{6-10}$aryl, $C_{6-10}$aryloxy, $C_{2-9}$heteroaryl, $C_{2-9}$heteroaryloxy, $C_{3-5}$heterocycloalkyloxy, $C_{3-5}$heterocycloalkyl, $C_{6-10}$aryl-$C_{1-3}$alkoxy, $C_{6-10}$aryl-$C_{1-3}$alkyl, $C_{2-9}$heteroaryl-$C_{1-3}$alkoxy, $C_{2-9}$heteroaryl-$C_{1-3}$alkyl, $C_{3-5}$heterocycloalkyl-$C_{1-3}$alkoxy, $C_{3-5}$heterocycloalkyl-$C_{1-3}$alkyl, $C_{3-6}$cycloalkyl, $C_{3-6}$cycloalkyloxy, and $C_{3-6}$cycloalkyl-$C_{1-3}$alkyl, $C_{3-6}$cycloalkyl-$C_{1-3}$alkoxy, wherein said $C_{1-6}$alkyl, $C_{2-6}$alkenyl, $C_{1-6}$alkyl-carbonyl, $C_{1-6}$alkylaminocarbonyl, $C_{6-10}$aryl, $C_{2-9}$heteroaryl, $C_{3-5}$heterocycloalkyl, $C_{6-10}$aryl-$C_{1-3}$alkyl, $C_{2-9}$heteroaryl-$C_{1-3}$alkyl, $C_{3-5}$heterocycloalkyl-$C_{1-3}$alkyl, $C_{3-6}$cycloalkyl, and $C_{3-6}$cycloalkyl-$C_{1-3}$alkyl are optionally substituted with one or more group selected from —CN, —SR, —OR, —O($CH_2$)$_p$—OR, R, —C(=O)—R, —$CO_2$R, —$SO_2$R, —$SO_2NR_2$, halogen, —$NO_2$, —$NR_2$, —($CH_2$)$_p NR_2$, and —C(=O)—$NR_2$;

p is 1, 2, 3 or 4; m is 0, 1, or 2; n is 1, or 2;

X, Y and Z are independently selected from C(=O), NH, N—R, N, C, $CH_2$, and CH, wherein at least one of X, Y and Z is selected from NH, N—R and N; wherein at most one of X, Y and Z is C(=O); and wherein Z is not C(=O); and each R is independently hydrogen, $C_{1-6}$alkyl, $C_{2-6}$alkenyl or halogenated $C_{1-6}$alkyl.

In another embodiment, $A^1$ and $A^2$ are independently selected from —$CH_2$— and —N(R)—, wherein each R is independently hydrogen or $C_{1-6}$alkyl.

In another embodiment, one of $A^1$ and $A^2$ is —$CH_2$—; and the other one of $A^1$ and $A^2$ is —N(R)—.

In a further embodiment, $A^1$ and $A^2$ are —$CH_2$—.

In another embodiment, $G^1$, $G^2$ and $G^3$ are independently selected from hydrogen, halogen, $C_{1-6}$alkyl, $C_{1-6}$alkoxy, hydroxy-$C_{1-6}$alkyl, —$CH_2$—OR, halogenated $C_{1-6}$alkyl, —$CONR^2$; wherein each R is independently hydrogen or $C_{1-6}$alkyl.

Particularly, $G^1$, $G^2$ and $G^3$ are independently selected from hydrogen, fluoro, $C_{1-6}$alkyl, $C_{1-6}$alkoxy, hydroxy-methyl, —$CH_2$—OR, trifluoromethyl, —C(=O)$NR_2$; wherein each R is independently hydrogen or $C_{1-3}$alkyl.

In a further embodiment, any two of $G^1$, $G^2$ and $G^3$ are linked together to form a $C_{1-4}$alkylene bridge and the other one of $G^1$, $G^2$ and $G^3$ is selected from hydrogen, halogen, $C_{1-6}$alkyl, $C_{1-6}$alkoxy, hydroxy-$C_{1-6}$alkyl, —$CH_2$—OR, halogenated $C_{1-6}$alkyl, —C(=O)$NR_2$; wherein each R is independently hydrogen or $C_{1-6}$alkyl.

Particularly, $G^1$ and $G^3$ are linked together to form a $C_{2-4}$alkylene bridge; and $G^2$ is selected from hydrogen, fluoro, $C_{1-6}$alkyl, $C_{1-6}$alkoxy, hydroxy-methyl, —$CH_2$—OR, trifluoromethyl, —C(=O)$NR_2$; wherein each R is independently hydrogen or $C_{1-3}$alkyl.

In another embodiment, $G^1$ and $G^2$ are linked together to form a $C_{1-3}$alkylene bridge; and $G^3$ is selected from hydrogen, fluoro, $C_{1-6}$alkyl, $C_{1-6}$alkoxy, hydroxy-methyl, —$CH_2$—OR, trifluoromethyl, —C(=O)$NR_2$; wherein each R is independently hydrogen or $C_{1-3}$alkyl.

In a further particular embodiment, $R^2$ is selected from hydrogen, $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{1-6}$alkoxy, $C_{1-6}$alkylamino, di-$C_{1-6}$alkylamino and benzyloxy, wherein said $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{1-6}$alkoxy, $C_{1-6}$alkylamino, di-$C_{1-6}$alkylamino and benzyloxy are optionally substituted by one or more groups selected from amino, halogen, hydroxy, $C_{1-6}$alkoxy and —CN. In an even further embodiment, $R^2$ is selected from hydrogen, $C_{1-4}$alkyl, $C_{1-4}$alkoxy, $C_{1-4}$alkylamino, di-$C_{1-4}$alkylamino, $C_{3-6}$cycloalkyl, pyrrolidinyl, piperidinyl, azetidinyl and benzyloxy.

In yet another embodiment, $R^2$ is selected from methyl, ethyl, n-propyl, isopropyl, 2-methyl-1-propyl, benzyl, phenyl, thiophenyl, methoxy, ethoxy, benzyloxy, t-butoxy, cyclopentyl, cyclohexyl, pyrrolidinyl, piperidinyl, methylamino, and ethylamino.

In another embodiment, $R^1$ is selected from hydrogen, halogen, methyl, ethyl, —CN, —C(=O)—$NH_2$, —$CO_2CH_3$, —$CO_2H$, hydroxy and methoxy.

In a further embodiment, $R^1$ is hydrogen.

In another embodiment, p is 1.

In another embodiment, m, n is 1.

In a further embodiment, m is 1 and n is 2.

In another embodiment, Z is selected from N, C and CH.

In a further embodiment, Y is selected from N and C(=O).

In an even further embodiment, X is selected from NH and N—R, wherein R is hydrogen or $C_{1-3}$alkyl.

In another embodiment, the invention provides a compound of formula II, a pharmaceutically acceptable salt thereof, diastereomer, enantiomer, or mixture thereof:

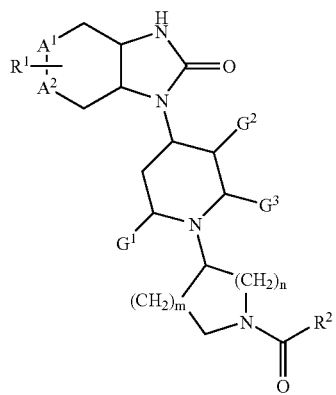

II

Wherein $A^1$ and $A^2$ are independently selected from —$CH_2$—, —CH(R)—, —N(R)—, and —O—;

$G^1$, $G^2$ and $G^3$ are independently selected from hydrogen, halogen, $C_{1-6}$alkyl, $C_{1-6}$alkoxy, hydroxy-$C_{1-6}$alkyl, —$CH_2$—OR, halogenated $C_{1-6}$alkyl, —C(=O)$NR_2$; or any two of $G^1$, $G^2$ and $G^3$ are linked together to form a $C_{1-4}$alkylene bridge and the other one of $G^1$, $G^2$ and $G^3$ is as defined above;

$R^1$ is independently selected from hydrogen, halogen, $C_{1-6}$alkyl, $C_{2-6}$alkenyl, —CN, —C(=O)—OR, —C(=O)—$NR_2$, hydroxy, and $C_{1-6}$alkoxy;

$R^2$ is selected from hydrogen, $C_{1-6}$alkyl, $C_{2-6}$alkenyl, $C_{1-6}$alkoxy, $C_{1-6}$alkylamino, di-$C_{1-6}$alkylamino, $C_{6-10}$aryl, $C_{6-10}$aryloxy, $C_{2-9}$heteroaryl, $C_{2-9}$heteroaryloxy, $C_{3-5}$heterocycloalkyloxy, $C_{3-5}$heterocycloalkyl, $C_{6-10}$aryl-$C_{1-3}$alkoxy, $C_{6-10}$aryl-$C_{1-3}$alkyl, $C_{2-9}$heteroaryl-$C_{1-3}$alkoxy, $C_{2-9}$heteroaryl-$C_{1-3}$alkyl, $C_{3-5}$heterocycloalkyl-$C_{1-3}$alkoxy, $C_{3-5}$heterocycloalkyl-$C_{1-3}$alkyl, $C_{3-6}$cycloalkyl, $C_{3-6}$cycloalkyloxy, and $C_{3-6}$cycloalkyl-$C_{1-3}$alkyl, $C_{3-6}$cycloalkyl-$C_{1-3}$alkoxy, wherein said $C_{1-6}$alkyl, $C_{2-6}$alkenyl, $C_{1-6}$alkyl-carbonyl, $C_{1-6}$alkylaminocarbonyl, $C_{6-10}$aryl, $C_{2-9}$heteroaryl, $C_{3-5}$heterocycloalkyl, $C_{6-10}$aryl-$C_{1-3}$alkyl, $C_{2-9}$heteroaryl-$C_{1-3}$alkyl, $C_{3-5}$heterocycloalkyl-$C_{1-3}$alkyl, $C_{3-6}$cycloalkyl, and $C_{3-6}$cycloalkyl-$C_{1-3}$alkyl are optionally substituted with one or more group selected from —CN, —SR, —OR, —O$(CH_2)_p$—OR, R, —C(=O)—R, —$CO_2$R, —$SO_2$R, —$SO_2NR_2$, halogen, —$NO_2$, —$NR_2$, —$(CH_2)_p NR_2$, and —C(=O)—$NR_2$;

m is 0, 1, or 2; n is 1, 2; and each R is independently hydrogen, $C_{1-6}$alkyl, $C_{2-6}$alkenyl or halogenated $C_{1-6}$alkyl.

In another embodiment, $A^1$ and $A^2$ are independently selected from —$CH_2$— and —N(R)—, wherein each R is independently hydrogen or $C_{1-6}$alkyl.

In another embodiment, one of $A^1$ and $A^2$ is —$CH_2$—; and the other one of $A^1$ and $A^2$ is —N(R)—.

In a further embodiment, $A^1$ and $A^2$ are —$CH_2$—.

In another embodiment, $G^1$, $G^2$ and $G^3$ are independently selected from hydrogen, halogen, $C_{1-6}$alkyl, $C_{1-6}$alkoxy, hydroxy-$C_{1-6}$alkyl, —$CH_2$—OR, halogenated $C_{1-6}$alkyl, —$CONR^2$; wherein each R is independently hydrogen or $C_{1-6}$alkyl.

Particularly, $G^1$, $G^2$ and $G^3$ are independently selected from hydrogen, fluoro, $C_{1-6}$alkyl, $C_{1-6}$alkoxy, hydroxy-methyl, —$CH_2$—OR, trifluoromethyl, —C(=O)$NR_2$; wherein each R is independently hydrogen or $C_{1-3}$alkyl.

In a further embodiment, any two of $G^1$, $G^2$ and $G^3$ are linked together to form a $C_{1-4}$alkylene bridge and the other one of $G^1$, $G^2$ and $G^3$ is selected from hydrogen, halogen, $C_{1-6}$alkyl, $C_{1-6}$alkoxy, hydroxy-$C_{1-6}$alkyl, —$CH_2$—OR, halogenated $C_{1-6}$alkyl, —C(=O)$NR_2$; wherein each R is independently hydrogen or $C_{1-6}$alkyl.

Particularly, $G^1$ and $G^3$ are linked together to form a $C_{2-4}$alkylene bridge; and $G^2$ is selected from hydrogen, fluoro, $C_{1-6}$alkyl, $C_{1-6}$alkoxy, hydroxy-methyl, —$CH_2$—OR, trifluoromethyl, —$CONR^2$; wherein each R is independently hydrogen or $C_{1-3}$alkyl.

In another embodiment, $G^1$ and $G^2$ are linked together to form a $C_{1-3}$alkylene bridge; and $G^3$ is selected from hydrogen, fluoro, $C_{1-6}$alkyl, $C_{1-6}$alkoxy, hydroxy-methyl, —$CH_2$—OR, trifluoromethyl, —C(=O)$NR_2$; wherein each R is independently hydrogen or $C_{1-3}$alkyl.

In a further particular embodiment, $R^2$ of formula II is selected from hydrogen, $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{1-6}$alkoxy, $C_{1-6}$alkylamino, di-$C_{1-6}$alkylamino and benzyloxy, wherein said $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{1-6}$alkoxy, $C_{1-6}$alkylamino, di-$C_{1-6}$alkylamino and benzyloxy are optionally substituted by one or more groups selected from amino, halogen, hydroxy, $C_{1-6}$alkoxy and —CN.

In an even further embodiment, $R^2$ of formula II is selected from hydrogen, $C_{1-4}$alkyl, $C_{1-4}$alkoxy, $C_{1-4}$alkylamino, di-$C_{1-4}$alkylamino, $C_{3-6}$cycloalkyl, pyrrolidinyl, piperidinyl, azetidinyl and benzyloxy.

In yet another embodiment, $R^2$ of formula II is selected from methyl, ethyl, n-propyl, isopropyl, 2-methyl-1-propyl, benzyl, phenyl, thiophenyl, methoxy, ethoxy, benzyloxy, t-butoxy, cyclopentyl, cyclohexyl, pyrrolidinyl, piperidinyl, methylamino, and ethylamino.

In another embodiment, $R^1$ of formula II is selected from hydrogen, halogen, methyl, ethyl, —CN, —C(=O)—$NH_2$, —$CO_2CH_3$, —$CO_2H$, hydroxy and methoxy.

In an even further embodiment, $R^1$ is hydrogen.

In another embodiment, m, n is 1.

In a further embodiment, m is 1 and n is 2.

In another embodiment, the present invention provides a compound of formula IA, a pharmaceutically acceptable salt thereof, diastereomer, enantiomer, or mixture thereof:

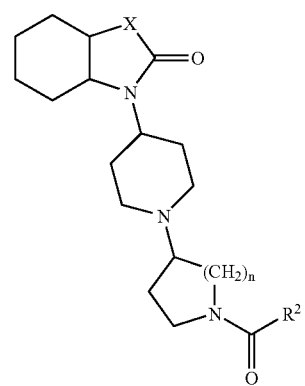

IA wherein $R^2$ is selected from hydrogen, $C_{1-6}$alkyl, $C_{2-6}$alkenyl, $C_{1-6}$alkoxy, $C_{1-6}$alkylamino, di-$C_{1-6}$alkylamino, $C_{6-10}$aryl, $C_{6-10}$aryloxy, $C_{2-9}$heteroaryl, $C_{2-9}$heteroaryloxy, $C_{3-5}$heterocycloalkyloxy, $C_{3-5}$heterocycloalkyl, $C_{6-10}$aryl-$C_{1-3}$alkoxy, $C_{6-10}$aryl-$C_{1-3}$alkyl, $C_{2-9}$heteroaryl-$C_{1-3}$alkoxy, $C_{2-9}$heteroaryl-$C_{1-3}$alkyl, $C_{3-5}$heterocycloalkyl-$C_{1-3}$alkoxy, $C_{3-5}$heterocycloalkyl-$C_{1-3}$alkyl, $C_{3-6}$cycloalkyl, $C_{3-6}$cycloalkyloxy, and $C_{3-6}$cycloalkyl-$C_{1-3}$alkyl, $C_{3-6}$cycloalkyl-$C_{1-3}$alkoxy, wherein said $C_{1-6}$alkyl, $C_{2-6}$alkenyl, $C_{1-6}$alkyl-carbonyl, $C_{1-6}$alkylaminocarbonyl, $C_{6-10}$aryl, $C_{2-9}$heteroaryl, $C_{3-5}$heterocycloalkyl, $C_{6-10}$aryl-$C_{1-3}$alkyl, $C_{2-9}$heteroaryl-$C_{1-3}$alkyl, $C_{3-5}$heterocycloalkyl-$C_{1-3}$alkyl, $C_{3-6}$cycloalkyl, and $C_{3-6}$cycloalkyl-$C_{1-3}$alkyl are optionally substituted with one or more group selected from phenyl, $C_{3-6}$cycloalkyl, $C_{2-5}$heterocycloalkyl, $C_{2-5}$heteroaryl, —CN, —SR, —OR, —O(CH$_2$)$_p$—OR, R, —C(=O)—R, —CO$_2$R, —SO$_2$R, —SO$_2$NR$_2$, halogen, —NO$_2$, —NR$_2$, —(CH$_2$)$_p$NR$_2$, and —C(=O)—NR$_2$;

p is 1, 2, 3 or 4; n is 1, 2;

X, is independently selected from NH, N—R, CH$_2$ CHR, and CRR'; and each R, R' is independently hydrogen, $C_{1-6}$alkyl, $C_{2-6}$alkenyl or halogenated $C_{1-6}$alkyl.

In a particular embodiment, $R^2$ of formula IA is selected from hydrogen, $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{2-5}$heterocycloalkyl-$C_{1-3}$alkyl, phenyl, benzyl, $C_{2-9}$heteroaryl, $C_{1-6}$alkoxy, $C_{1-6}$alkylamino, di-$C_{1-6}$alkylamino and benzyloxy, wherein said $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{2-5}$heterocycloalkyl-$C_{1-3}$alkyl, phenyl, benzyl, $C_{2-9}$heteroaryl, $C_{1-6}$alkoxy, $C_{1-6}$alkylamino, di-$C_{1-6}$alkylamino and benzyloxy are optionally substituted by one or more groups selected from amino, halogen, phenyl, morpholinyl, $C_{3-6}$cycloalkyl, $C_{1-6}$alkyl, hydroxy, $C_{1-6}$alkoxy and —CN.

In another particular embodiment, $R^2$ of formula IA is selected from hydrogen, $C_{1-6}$alkyl, $C_{1-4}$alkoxy, $C_{1-4}$alkylamino, di-$C_{1-4}$alkylamino, $C_{3-6}$cycloalkyl, pyrrolidinyl, thienyl, furyl, quinolinyl, dihydrobenzofuranyl, pyrrolyl, 2-oxopyrrolidinyl-$C_{1-3}$alkyl, phenyl, benzyl, piperidinyl, azetidinyl and benzyloxy, wherein said $C_{1-6}$alkyl, $C_{1-4}$alkoxy, $C_{1-4}$alkylamino, di-$C_{1-4}$alkylamino, $C_{3-6}$cycloalkyl, pyrrolidinyl, furyl, quinolinyl, dihydrobenzofuranyl, pyrrolyl, 2-oxopyrrolidinyl-$C_{1-3}$alkyl, phenyl, benzyl, piperidinyl, azetidinyl and benzyloxy are optionally substituted by one or more groups selected from amino, halogen, phenyl, morpholinyl, $C_{3-6}$cycloalkyl, $C_{1-6}$alkyl, hydroxy, $C_{1-6}$alkoxy and —CN.

In a further embodiment, $R^2$ of formula IA is selected from methyl, ethyl, n-propyl, isopropyl, n-butyl, isobutyl, tertbutyl, 4-heptyl, 2-methyl-1-propyl, benzyl, phenyl, thienyl, furyl, quinolinyl, dihydrobenzofuranyl, pyrrolyl, 2-oxopyrrolidinyl-ethyl, methoxy, ethoxy, isopropoxy, propoxy, benzyloxy, t-butoxy, isopropenoxy, isobutoxy, $C_{3-6}$cycloalkoxy, cyclopropyl, cyclobutyl, cyclopentyl, cyclohexyl, pyrrolidinyl, piperidinyl, azetidinyl, methylamino, and ethylamino, which are optionally substituted by one or more groups selected from amino, halogen, phenyl, morpholinyl, CF$_3$, —C(=O)$C_{1-6}$alkyl, $C_{3-6}$cycloalkyl, $C_{1-6}$alkyl, hydroxy, $C_{1-6}$alkoxy and —CN.

In a further embodiment, n of formula IA is 1.

In another embodiment, n of formula IA is 2.

In another embodiment, X of formula IA is selected from NH and N—R, wherein R is hydrogen, $C_{2-3}$alkenyl or $C_{1-3}$alkyl.

In an even further embodiment, the present invention provides a compound of formula IIA, a pharmaceutically acceptable salt thereof, diastereomer, enantiomer, or mixture thereof:

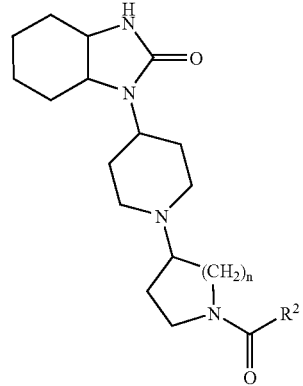

IIA wherein $R^2$ is selected from hydrogen, $C_{1-6}$alkyl, $C_{2-6}$alkenyl, $C_{1-6}$alkoxy, $C_{1-6}$alkylamino, di-$C_{1-6}$alkylamino, $C_{6-10}$aryl, $C_{6-10}$aryloxy, $C_{2-9}$heteroaryl, $C_{2-9}$heteroaryloxy, $C_{3-5}$heterocycloalkyloxy, $C_{3-5}$heterocycloalkyl, $C_{6-10}$aryl-$C_{1-3}$alkoxy, $C_{6-10}$aryl-$C_{1-3}$alkyl, $C_{2-9}$heteroaryl-$C_{1-3}$alkoxy, $C_{2-9}$heteroaryl-$C_{1-3}$alkyl, $C_{3-5}$heterocycloalkyl-$C_{1-3}$alkoxy, $C_{3-5}$heterocycloalkyl-$C_{1-3}$alkyl, $C_{3-6}$cycloalkyl, $C_{3-6}$cycloalkyloxy, and $C_{3-6}$cycloalkyl-$C_{1-3}$alkyl, $C_{3-6}$cycloalkyl-$C_{1-3}$alkoxy, wherein said $C_{1-6}$alkyl, $C_{2-6}$alkenyl, $C_{1-6}$alkyl-carbonyl, $C_{1-6}$alkylaminocarbonyl, $C_{6-10}$aryl, $C_{2-9}$heteroaryl, $C_{3-5}$heterocycloalkyl, $C_{6-10}$aryl-$C_{1-3}$alkyl, $C_{2-9}$heteroaryl-$C_{1-3}$alkyl, $C_{3-5}$heterocycloalkyl-$C_{1-3}$alkyl, $C_{3-6}$cycloalkyl, and $C_{3-6}$cycloalkyl-$C_{1-3}$alkyl are optionally substituted with one or more group selected from phenyl, $C_{3-6}$cycloalkyl, $C_{2-5}$heterocycloalkyl, $C_{2-5}$heteroaryl, —CN, —SR, —OR, —O(CH$_2$)$_p$—OR, R, —C(=O)—R, —CO$_2$R, —SO$_2$R, —SO$_2$NR$_2$, halogen, —NO$_2$, —NR$_2$, —(CH$_2$)$_p$NR$_2$, and —C(=O)—NR$_2$;

p is 1, 2, 3 or 4; n is 1, 2;

and each R is independently hydrogen, $C_{1-6}$alkyl, $C_{2-6}$alkenyl or halogenated $C_{1-6}$alkyl.

In a particular embodiment, $R^2$ of formula IIA is selected from hydrogen, $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{2-5}$heterocycloalkyl-$C_{1-3}$alkyl, phenyl, benzyl, $C_{2-9}$heteroaryl, $C_{1-6}$alkoxy, $C_{1-6}$alkylamino, di-$C_{1-6}$alkylamino and benzyloxy, wherein said $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{2-5}$heterocycloalkyl-$C_{1-3}$alkyl, phenyl, benzyl, $C_{2-9}$heteroaryl, $C_{1-6}$alkoxy, $C_{1-6}$alkylamino, di-$C_{1-6}$alkylamino and benzyloxy are optionally substituted by one or more groups selected from amino, halogen, phenyl, morpholinyl, $C_{3-6}$cycloalkyl, $C_{1-6}$alkyl, hydroxy, $C_{1-6}$alkoxy and —CN.

In a particular embodiment, $R^2$ of formula IIA is selected from hydrogen, $C_{1-6}$alkyl, $C_{1-4}$alkoxy, $C_{1-4}$alkylamino, di-$C_{1-4}$alkylamino, $C_{3-6}$cycloalkyl, pyrrolidinyl, thienyl, furyl, quinolinyl, dihydrobenzofuranyl, pyrrolyl, 2-oxopyrrolidinyl-$C_{1-3}$alkyl, phenyl, benzyl, piperidinyl, azetidinyl and benzyloxy, wherein said $C_{1-6}$alkyl, $C_{1-4}$alkoxy, $C_{1-4}$alkylamino, di-$C_{1-4}$alkylamino, $C_{3-6}$cycloalkyl, pyrrolidinyl, furyl, quinolinyl, dihydrobenzofuranyl, pyrrolyl, 2-oxopyrrolidinyl-$C_{1-3}$alkyl, phenyl, benzyl, piperidinyl, azetidinyl and benzyloxy are optionally substituted by one or more groups selected from amino, halogen, phenyl, morpholinyl, $C_{3-6}$cycloalkyl, $C_{1-6}$alkyl, hydroxy, $C_{1-6}$alkoxy and —CN.

In a particular embodiment, $R^2$ of formula IIA is selected from methyl, ethyl, n-propyl, isopropyl, n-butyl, isobutyl, tertbutyl, 4-heptyl, 2-methyl-1-propyl, benzyl, phenyl, thienyl, furyl, quinolinyl, dihydrobenzofuranyl, pyrrolyl, 2-oxopyrrolidinyl-ethyl, methoxy, ethoxy, isopropoxy, propoxy, benzyloxy, t-butoxy, isopropenoxy, isobutoxy, $C_{3-6}$cycloalkoxy, cyclopropyl, cyclobutyl, cyclopentyl, cyclohexyl, pyrrolidinyl, piperidinyl, azetidinyl, methylamino, and ethylamino, which are optionally substituted by one or more groups selected from amino, halogen, phenyl, morpholinyl, $CF_3$, —C(=O)$C_{1-6}$alkyl, $C_{3-6}$cycloalkyl, $C_{1-6}$alkyl, hydroxy, $C_{1-6}$alkoxy and —CN.

In another particular embodiment, n of formula IIA is 1.

In a further particular embodiment, n of formula IIA is 2.

In a further embodiment, the present invention provides a compound of formula X, a pharmaceutically acceptable salt thereof, diastereomer, enantiomer, or mixture thereof:

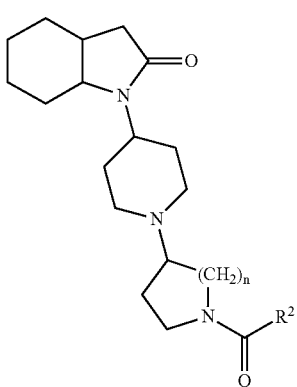

wherein $R^2$ is selected from hydrogen, $C_{1-6}$alkyl, $C_{2-6}$alkenyl, $C_{1-6}$alkoxy, $C_{1-6}$alkylamino, di-$C_{1-6}$alkylamino, $C_{6-10}$aryl, $C_{6-10}$aryloxy, $C_{2-9}$heteroaryl, $C_{2-9}$heteroaryloxy, $C_{3-5}$heterocycloalkyloxy, $C_{3-5}$heterocycloalkyl, $C_{6-10}$aryl-$C_{1-3}$alkoxy, $C_{6-10}$aryl-$C_{1-3}$alkyl, $C_{2-9}$heteroaryl-$C_{1-3}$alkoxy, $C_{2-9}$heteroaryl-$C_{1-3}$alkyl, $C_{3-5}$heterocycloalkyl-$C_{1-3}$alkoxy, $C_{3-5}$heterocycloalkyl-$C_{1-3}$alkyl, $C_{3-6}$cycloalkyl, $C_{3-6}$cycloalkyloxy, and $C_{3-6}$cycloalkyl-$C_{1-3}$alkyl, $C_{3-6}$cycloalkyl-$C_{1-3}$alkoxy, wherein said $C_{1-6}$alkyl, $C_{2-6}$alkenyl, $C_{1-6}$alkyl-carbonyl, $C_{1-6}$alkylaminocarbonyl, $C_{6-10}$aryl, $C_{2-9}$heteroaryl, $C_{3-5}$heterocycloalkyl, $C_{6-10}$aryl-$C_{1-3}$alkyl, $C_{2-9}$heteroaryl-$C_{1-3}$alkyl, $C_{3-5}$heterocycloalkyl-$C_{1-3}$alkyl, $C_{3-6}$cycloalkyl, and $C_{3-6}$cycloalkyl-$C_{1-3}$alkyl are optionally substituted with one or more group selected from phenyl, $C_{3-6}$cycloalkyl, $C_{2-5}$heterocycloalkyl, $C_{2-5}$heteroaryl, —CN, —SR, —OR, —O(CH$_2$)$_p$—OR, R, —C(=O)—R, —CO$_2$R, —SO$_2$R, —SO$_2$NR$_2$, halogen, —NO$_2$, —NR$_2$, —(CH$_2$)$_p$NR$_2$, and —C(=O)—NR$_2$;

p is 1, 2, 3 or 4; n is 1, 2;

and each R, is independently hydrogen, $C_{1-6}$alkyl, $C_{2-6}$alkenyl or halogenated $C_{1-6}$alkyl.

In a further particular embodiment, $R^2$ of formula X is selected from hydrogen, $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{2-5}$heterocycloalkyl-$C_{1-3}$alkyl, phenyl, benzyl, $C_{2-9}$heteroaryl, $C_{1-6}$alkoxy, $C_{1-6}$alkylamino, di-$C_{1-6}$alkylamino and benzyloxy, wherein said $C_{1-6}$alkyl, $C_{3-6}$cycloalkyl, $C_{3-6}$cycloalkoxy, $C_{3-6}$cycloalkyl-$C_{1-3}$alkoxy, $C_{2-5}$heterocycloalkyl, $C_{2-5}$heterocycloalkyl-$C_{1-3}$alkyl, phenyl, benzyl, $C_{2-9}$heteroaryl, $C_{1-6}$alkoxy, $C_{1-6}$alkylamino, di-$C_{1-6}$alkylamino and benzyloxy are optionally substituted by one or more groups selected from amino, halogen, phenyl, morpholinyl, $C_{3-6}$cycloalkyl, $C_{1-6}$alkyl, hydroxy, $C_{1-6}$alkoxy and —CN.

In a further particular embodiment, $R^2$ of formula X is selected from hydrogen, $C_{1-6}$alkyl, $C_{1-4}$alkoxy, $C_{1-4}$alkylamino, di-$C_{1-4}$alkylamino, $C_{3-6}$cycloalkyl, pyrrolidinyl, thienyl, furyl, quinolinyl, dihydrobenzofuranyl, pyrrolyl, 2-oxopyrrolidinyl-$C_{1-3}$alkyl, phenyl, benzyl, piperidinyl, azetidinyl and benzyloxy, wherein said $C_{1-6}$alkyl, $C_{1-4}$alkoxy, $C_{1-4}$alkylamino, di-$C_{1-4}$alkylamino, $C_{3-6}$cycloalkyl, pyrrolidinyl, furyl, quinolinyl, dihydrobenzofuranyl, pyrrolyl, 2-oxopyrrolidinyl-$C_{1-3}$alkyl, phenyl, benzyl, piperidinyl, azetidinyl and benzyloxy are optionally substituted by one or more groups selected from amino, halogen, phenyl, morpholinyl, $C_{3-6}$cycloalkyl, $C_{1-6}$alkyl, hydroxy, $C_{1-6}$alkoxy and —CN.

In a further particular embodiment, $R^2$ of formula X is selected from methyl, ethyl, n-propyl, isopropyl, n-butyl, isobutyl, tertbutyl, 4-heptyl, 2-methyl-1-propyl, benzyl, phenyl, thienyl, furyl, quinolinyl, dihydrobenzofuranyl, pyrrolyl, 2-oxopyrrolidinyl-ethyl, methoxy, ethoxy, isopropoxy, propoxy, benzyloxy, t-butoxy, isopropenoxy, isobutoxy, $C_{3-6}$cycloalkoxy, cyclopropyl, cyclobutyl, cyclopentyl, cyclohexyl, pyrrolidinyl, piperidinyl, azetidinyl, methylamino, and ethylamino, which are optionally substituted by one or more groups selected from amino, halogen, phenyl, morpholinyl, $CF_3$, —C(=O)$C_{1-6}$alkyl, $C_{3-6}$cycloalkyl, $C_{1-6}$alkyl, hydroxy, $C_{1-6}$alkoxy and —CN.

In another embodiment, n of formula X is 1.

In another embodiment, n of formula X is 2.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I or II. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I or II. It will further be understood that the present invention encompasses tautomers of the compounds of the Formula I or II.

It will also be understood that certain compounds of the present invention may exist in solvated, for example hydrated, as well as unsolvated forms. It will further be understood that the present invention encompasses all such solvated forms of the compounds of the Formula I or II.

Within the scope of the invention are also salts of the compounds of the Formula I or II. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of Formula I or II above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

We have now found that the compounds of the invention have activity as pharmaceuticals, in particular as agonists of M1 receptors. More particularly, the compounds of the invention exhibit selective activity as agonist of the M1 receptors and are useful in therapy, especially for relief of various pain conditions such as chronic pain, neuropathic pain, acute pain, cancer pain, pain caused by rheumatoid arthritis, migraine, visceral pain etc. This list should however not be interpreted as exhaustive. Additionally, compounds of the present invention are useful in other disease states in which dysfunction of M1 receptors is present or implicated. Furthermore, the compounds of the invention may be used to treat cancer, multiple sclerosis, Parkinson's disease, Huntington's chorea, schizophrenia, Alzheimer's disease, anxiety disorders, depression, obesity, gastrointestinal disorders and cardiovascular disorders.

In a particular embodiment, the compounds may be used to treat schizophrenia or Alzheimer's disease.

In another embodiment, the compounds may be used to treat pain.

In another particular embodiment, the compounds may be used to treat neuropathic pain.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of M1 receptors is present or implicated in that paradigm. This may involve the use of isotopically labeled versions of the compounds of the invention in diagnostic techniques and imaging applications such as positron emission tomography (PET).

Compounds of the invention are useful for the treatment of diarrhea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastrointestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, obesity, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the Formula I or II above, for the manufacture of a medicament for the treatment of any of the conditions discussed above.

A further aspect of the invention is a method for the treatment of a subject suffering from any of the conditions discussed above, whereby an effective amount of a compound according to the Formula I or II above, is administered to a patient in need of such treatment.

Thus, the invention provides a compound of Formula I or II or pharmaceutically acceptable salt or solvate thereof, as hereinbefore defined for use in therapy.

In a further aspect, the present invention provides the use of a compound of Formula I or II or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain. In a particular embodiment, the compounds are useful in therapy for neuropathic pain. In an even more particular embodiment, the compounds are useful in therapy for chronic neuropathic pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, transdermally, intracerebroventricularly and by injection into the joints.

In one embodiment of the invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of Formula I or II as defined above for the manufacture of a medicament.

Also within the scope of the invention is the use of any compound of Formula I or II for the manufacture of a medicament for the therapy of pain.

Additionally provided is the use of any compound according to Formula I or II for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the Formula I or II above, is administered to a patient in need of such therapy.

Additionally, there is provided a pharmaceutical composition comprising a compound of Formula I or II or a pharmaceutically acceptable salt thereof, in association with a pharmaceutically acceptable carrier.

Particularly, there is provided a pharmaceutical composition comprising a compound of Formula I or II or a pharmaceutically acceptable salt thereof, in association with a pharmaceutically acceptable carrier for therapy, more particularly for therapy of pain.

Further, there is provided a pharmaceutical composition comprising a compound of Formula I or II or a pharmaceutically acceptable salt thereof, in association with a pharmaceutically acceptable carrier use in any of the conditions discussed above.

In a further embodiment, a compound of the present invention, or a pharmaceutical composition or formulation comprising a compound of the present invention may be administered concurrently, simultaneously, sequentially or separately with one or more pharmaceutically active compound(s) selected from the following:

(i) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robalzotan, sertraline, sibutramine, thionisoxetine, tranylcypromaine, trazodone, trimipramine, venlafaxine and equivalents and pharmaceutically active isomer(s) and metabolite(s) thereof;

(ii) atypical antipsychotics including for example quetiapine and pharmaceutically active isomer(s) and metabolite(s) thereof; amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, lithium, loxapine, mesoridazine, olanzapine, paliperidone, perlapine, perphenazine, phenothiazine, phenylbutlypiperidine, pimozide, prochlorperazine, risperidone, quetiapine, sertindole, sulpiride, suproclone, suriclone, thioridazine, trifluoperazine, trimetozine, valproate, valproic acid, zopiclone, zotepine, ziprasidone and equivalents thereof;

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof;

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof;

(v) anticonvulsants including, for example, carbamazepine, valproate, lamotrogine, gabapentin and equivalents and pharmaceutically active isomer(s) and metabolite(s) thereof;

(vi) Alzheimer's therapies including, for example, donepezil, memantine, tacrine and equivalents and pharmaceutically active isomer(s) and metabolite(s) thereof;

(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including, for example, abciximab, activase, NXY-059, citicoline, crobenetine, desmoteplase, repinotan, traxoprodil and equivalents and pharmaceutically active isomer(s) and metabolite(s) thereof;

(x) over active bladder urinary incontinence therapies including, for example, darafenacin, falvoxate, oxybutynin, propiverine, robalzotan, solifenacin, tolterodine and equivalents and pharmaceutically active isomer(s) and metabolite(s) thereof;

(xi) neuropathic pain therapies including, for example, gabapentin, lidoderm, pregablin and equivalents and pharmaceutically active isomer(s) and metabolite(s) thereof;

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, zolpidem and equivalents and pharmaceutically active isomer(s) and metabolite(s) thereof; and (xiv) mood stabilizers including, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combinations employ the compounds of this invention within the dosage range described herein and the other pharmaceutically active compound or compounds within approved dosage ranges and/or the dosage described in the publication reference.

In an even further embodiment, a compound of the present invention, or a pharmaceutical composition or formulation comprising a compound of the present invention may be administered concurrently, simultaneously, sequentially or separately with one or more pharmaceutically active compound(s) selected from buprenorphine; dezocine; diacetylmorphine; fentanyl; levomethadyl acetate; meptazinol; morphine; oxycodone; oxymorphone; remifentanil; sufentanil; and tramadol.

In a particular embodiment, it may be particularly effective to administrate a combination containing a compound of the invention and a second active compound selected from buprenorphine; dezocine; diacetylmorphine; fentanyl; levomethadyl acetate; meptazinol; morphine; oxycodone; oxymorphone; remifentanil; sufentanil; and tramadol to treat chronic nociceptive pain. The efficacy of this therapy may be demonstrated using a rat FCA-induced heat hyperalgesia model described below.

In a further aspect, the present invention provides a method of preparing the compounds of the present invention.

In one embodiment, the invention provides a process for preparing a compound of Formula I, comprising:

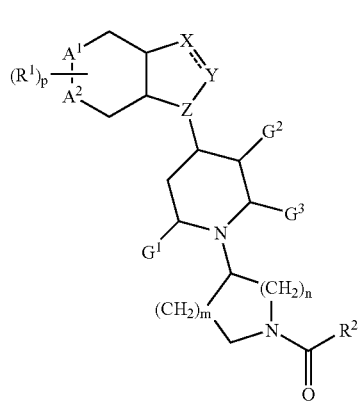

reacting a compound of Formula III with a compound of formula IV,

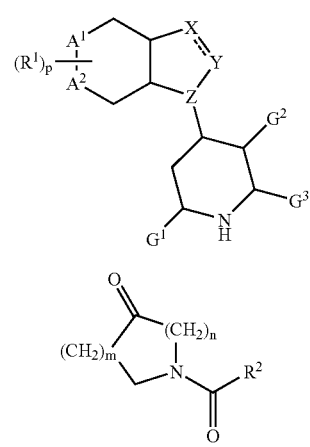

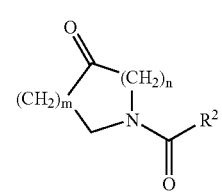

wherein $A^1, A^2, G^1, G^2, G^3, R^1, R^2$, m, n, p, X, Y and Z are defined as above.

Optionally, the step of reacting a compound of formula III with a compound of formula IV is carried out in the presence of a reducing agent, such as $NaBH(OAc)_3$, $NaBH_4$ or equivalents thereof.

In another embodiment, the invention provides a process for preparing a compound of Formula I, comprising:

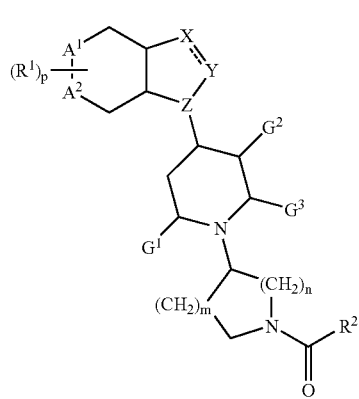

reacting a compound of Formula V with a compound of Q-C(=O)—R²

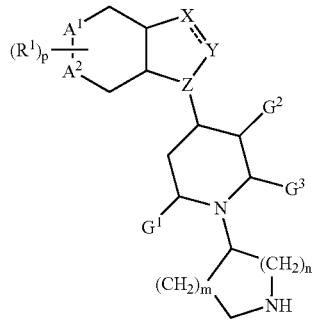

V wherein A¹, A², G¹, G², G³, R¹, R², m, n, p, X, Y and Z are defined as above; and Q is a halogen or OH.

Optionally, the step of reacting a compound of formula V with a compound of Q-C(=O)—R², is carried out in the presence of a base, such as diisopropylethylamine, triethylamine or equivalents thereof.

In a further embodiment, the present invention provides a process for preparing a compound of Formula IA, comprising:

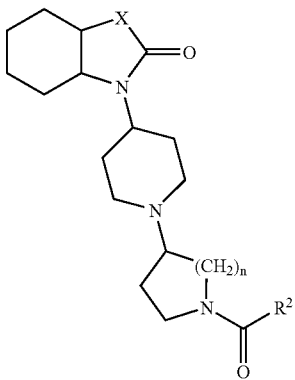

IA reacting a compound of Formula IIIA with a compound of formula IV,

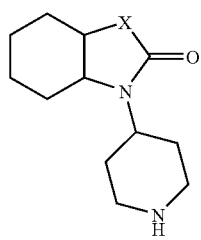

IIIA

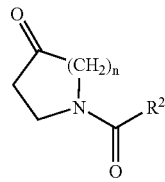

IV wherein R², n, X, and Q are as defined above.

Optionally, the step of reacting a compound of formula III with a compound of formula IV is carried out in the presence of a reducing agent, such as NaBH(OAc)₃, NaBH₄ or equivalents thereof.

In another embodiment, the present invention provides a process for preparing a compound of Formula IA, comprising:

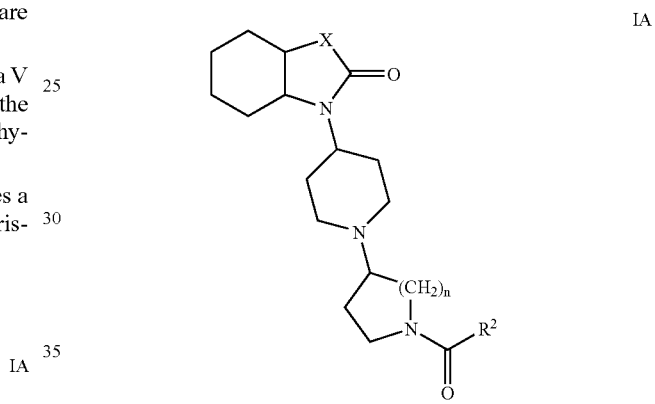

IA reacting a compound of Formula V with a compound of Q-C(=O)—R²

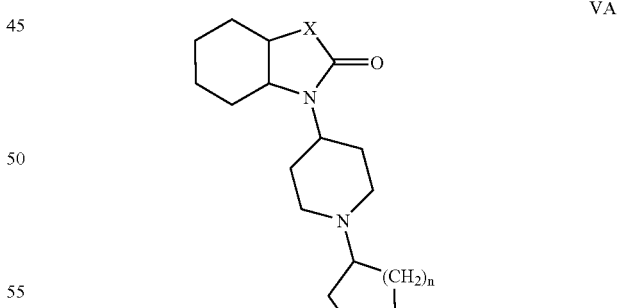

VA wherein R², n, X, and Q are as defined above.

Optionally, the step of reacting a compound of formula V with a compound of Q-C(=O)—R², is carried out in the presence of a base, such as diisopropylethylamine, triethylamine or equivalents thereof.

In a further embodiment, the present invention provides an intermediate of formula VA, a pharmaceutically acceptable salt thereof, diastereomer, enantiomer, or mixture thereof:

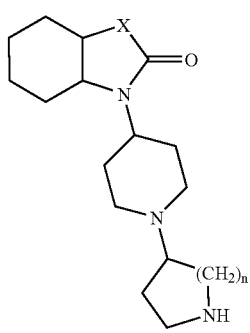
wherein
n is 1, 2;
X, is independently selected from NH, N—R, CH₂ CHR, and CRR'; and each R, R' is independently hydrogen, $C_{1-6}$alkyl, $C_{2-6}$alkenyl or halogenated $C_{1-6}$alkyl.
Compounds of the present invention may also be prepared according to the synthetic routes as depicted in Schemes 1-7.
Scheme 1 (Intermediate 1 and 2)
Scheme 2 (Examples 1-7, 14-18, 60, 61):
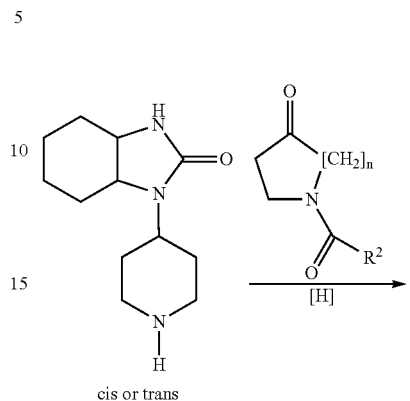
cis or trans
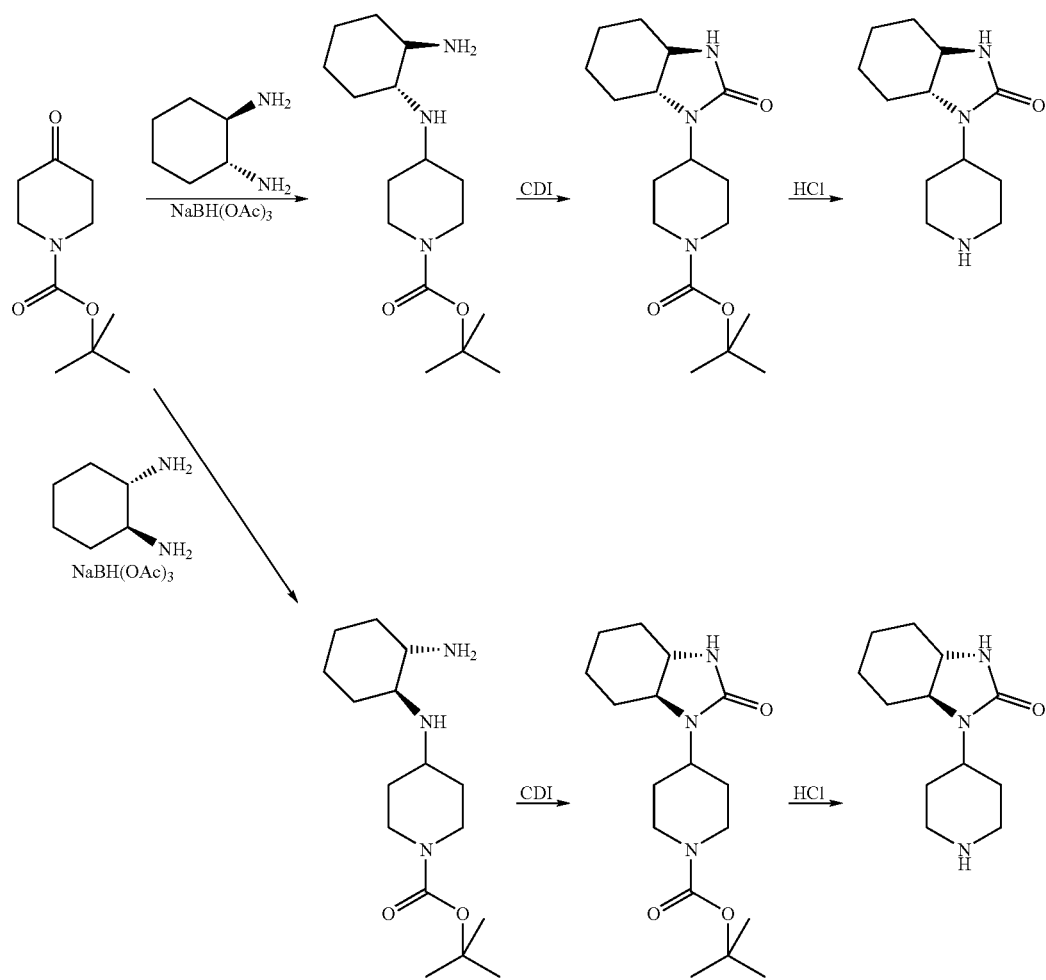

Scheme 4 (Example 62):
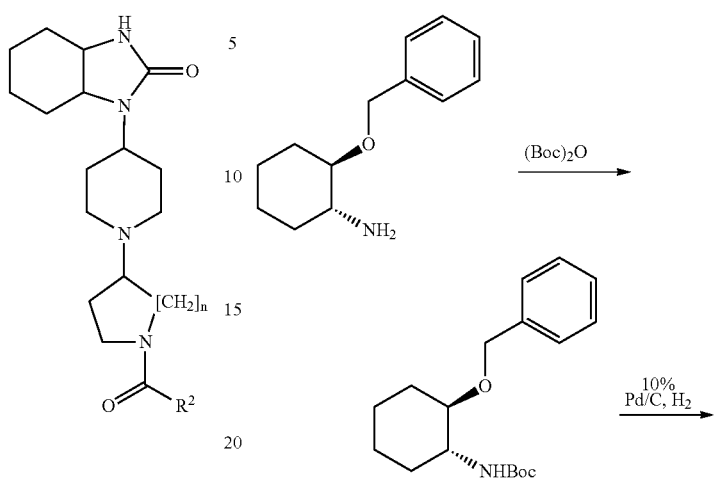
Scheme 3 (Examples 8-13, 19-59, 63-68, 75-86):
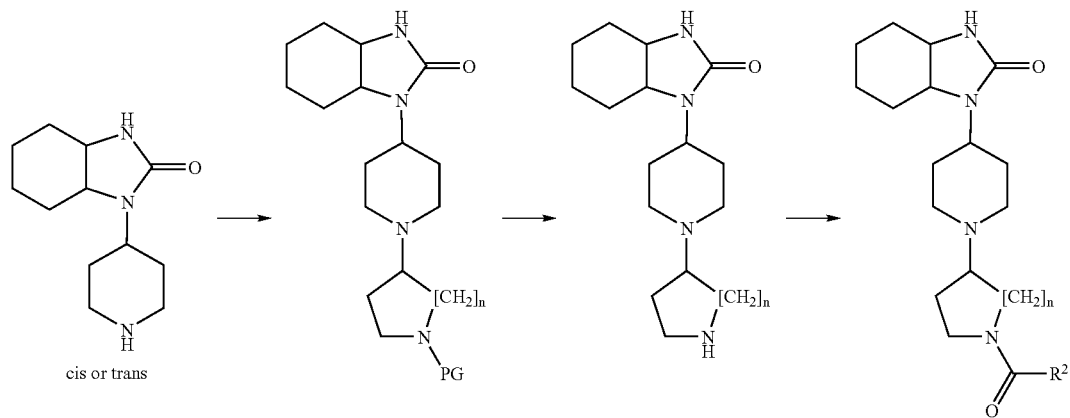
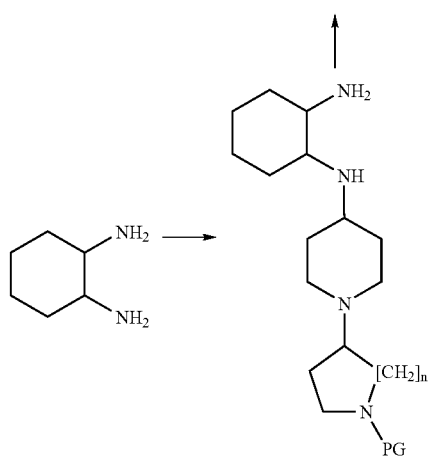
"PG" means "protecting group"

-continued
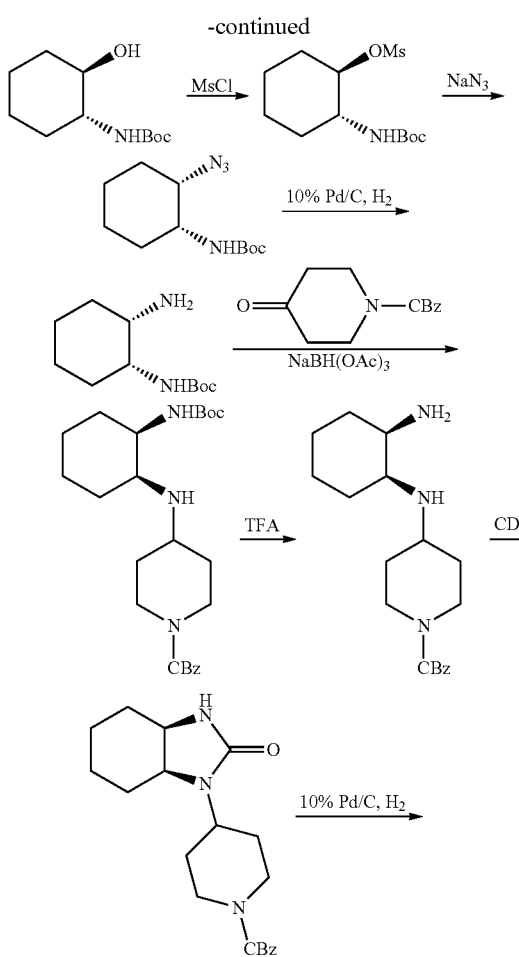
Scheme 5 (Examples 69-74):
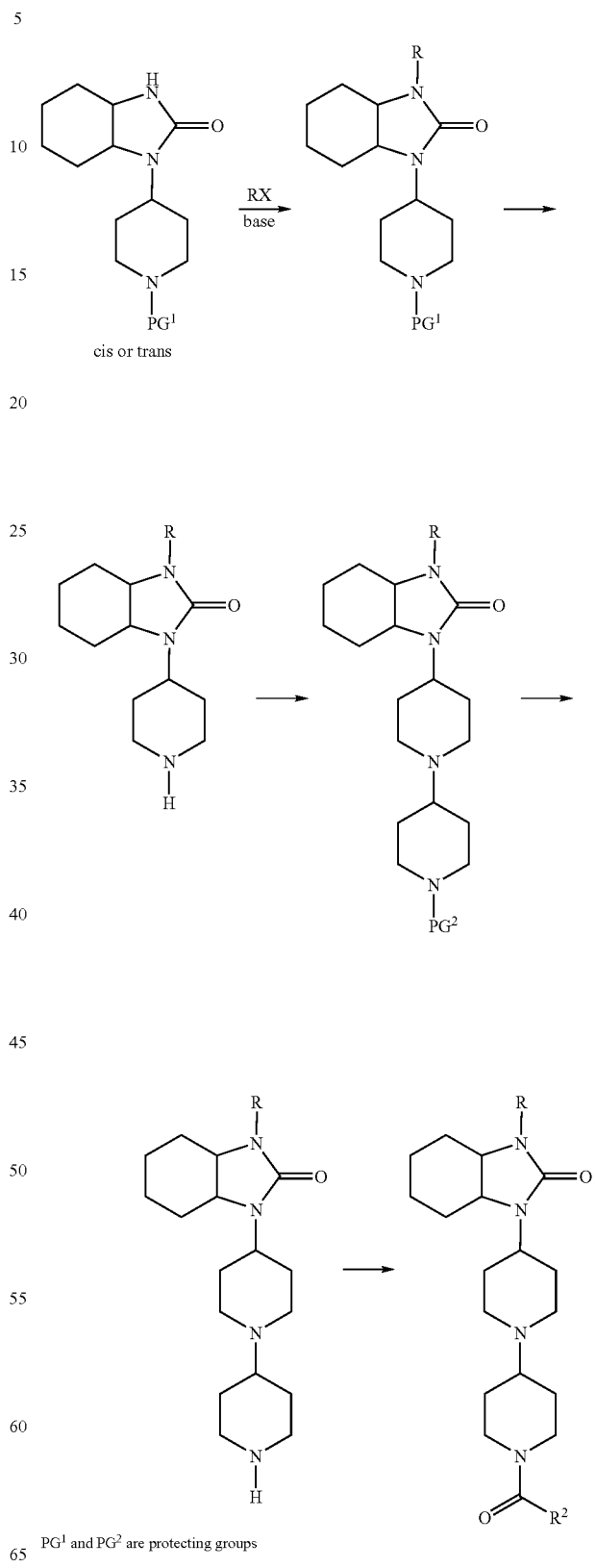
PG¹ and PG² are protecting groups Scheme 6 (Example 87-89):
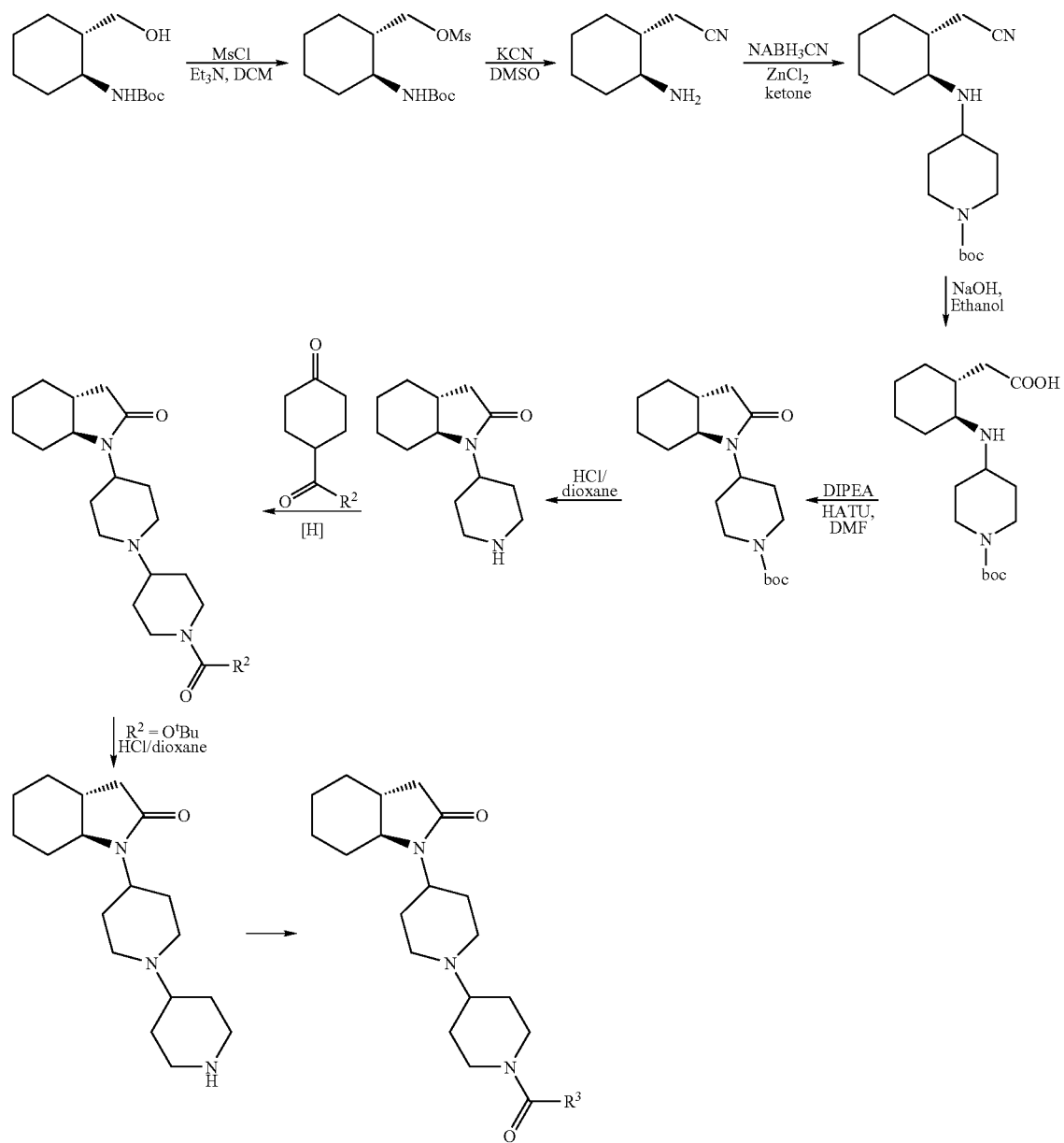
Scheme 7 (Example 90, 91):
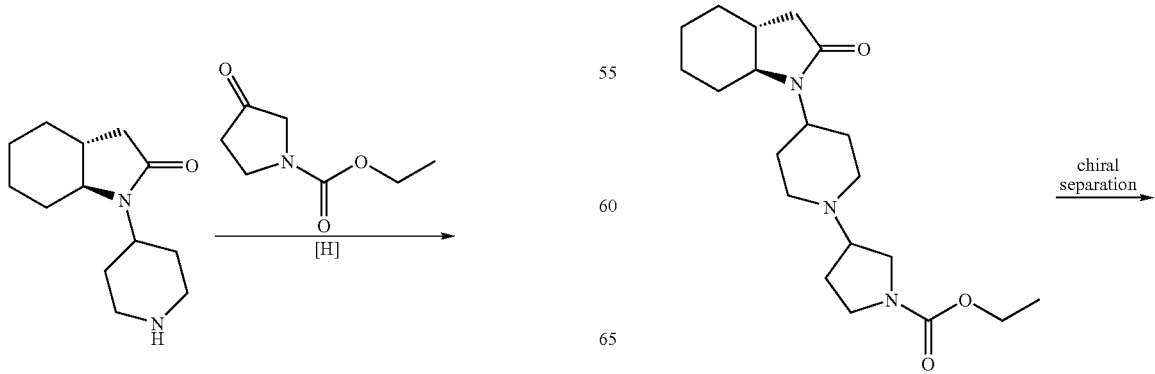

-continued

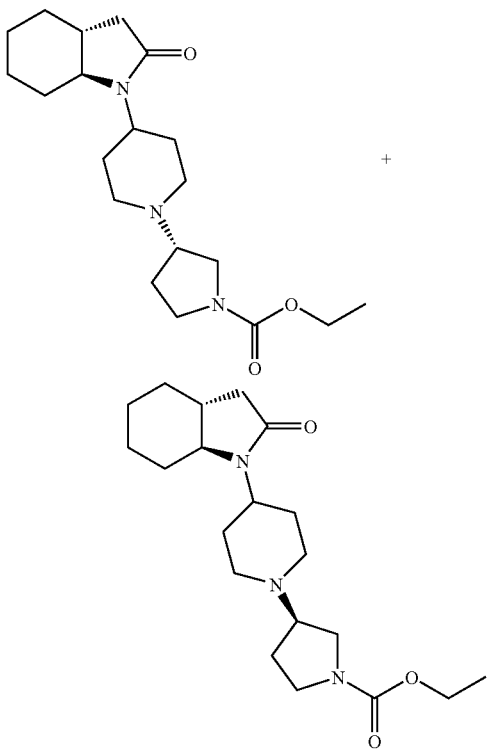

Biological Evaluation
Human M1, Rat M1, Human M3 and Human M5 Calcium Mobilization FLIPR™ Assay The compound activity in the present invention (EC50 or $IC_{50}$) was measured using a 384 plate-based imaging assay that monitors drug induced intracellular $Ca^2$ release in whole cells. Activation of hM1 (human Muscarinic receptor subtype 1, gene bank access NM_000738), rM1 (rat Muscarinic receptor subtype 1, gene bank access NM_080773), hM3 (human Muscarinic receptor subtype 3, gene bank access NM_000740NM_000740) and hM5 (human Muscarinic receptor subtype 5, gene bank access NM_0121258), receptors expressed in CHO cells (Chinese hamster ovary cells, ATCC) was quantified in a Molecular Devices FLIPR II™ instrument as an increase in fluorescent signal. Inhibition of hM3 and hM5 by compounds was determined by the decrease in fluorescent signal in response to 20 nM carbachol activation.

CHO cells were plated in 384-black polylysine coated plate (Costar) at 8000 cells/well/50 μl for 24 hours or 4000 cells/well for 48 hours in a humidified incubator (5% $CO_2$ and 37° C.) in DMEM/F12 medium without selection agent. Prior to the experiment the cell culture medium was removed from the plates by inversion. A loading solution of 30 μl of Hank's balanced salt solution, 10 mM Hepes and 2.5 mM Probenicid at Ph 7.4 (Cat no. 311-520-VL, Wisent) with 2 μM calcium indicator dye (FLUO-3AM, Molecular Probes F14202) was added to each well. Plates were incubated at 37° C. for 60 minutes prior to start the experiment. The incubation was terminated by washing the cells four times in assay buffer, leaving a residual 25 μl buffer per well. Cell plates were then transferred to the FLIPR, ready for compound additions.

The day of experiment, carbachol and compounds were diluted in three-fold concentration range (10 points serial dilution) for addition by FLIPR instrument. For all calcium assays, a baseline reading was taken for 30 seconds followed by the addition of 12.5 μl (25 μl for hM1 and rM1) of compounds, resulting in a total well volume of 37.5 μl (50 μl for hM1 and rM1). Data were collected every 1.6 seconds for 300 seconds. For hM3 and hM5 an additional 12.5 μl of carbachol (20 nM final) was added at 300 seconds. After this addition of carbachol (producing a final volume of 50 μl), the FLIPR continued to collect data every 2 seconds for 240 seconds. The fluorescence emission was read using filter 1 (emission 520-545 nm) by the FLIPR on board CCD camera.

Calcium mobilization output data were calculated as the maximal relative fluorescence unit (RFU) minus the minal value for both compound and agonist reading frame (except for hM1 and rM1 using only the maximal RFU). Data were analyzed using sigmoidal fits of a non-linear curve-fitting program (XLfit version 5.0.6 from ID Business Solutions Limited, Guildford, UK). All EC50 and IC50 values are reported as arithmetic means±standard error of mean of 'n' independent experiments. Using the above-mentioned assays, the IC50 and EC50 towards human hM1, ratM1, hM3 and hM5 receptors for most compounds is measured to be in the range 1->30000 nM. The $E_{max}$ (maximal effect, agonism or antagonist inhibition) towards human hM1, ratM1, hM3 and hM5 receptors for most compounds is measured to be in the range of 0-110%.

hM2 Receptor GTPγS Binding

Membranes produced from Chinese hamster ovary cells (CHO) expressing the cloned human M2 receptor (human Muscarinic receptor subtype 2, gene bank access NM_000739), were obtained from Perkin-Elmer (RBHM2M). The membranes were thawed at 37° C., passed 3 times through a 23-gauge blunt-end needle, diluted in the GTPγS binding buffer (50 mM Hepes, 20 mM NaOH, 100 mM NaCl, 1 mM EDTA, 5 mM $MgCl_2$, pH 7.4, 100 μM DTT). The $EC_{50}$, $IC_{50}$ and $E_{max}$ of the compounds of the invention were evaluated from 10-point dose-response curves (three fold concentration range) done in 60 μl in 384-well non-specific binding surface plate (Corning). Ten microliters from the dose-response curves plate (5× concentration) were transferred to another 384 well plate containing the following: 10 μg of hM2 membranes, 500 μg of Flashblue beads (Perkin-Elmer) and GDP in a 25 μl volume. An additional 15 μl containing 3.3× (55000 dpm) of GTPγ$^{35}$S (0.4 nM final) were added to the wells resulting in a total well volume of 50 μl. Basal and maximal stimulated [$^{35}$S]GTPγS binding were determined in absence and presence of 30 μM of acetylcholine agonist. The membranes/beads mix were pre-incubated for 15 minutes at room temperature with 25 μM GDP prior to distribution in plates (12.5 μM final). The reversal of acetylcholine-induced stimulation (2 μM final) of [$^{35}$S]GTPγS binding was used to assay the antagonist properties ($IC_{50}$) of the compounds. The plates were incubated for 60 minutes at room temperature with shaking, then centrifuged at 2000 rpm for 5 minutes. The radioactivity (cpm) were counted in a Trilux (Perkin-Elmer).

Values of $EC_{50}$, $IC_{50}$ and $E_{max}$ were obtained using sigmoidal fits of a non-linear curve-fitting program (XLfit version 5.0.6 from ID Business Solutions Limited, Guildford, UK) of percent stimulated [$^{35}$S]GTPγS binding vs. log(molar ligand).

All EC50 and IC50 values are reported as arithmetic means ± standard error of mean of 'n' independent experiments. Based on the above assays, the $EC_{50}$ towards human M2 receptors for most compounds of the invention is measured to be in the range of about between 200 and >30000 nM. The $E_{max}$ (maximal effect, agonism or antagonist inhibition) towards human M2 receptors for most compounds of the invention were measured to be in the range of about 0-120%. The $IC_{50}$ was the concentration of the compound of the invention at which 50% inhibition of acetylcholine [$^{35}$S]GTPγS binding stimulation has been observed. The $IC_{50}$ towards human M2 receptors for most compounds of the invention was measured to be in the range of between 40 and >90000 nM.

HM4 Receptor GTPγS Binding

Membranes produced from Chinese hamster ovary cells (CHO) expressing the cloned human M4 receptor (human Muscarinic receptor subtype 4, gene bank access NM_000741), were obtained from Perkin-Elmer (RBHM4M). The membranes were thawed at 37° C., passed 3 times through a 23-gauge blunt-end needle, diluted in the GTPγS binding buffer (50 mM Hepes, 20 mM NaOH, 100 mM NaCl, 1 mM EDTA, 5 mM MgCl$_2$, pH 7.4, 100 µM DTT). The $EC_{50}$, $IC_{50}$ and $E_{max}$ of the compounds of the invention were evaluated from 10-point dose-response curves (three fold concentration range) done in 60 µl in 384-well non-specific binding surface plate (Corning). Ten microliters from the dose-response curves plate (5× concentration) were transferred to another 384 well plate containing the following: 10 µg of hM4 membranes, 500 µg of Flashblue beads (Perkin-Elmer) and GDP in a 25 µl volume. An additional 15 µl containing 3.3× (55000 dpm) of GTPγ$^{35}$S (0.4 nM final) were added to the wells resulting in a total well volume of 50 µl. Basal and maximal stimulated [$^{35}$S]GTPγS binding were determined in absence and presence of 30 µM of acetylcholine agonist. The membranes/beads mix were pre-incubated for 15 minutes at room temperature with 40 µM GDP prior to distribution in plates (20 µM final). The reversal of acetylcholine-induced stimulation (10 µM final) of [$^{35}$S]GTPγS binding was used to assay the antagonist properties ($IC_{50}$) of the compounds. The plates were incubated for 60 minutes at room temperature with shaking, then centrifuged at 2000 rpm for 5 minutes. The radioactivity (cpm) were counted in a Trilux (Perkin-Elmer).

Values of $EC_{50}$, $IC_{50}$ and $E_{max}$ were obtained using sigmoidal fits of a non-linear curve-fitting program (XLfit version 5.0.6 from ID Business Solutions Limited, Guildford, UK) of percent stimulated [$^{35}$S]GTPγS binding vs. log(molar ligand).

All EC50 and IC50 values are reported as arithmetic means±standard error of mean of 'n' independent experiments. Based on the above assays, the $EC_{50}$ towards human M4 receptors for most compounds of the invention is measured to be in the range of between 300 and >30000 nM. The $E_{max}$ (maximal effect, agonism or antagonist inhibition) towards human M4 receptors for most compounds of the invention were measured to be in the range of about 0-120%. The $IC_{50}$ was the concentration of the compound of the invention at which 50% inhibition of acetylcholine [$^{35}$S]GTPγS binding stimulation has been observed. The $IC_{50}$ towards human M4 receptors for most compounds of the invention was measured to be in the range of between 3000 and >30000 nM.

Certain biological properties of certain compounds of the invention measured using one or more assays described above are listed in Table 1 below.

TABLE 1

Certain Biological Properties of the Certain Compounds of the Invention.

| Compound Structure | hM1 EC50 (nM) | hM2 EC50 (nM) | hM3 EC50 (nM) | hM4 EC50 (nM) | hM5 EC50 (nM) |
|---|---|---|---|---|---|
| <br>a = relative mixture | | 1000 | | | |

TABLE 1-continued

Certain Biological Properties of the Certain Compounds of the Invention.

| Compound Structure | hM1 EC50 (nM) | hM2 EC50 (nM) | hM3 EC50 (nM) | hM4 EC50 (nM) | hM5 EC50 (nM) |
|---|---|---|---|---|---|
| Chiral structure | 1.1 | 120 | 2500 | 330 | 220 |
| Chiral structure | 5 | 7300 | >40000 | 9400 | 3900 |
| Structure (a = 1:1) | 300 | | | | |

TABLE 1-continued

Certain Biological Properties of the Certain Compounds of the Invention.

| Compound Structure | hM1 EC50 (nM) | hM2 EC50 (nM) | hM3 EC50 (nM) | hM4 EC50 (nM) | hM5 EC50 (nM) |
| --- | --- | --- | --- | --- | --- |
| [Structure 1] | 600 | | | | |
| [Structure 2] | 200 | >30000 | >40000 | >30000 | >40000 |
| [Structure 3] | 4.6 | 760 | >40000 | 1300 | 36 |

TABLE 1-continued
Certain Biological Properties of the Certain Compounds of the Invention.
| Compound Structure | | hM1 EC50 (nM) | hM2 EC50 (nM) | hM3 EC50 (nM) | hM4 EC50 (nM) | hM5 EC50 (nM) |
| --- | --- | --- | --- | --- | --- | --- |
| 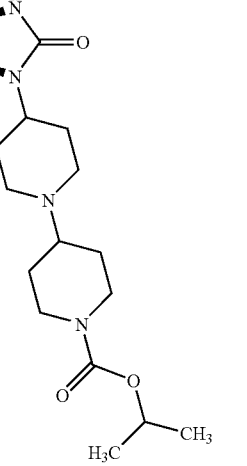 | | 15 | 2500 | >40000 | 4500 | 72 |
| 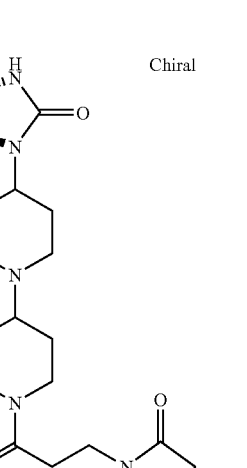 | Chiral | 6.8 | 500 | >40000 | 5100 | 1600 |
| 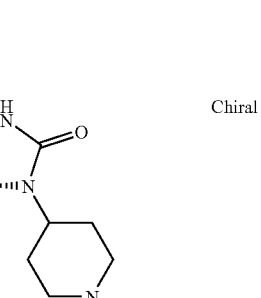 | Chiral | 46 | >30000 | >40000 | >30000 | >40000 |

TABLE 1-continued

Certain Biological Properties of the Certain Compounds of the Invention.

| Compound Structure | hM1 EC50 (nM) | hM2 EC50 (nM) | hM3 EC50 (nM) | hM4 EC50 (nM) | hM5 EC50 (nM) |
|---|---|---|---|---|---|
| Chiral | 9.2 | 1000 | 5400 | >30000 | 2400 |
| Chiral | 95 | 2600 | >40000 | >30000 | >40000 |
| Chiral | 1200 | | >40000 | | >40000 |

TABLE 1-continued
Certain Biological Properties of the Certain Compounds of the Invention.
| Compound Structure | hM1 EC50 (nM) | hM2 EC50 (nM) | hM3 EC50 (nM) | hM4 EC50 (nM) | hM5 EC50 (nM) |
|---|---|---|---|---|---|
| 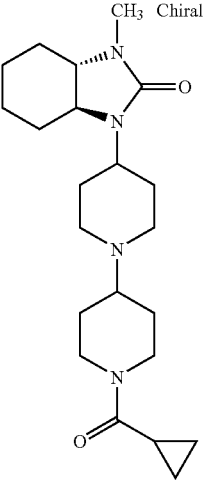 | 94 | >30000 | >40000 | >30000 | >40000 |
| 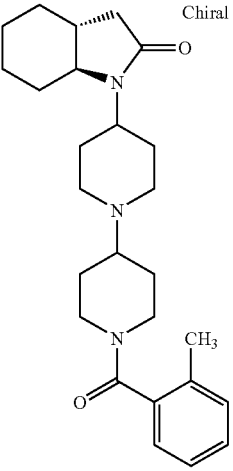 | 93 | | >40000 | | >40000 |
| 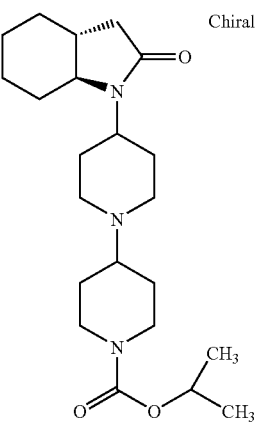 | 14 | 1200 | >40000 | 4200 | >40000 |

TABLE 1-continued

Certain Biological Properties of the Certain Compounds of the Invention.

| Compound Structure | hM1 EC50 (nM) | hM2 EC50 (nM) | hM3 EC50 (nM) | hM4 EC50 (nM) | hM5 EC50 (nM) |
|---|---|---|---|---|---|
| (Chiral structure) | 2.5 | 380 | | 1100 | |
| (Chiral structure) ISOMER 2 a = unknown absolute | 59 | | | | |
| (Chiral structure) | 81 | | | | |

Rat FCA-Induced Heat Hyperalgesia Model

Twenty four hours before testing, rats are brought to experimental lab. Rats are placed in a plexiglass chamber with 2% isoflurane at a flow rate of 0.8-1 L/hr with oxygen, for approximately 60-90 seconds, until a light-medium depth of anesthesia is attained. A volume of 25 µl of FCA is injected into the subcutaneous space of the dorsal aspect of the left hind paw, in the centre of the pads. This creates an inflammation, with accompanying edema and redness, as well as hyperalgesia, which is fully developed within 24 hours, and remains stable for weeks. In order to assess the degree of hyperalgesia, the animals are placed on a glass surface, and a heat-source is focused onto the plantar surface of the affected paw. The time from the initiation of the heat until the animal withdraws the paw is recorded. A decrease in Paw Withdrawal Latency (PWL) relative to naïve animals indicates a hyperalgesic state.

Generally, an experiment consists of 5 groups. One group is naïve and serves as baseline control. The other 4 groups receive FCA injection. One of the 4 groups serves as the vehicle control and the other receive drug treatment.

Drug or vehicle is administered 24 h after FCA inoculation. Rats are placed back in their home cage for 30 min, then, placed on the plantar apparatus for an additional 30 min for habituation. Total time of testing after drug administration is based on Tmax. The degree of reversal effect (heat hyperalgesia) is measured by the ability of a drug to return to normal levels (naïve PWL).

Statistical significance is determined using one-way ANOVA on raw data followed by a post-hoc Holm-Sidak t-test. The level of statistical significance is set at $p \leq 0.05$. Raw data are normalized using the following formula: % anti-hyperalgesia=(PWL(dose)−PWL(vehicle))/(PWL(naïve)−PWL(vehicle))×100. Data is expressed as mean±SEM.

A combination containing a compound of the present invention and morphine at a predetermined ratio (e.g., 0.64:1) may be tested using this instant model. The combination drugs may be administered to the rats subcutaneously, orally or combination thereof, simultaneously or sequentially. The results (expressed as $ED_{50}$) for the combination may be compared with results obtained singly for the compound of the instant invention and morphine at the same or similar dosage range. If the $ED_{50}$ of the combination is significantly lower than the theoretical $ED_{50}$ calculated based on the $ED_{50}$ measured using the compound of the invention and morphine singly, then a synergy for the combination is indicated.

EXAMPLES

The invention will further be described in more detail by the following Examples which describe methods whereby compounds of the present invention may be prepared, purified, analyzed and biologically tested, and which are not to be construed as limiting the invention.

Example 1

Ethyl 4-[(cis (+/−))-2-oxooctahydro-1H-benzimidazol-1-yl]-1,4'-bipiperidine-1'-carboxylate

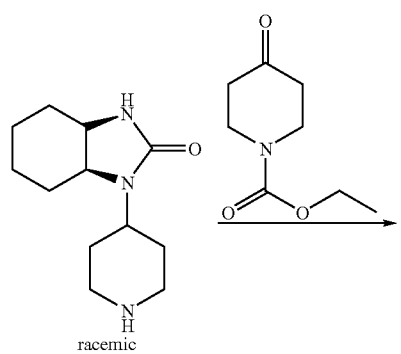
racemic

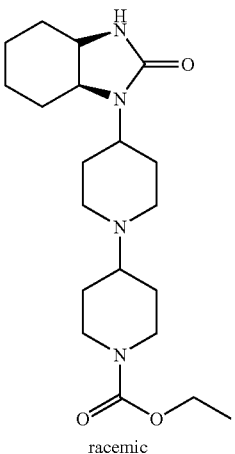
racemic

To a solution of racemic (cis)-1-piperidin-4-yloctahydro-2H-benzimidazol-2-one TFA salt (130 mg, 0.40 mmol) in dichloromethane (4 mL) was added acetic acid (120 μL) followed by ethyl 4-oxopiperidine-1-carboxylate (120 μL) and NaBH(OAc)$_3$ (250 mg), and the mixture was stirred at 45° C. overnight. The mixture was then quenched with a saturated solution of NaHCO$_3$ and then diluted in dichloromethane. 1N NaOH was added and aqueous phase was extracted several times with dichloromethane. The combined organic phase was dried and concentrated in vacuo. The compound was purified by high pH preparative LCMS to afford the title compound (25 mg). 1H NMR (400 MHz, CHLOROFORM-D): δ ppm 1.09-1.19 (m, 1H), 1.23 (t, J=7.16 Hz, 3H), 1.29-1.46 (m, 3H), 1.45-1.91 (m, 12H), 2.13-2.32 (m, 2H), 2.33-2.46 (m, 1H), 2.62-2.77 (m, 2H), 2.88 (d, J=12.69 Hz, 1H), 2.93 (d, J=11.13 Hz, 1H), 3.45-3.60 (m, 2H), 3.60-3.74 (m, 1H), 4.09 (q, J=7.16 Hz, 2H), 4.12-4.30 (m, 2H). 13C NMR (101 MHz, CHLOROFORM-D): δ ppm 14.57 (s, 1C), 19.63 (s, 1C), 20.56 (s, 1C), 26.26 (s, 1C), 27.30 (s, 1C), 42.38 (s, 1C), 48.43 (s, 1C), 51.86 (s, 1C), 61.77 (s, 1C), 63.92 (s, 1C), 154.92 (s, 1C), 162.48 (s, 1C). MS: (M+1) 379.3

Intermediate 1

(3aR,7aR)-1-piperidin-4-yloctahydro-2H-benzimidazol-2-one

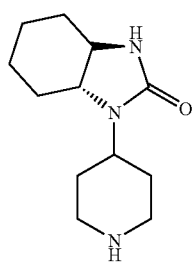

Step A

The preparation of tert-butyl 4-{[(1R,2R)-2-aminocyclohexyl]amino}piperidine-1-carboxylate

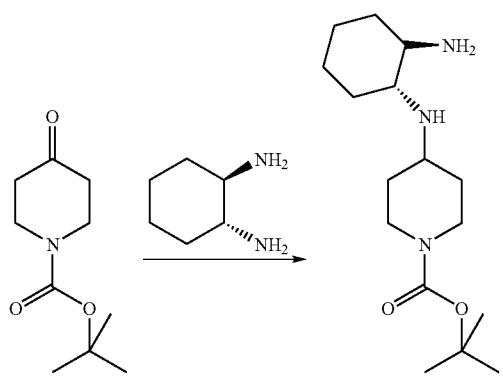

A mixture of (1R,2R)-cyclohexane diamine (20 g, 175 mmol) and sodium triacetoxyborohydride (25 g, 120 mmol) in dichloromethane (550 mL) was added with a solution of tert-butyl 4-oxopiperidine-1-carboxylate (18.4 g, 92 mmol) in dichloromethane (800 mL) dropwise over a period of 45 minutes and stirred at room temperature overnight. An aqueous solution of sodium bicarbonate (5%, 200 mL) was added to the reaction mixture, layers were separated, and the aqueous layer was extracted with dichloromethane (2×150 mL). The combined organic layers were dried over MgSO$_4$, filtered and concentrated in vacuo to afford the crude product which was purified by dry column vacuum chromatography to give the title compound as a pale yellow oil (18.0 g, 66%). 1H NMR (300 MHz, METHANOL-D4): δ ppm 3.99 (td, J=13.3, 3.3 Hz, 2H), 2.95-2.70 (m, 3H), 2.40-2.15 (m, 2H), 2.05 (m, 1H), 1.95-1.85 (m, 2H), 1.85-1.65 (m, 3H), 1.44 (s, 9H), 1.95-1.35 (m, 6H)

Step B

The preparation of tert-butyl 4-[(3aR,7aR)-2-oxooctahydro-1H-benzimidazol-1-yl]piperidine-1-carboxylate

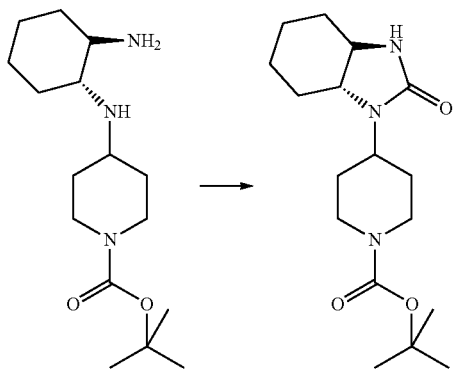

A solution of triphosgene (7.2 g, 24.2 mmol) in dichloromethane (300 mL) was added with a solution of tert-butyl 4-{[(1R,2R)-2-aminocyclohexyl]amino}piperidine-1-carboxylate (18 g, 60 mmol) and triethylamine in dichloromethane (600 mL) drop wise over a period of 1 h and stirred at room temperature for 22 h. An additional amount of triphosgene (8 g) and triethylamine (13 mL) were added and stirred at room temperature for another 22 h. An aqueous solution of sodium hydroxide (0.5N 200 mL) was added to the reaction mixture, layers were separated, and the aqueous layer was extracted with dichloromethane (2×100 mL). The combined organic layers were dried over Na$_2$SO$_4$, filtered and concentrated in vacuo to afford the crude product which was triturated with diethylether (80 mL) to give the title compound as white solid (11.1 g, 56%). 1H NMR (300 MHz, METHANOL-D4): δ ppm 4.25-4.05 (m, 2H), 3.80-3.65 (m, 1H), 3.10-2.90 (m, 2H), 2.85-2.65 (m, 2H), 2.20-1.90 (m, 2H), 1.90-1.55 (m, 4H), 1.55-1.30 (m, 11H)

Step C

The preparation of (3aR,7aR)-1-piperidin-4-yloctahydro-2H-benzimidazol-2-one

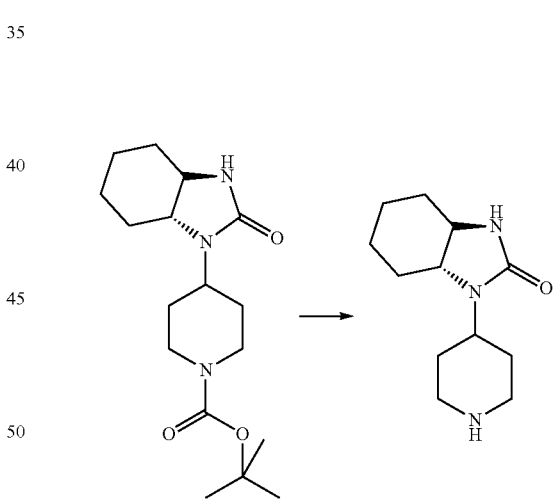

A solution of (3aR,7aR)-1-piperidin-4-yloctahydro-2H-benzimidazol-2-one (11.1 g, 34.3 mmol) in hydrochloric acid (70 mL, 5N in isopropanol) and in methanol (150 ml) and stirred at room temperature overnight. The mixture was concentrated in vacuo to give the title compound as a pale yellow solid (8.9 g, 100%). 1H NMR (300 MHz, METHANOL-D4): δ ppm 3.73 (tt, J=12.3, 4.1 Hz, 1H), 3.55-3.40 (m, 2H), 3.15-2.95 (m, 4H), 2.40-1.70 (m, 8H), 1.50-1.30 (m, 4H).

Intermediate 2

(3aS,7aS)-1-piperidin-4-yloctahydro-2H-benzimidazol-2-one

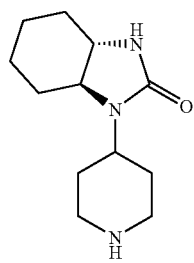

Step A

The preparation of tert-butyl 4-{[(1S,2S)-2-aminocyclohexyl]amino}piperidine-1-carboxylate

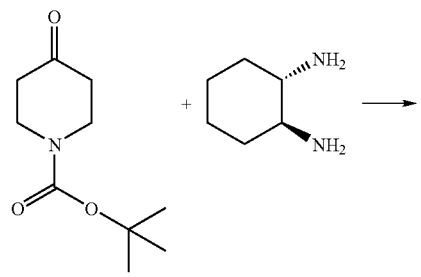

To a solution of (1S,2S)-cyclohexane-1,2-diamine (4 g, 35.08 mmol) in dichloromethane (80 mL) was added tert-butyl 4-oxopiperidine-1-carboxylate (3.49 g, 17.54 mmol) followed by sodium triacetoxy borohydride (11.15 g, 52.60 mmol) and stirred at room temperature for 5 hours. A saturated solution of sodium hydrogen carbonate (10 mL) was then added and the reaction diluted in dichloromethane (100 mL). The phases were separated and aqueous phase was extracted with dichloromethane (2×60 mL). Combined organic layers was washed with brine, dried and concentrated in vacuo. The crude compound was purified by flash chromatography to provide the titled compound as yellow oil (3.5 g).

Step B

The preparation of tert-butyl 4-(2-oxooctahydro-1H-benzimidazol-1-yl)piperidine-1-carboxylate

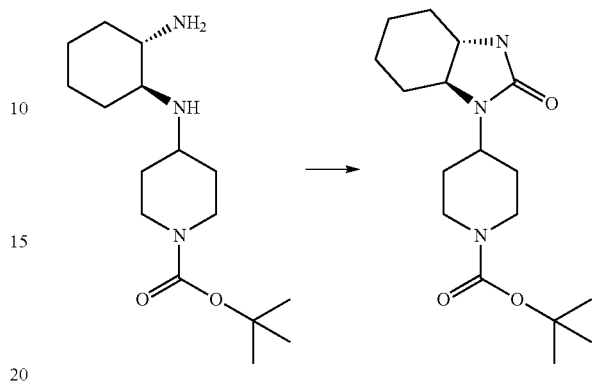

A solution of tert-butyl 4-{[(1S,2S)-2-aminocyclohexyl]amino}piperidine-1-carboxylate (3.5 g, 11.78 mmol) in acetonitrile (70 mL) was added with 1,1-carbonyldiimidazole (2.2 g, 13.58 mmol) and stirred at room temperature overnight. The solvent was removed under reduced pressure, taken in dichloromethane (200 mL) and washed with 1N NaOH (10 mL). The organic phase was dried and concentrated in vacuo. The residue was washed with diethyl ether (15 mL), dried and used for the next step without further purification (3.3 g). MS (M+1): 324.24

Step C

The preparation of (3aS,7aS)-1-piperidin-4-yloctahydro-2H-benzimidazol-2-one

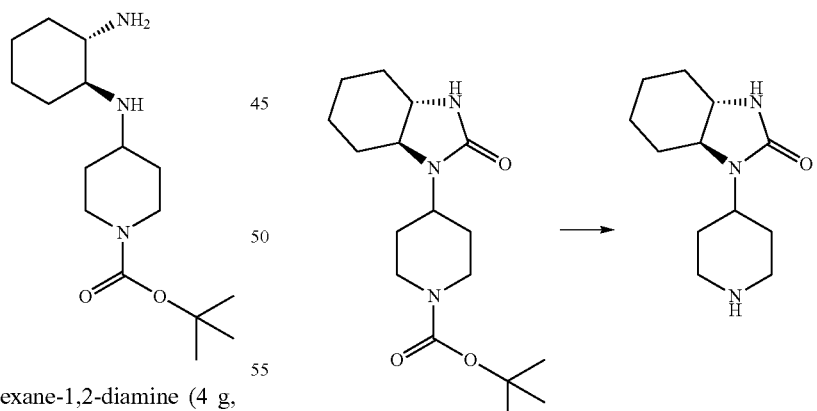

A solution tert-butyl 4-(2-oxooctahydro-1H-benzimidazol-1-yl)piperidine-1-carboxylate (1 g) in dichloromethane (20 mL) was added with TFA (5 mL) and stirred at room temperature for 1 hour. The solvent was removed under reduced pressure to provide the titled compound as its TFA salt. The salt was then transformed to freebase by MP-carbonate and used without any purification. MS (M+1): 224.25

TABLE 1

Examples 2-7 were prepared via reductive amination reactions similar to Example 1, starting from corresponding cis- or trans- 1-piperidin-4-yloctahydro-2H-benzimidazol-2-one (either from the racemic or enantiomerically pure intermediates, Intermediate 1 and Intermediate 2)

| Structure (Example) | Name | Data |
| --- | --- | --- |
| (2) | Ethyl 3-{4-[(cis (+/−))-2-oxooctahydro-1H-benzimidazol-1-yl]piperidin-1-yl}pyrrolidine-1-carboxylate (mixture) | 1H NMR (400 MHz, CHLOROFORM-D): δ ppm 1.22 (t, J=7.13 Hz, 3H), 1.10-1.30 (m, 1H), 1.29-1.43 (m, 1H), 1.44-1.95 (m, 10H), 1.95-2.19 (m, 3H), 2.63-2.95 (m, 2H), 2.93-3.15 (m, 2H), 3.20-3.35 (m, 1H), 3.40-3.74 (m, 5H), 4.09 (q, J=7.10Hz, 2H), 4.13-4.20 (m, 1H), 4.20-4.35 (m, 1H). MS: 365.3 (M + 1). |
| (3) | Ethyl 3-{4-[(trans (+/−))-2-oxooctahydro-1H-benzimidazol-1-yl]piperidin-1-yl}pyrrolidine-1-carboxylate (mixture) | 1H NMR (400 MHz, CHLOROFORM-D): δ ppm 1.23 (t, J=7.03 Hz, 3H), 1.28-1.49 (m, 4H), 1.58-1.89 (m, 7H), 1.90-1.99 (m, 1H), 1.99-2.14 (m, 3H), 2.23-2.33 (m, 1H), 2.65-3.16 (m, 6H), 3.20-3.36 (m, 1H), 3.45-3.86 (m, 3H), 4.10 (q, J=7.03 Hz, 2H), 4.44-4.60 (m, 1H). MS: 365.3 (M + 1). |
| (4) | Benzyl 3-{4-[(trans (+/−))-2-oxooctahydro-1H-benzimidazol-1-yl]piperidin-1-yl}pyrrolidine-1-carboxylate (mixture) | 1H NMR (400 MHz, CHLOROFORM-D): δ ppm 1.08-1.28 (m, 1H), 1.31-1.45 (m, 1H), 1.30-1.73 (m, 10H), 1.73-1.88 (m, 3H), 1.88-2.08 (m, 2H), 2.09-2.33 (m, 2H), 3.28-3.89 (m, 6H), 4.14 (bs, 1H), 4.00-4.24 (m, 1H), 5.12 (s, 2H), 7.24-7.44 (m, 5H). MS: (M + 1) 427.2. |

TABLE 1-continued

Examples 2-7 were prepared via reductive amination reactions similar to Example 1, starting from corresponding cis- or trans- 1-piperidin-4-yloctahydro-2H-benzimidazol-2-one (either from the racemic or enantiomerically pure intermediates, Intermediate 1 and Intermediate 2)

| Structure (Example) | Name | Data |
|---|---|---|
| (5) (+/−) | Benzyl 4-[-[(trans (+/−))-2-oxooctahydro-1H-benzimidazol-1-yl]-1,4'-bipiperidine-1'-carboxylate | 1H NMR (400 MHz, CHLOROFORM-D): δ ppm 1.07-1.26 (m, 1H), 1.29-1.47 (m, 3H), 1.46-1.92 (m, 12H), 2.15-2.33 (m, 2H), 2.35-2.49 (m, 1H), 2.66-2.82 (m, 2H), 2.91 (dd, J=20.41, 11.23 Hz, 2H), 3.52-3.60 (m, 2H), 3.52-3.70 (m, 1H), 4.10-4.35 (m, 2H), 4.12 (s, 1H), 5.10 (bs, 2H) 7.27-7.38 (m, 5H). MS: (M + 1) 441.3. |
| (6) | Ethyl 4-[(3aR,7aR)-2-oxooctahydro-1H-benzimidazol-1-yl]-1,4'-bipiperidine-1'-carboxylate | 1H NMR (400 MHz, METHANOL-D4): δ ppm 1.25 (t, J=7.13 Hz, 3H) 1.32-1.50 (m, 4H) 1.74-2.03 (m, 5H) 2.13 (d, J=11.72 Hz, 2H) 2.19-2.35 (m, 1H) 2.36-2.51 (m, 1H) 2.77-2.94 (m, 2H) 2.93-3.07 (m, 2H) 3.06-3.22 (m, 2H) 3.35-3.49 (m, 1H) 3.53-3.69 (m, 4H) 3.60-3.67 (m, 1H) 3.69-3.85 (m, 1H) 4.11 (q, J=7.16 Hz, 2H) 4.29 (d, J=13.28 Hz, 2H). MS: (M + 1) 379.3. |
| (7) | Ethyl 4-[(3aS,7aS)-2-oxooctahydro-1H-benzimidazol-1-yl]-1,4'-bipiperidine-1'-carboxylate | 1H NMR (400 MHz, METHANOL-D4): δ ppm 1.25 (t, J=7.13 Hz, 3H) 1.32-1.50 (m, 4H) 1.74-2.03 (m, 5H) 2.13 (d, J=11.72 Hz, 2H) 2.19-2.35 (m, 1H) 2.36-2.51 (m, 1H) 2.77-2.94 (m, 2H) 2.93-3.07 (m, 2H) 3.06-3.22 (m, 2H) 3.35-3.49 (m, 1H) 3.53-3.69 (m, 4H) 3.60-3.67 (m, 1H) 3.69-3.85 (m, 1H) 4.11 (q, J=7.16 Hz, 2H) 4.29 (d, J=13.28 Hz, 2H). MS: (M + 1) 379.3. |

Example 8

(trans (+/−))-1-{1-[1-(cyclopentylcarbonyl)pyrrolidin-3-yl]piperidin-4-yl}octahydro-2H-benzimidazol-2-one

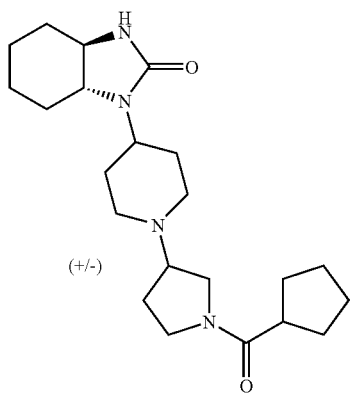

Step 1

The preparation of tert-butyl 3-{4-[(trans (+/−))-2-oxooctahydro-1H-benzimidazol-1-yl]piperidin-1-yl}pyrrolidine-1-carboxylate

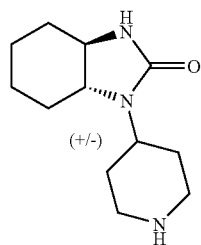

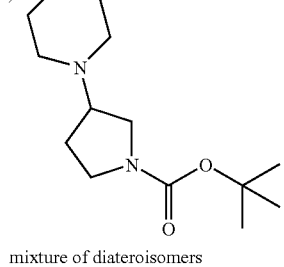

mixture of diatereoisomers

Following a similar procedure to that described in Example 1, t-Butyl 3-{4-[(trans (+/−)-2-oxooctahydro-1H-benzimidazol-1-yl]piperidin-1-yl}pyrrolidine-1-carboxylate (2.40 g) was prepared as a mixture of diastereoisomers.

Step 2

The preparation of 3-{4-[(trans (+/−))-2-oxooctahydro-1H-benzimidazol-1-yl]piperidin-1-yl}pyrrolidine

mixture of diastereoisomers

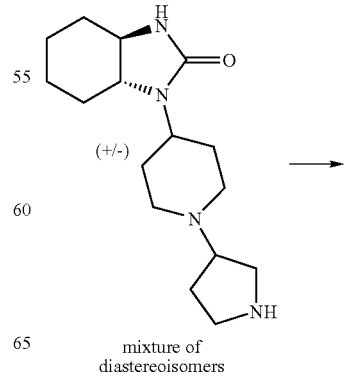

mixture of diastereoisomers

The crude intermediate (2.4 g) from Step 1 was dissolved in dichloromethane (10 mL), and TFA (5 mL) was added. The reaction mixture was stirred at room temperature overnight. Removal of solvent and excess TFA yielded the TFA salt (4.2 g) the title compound. The TFA salt was converted to its free base by MP-Carbonate, and purification on flash chromatography (MeOH/DICHLOROMETHANE) to give the title compound (0.70 g).

Step 3

The preparation of (trans (+/−))-1-{1-[1-(cyclopentylcarbonyl)pyrrolidin-3-yl]piperidin-4-yl}octahydro-2H-benzimidazol-2-one mixture of diastereoisomers

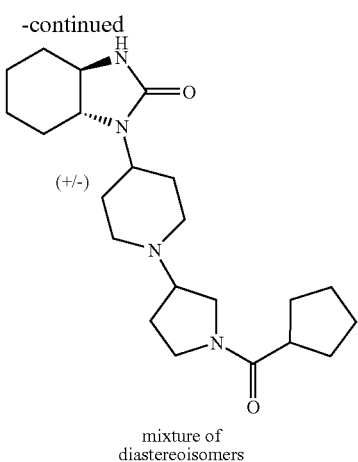

mixture of
diastereoisomers

To a solution of 3-{4-[(trans (+/−))-2-oxooctahydro-1H-benzimidazol-1-yl]piperidin-1-yl}pyrrolidine (mixture of diatereoisomers) (100 mg, 0.34 mmol) in DMF was added diisopropylethylamine (0.16 mmol), cyclopentylcarboxyl chloride (50 μL) at room temperature. The reaction was stirred at room temperature overnight and concentrated in vacuo. The residue was dissolved in dichloromethane and washed with brine. Removal of solvent gave the crude product, which was purified on high pH prep HPLC and converted to HCl salt to afford the title compound as a mixture of diastereoisomers) (36 mg). 1H NMR (400 MHz, METHANOL-D4): δ ppm 1.27-1.52 (m, 4H), 1.55-2.05 (m, 13H), 2.23-2.38 (m, 3H), 2.38-2.61 (m, 2H), 2.83-3.08 (m, 3H), 3.08-3.26 (m, 2H), 3.32-3.37 (m, 1H), 3.52-4.02 (m, 6H), 3.65 (s, 1H), 4.08-4.23 (m, 1H). MS: (M+1) 389.3.

TABLE 2

Examples 9-13 were prepared similar to the procedure described in Example 8, step 3

| Structure (Example) | Name | data |
|---|---|---|
| 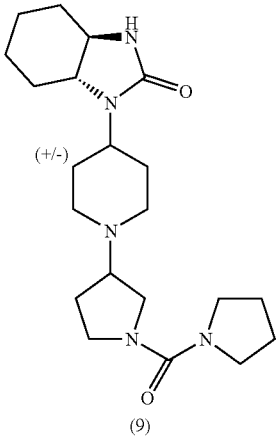 (9) | (trans (+/−))-1-{1-[1-(pyrrolidin-1-ylcarbonyl)pyrrolidin-3-yl]piperidin-4-yl}octahydro-2H-benzimidazol-2-one (mixture of diastereoisomers) | 1H NMR (400 MHz, METHANOL-D4): δ ppm 1.28-1.50 (m, 4H) 1.68-2.06 (m, 10H) 2.11-2.35 (m, 3H) 2.36-2.53 (m, 2H) 2.92-3.08 (m, 2H) 3.12-3.25 (m, 2H) 3.32-3.75 (m, 12H) 3.65 (s, 1H) 3.76-3.91 (m, 3H). MS: (M + 1). |
| 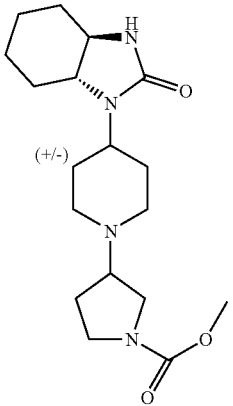 (10) | methyl 3-{4-[(trans (+/−))-2-oxooctahydro-1H-benzimidazol-1-yl]piperidin-1-yl}pyrrolidine-1-carboxylate (mixture of diastereoisomers) | 1H NMR (400 MHz, METHANOL-D4) HCl salt: δ ppm 1.29-1.52 (m, 4H), 1.58-2.07 (m, 8H), 2.10-2.35 (m, 4H), 2.87-3.06 (m, 4H), 3.07-3.21 (m, 2H), 3.23-3.40 (m, 1H), 3.57 (t, J=9.77 Hz, 1H), 3.59-3.75 (m 2H), 3.67 (s, 3H). MS: (M + 1). |

TABLE 2-continued

Examples 9-13 were prepared similar to the procedure described in Example 8, step 3

| Structure (Example) | Name | data |
|---|---|---|
| 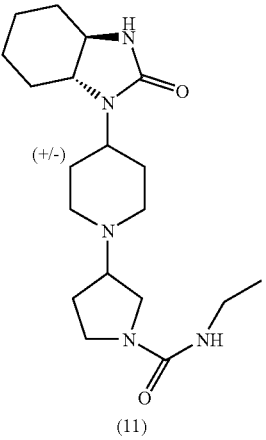 (11) | N-ethyl-3-[4-[(-[(trans (+/−))-(2-oxooctahydro-1H-benzimidazol-1-yl)piperidin-1-yl]pyrrolidine-1-carboxamide (mixture of diastereoisomers) | 1H NMR (400 MHz, METHANOL-D4): δ ppm 1.13 (t, J=7.13 Hz, 3H), 1.31-1.52 (m, 4H), 1.73-2.06 (m, 5H), 2.24-2.41 (m, 3H), 2.40-2.57 (m, 2H), 2.93-3.10 (m, 2H), 3.12-3.28 (m, 2H), 3.22 (q, J=7.23 Hz, 2H), 3.33-3.46 (m, 1H), 3.50-3.77 (m, 5H), 3.77-4.03 (m, 3H). MS: (M + 1) 364.3. |
| 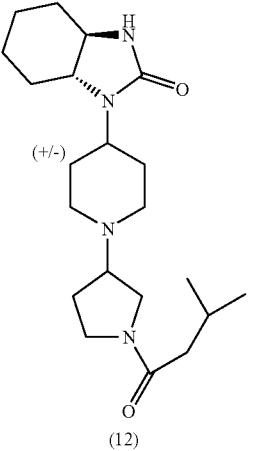 (12) | (trans (+/−))-1-{1-[1-(3-methylbutanoyl)pyrrolidin-3-yl]piperidin-4-yl}octahydro-2H-benzimidazol-2-one (mixture of diastereoisomers) | 1H NMR (400 MHz, METHANOL-D4) HCl salt: δ ppm 0.87-1.03 (m, 6H), 1.25-1.51 (m, 4H), 1.69-2.04 (m, 5H), 2.02-2.18 (m, 1H), 2.17-2.40 (m, 5H), 2.38-2.58 (m, 2H), 2.89-3.07 (m, 2H), 3.08-3.25 (m, 2H), 3.34 (s, 1H), 3.51-3.92 (m, 4H), 3.65 (s, 1H), 3.93-4.14 (m, 1H). MS: (M + 1) 377.3. |
| 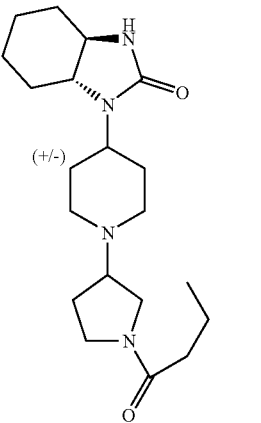 (13) | (trans (+/−))-1-[1-(1-butyrylpyrrolidin-3-yl)piperidin-4-yl]octahydro-2H-benzimidazol-2-one (mixture of diastereoisomers) | 1H NMR (400 MHz, METHANOL-D4): δ ppm 0.81-1.05 (m, 3H), 1.27-1.51 (m, 4H), 1.55-1.71 (m, 2H), 1.73-2.06 (m, 5H), 2.17-2.64 (m, 6H), 2.90-3.10 (m, 2H), 3.09-3.28 (m, 2H), 3.52-4.16 (m, 9H), 3.65 (s, 1H). MS (M + 1): 363.3. |

Example 14 and Example 15

Ethyl (3R)-3-[4-[(3aR,7aR)-2-oxo-3a,4,5,6,7,7a-hexahydro-3H-benzoimidazol-1-yl]-1-piperidyl]pyrrolidine-1-carboxylate and ethyl (3S)-3-[4-[(3aR,7aR)-2-oxo-3a,4,5,6,7,7a-hexahydro-3H-benzoimidazol-1-yl]-1-piperidyl]pyrrolidine-1-carboxylate

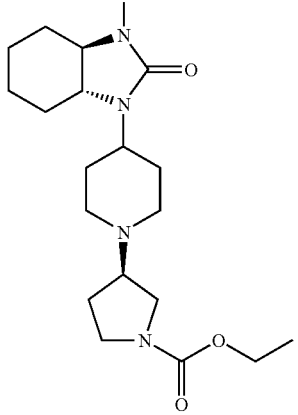

Step A

The preparation of Ethyl 3-[4-[(3aR,7aR)-2-oxo-3a,4,5,6,7,7a-hexahydro-3H-benzoimidazol-1-yl]-1-piperidyl]pyrrolidine-1-carboxylate

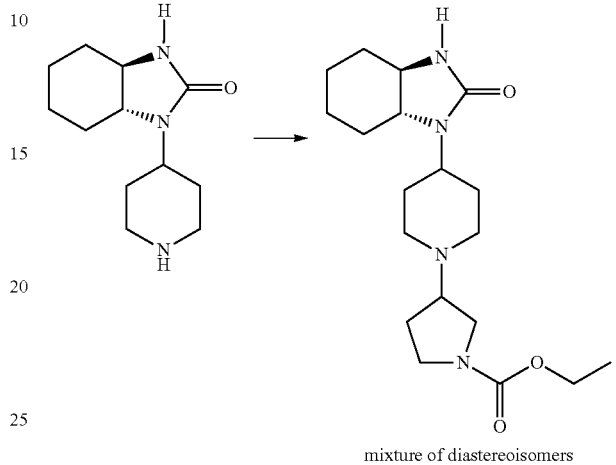

mixture of diastereoisomers

To a stirred solution of (3aR,7aR)-1-piperidin-4-yloctahydro-2H-benzimidazol-2-one TFA salt (400 mg, 1.24 mmol) in dichloromethane (10 mL) was added acetic acid (0.35 mL 6.12 mmol)-ethyl 3-oxopyrrolidine-1-carboxylate (0.35 mL 2.23 mmol). Sodium triacetoxyoborohydride (0.8 g, 3.77 mmol) was added and the mixture was stirred at room temperature overnight. The mixture was quenched with ice water, then diluted with dichloromethane (200 mL) and was washed successively with 1N NaOH (10 mL), water (10 mL) and brine. The solvent was removed under reduced pressure and the residue was purified by high pH prep LCMS (acetonitrile/water) to provide the mixture of two diastereoisomers (260 mg 58%).

Step B

Separation of Diastereoisomers

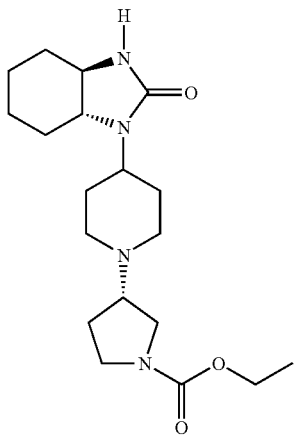

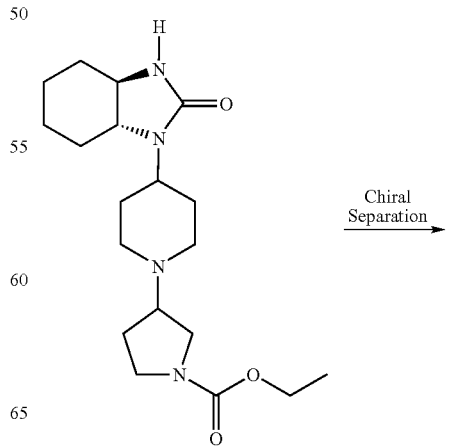

Chiral Separation

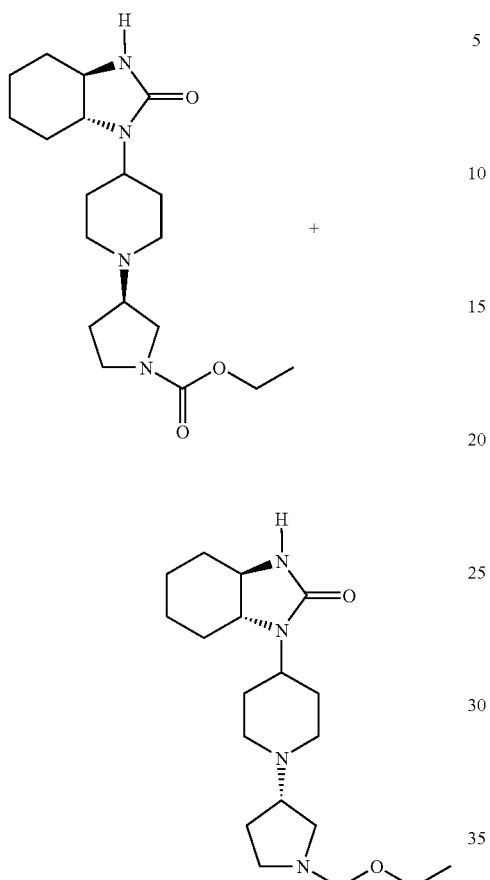

Example 16 and Example 17

Ethyl (3R)-[4-[(3aS,7aS)-2-oxo-3a,4,5,6,7,7a-hexahydro-3H-benzoimidazol-1-yl]-1-piperidyl]pyrrolidine-1-carboxylate and Ethyl (3S)-[4-[(3aS,7aS)-2-oxo-3a,4,5,6,7,7a-hexahydro-3H-benzoimidazol-1-yl]-1-piperidyl]pyrrolidine-1-carboxylate

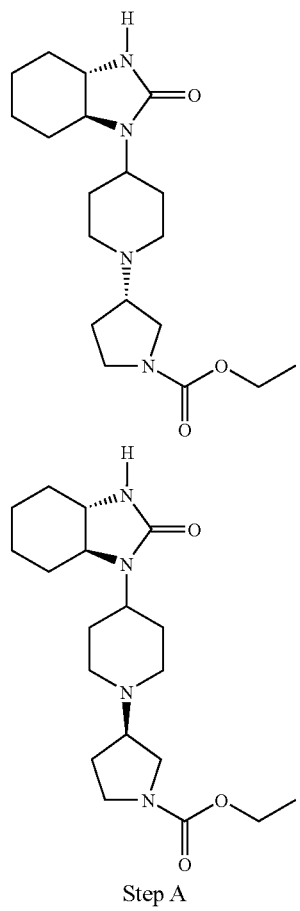

Step A

The preparation of ethyl 3-[4-[(3aS,7aS)-2-oxo-3a,4,5,6,7,7a-hexahydro-3H-benzoimidazol-1-yl]-1-piperidyl]pyrrolidine-1-carboxylate

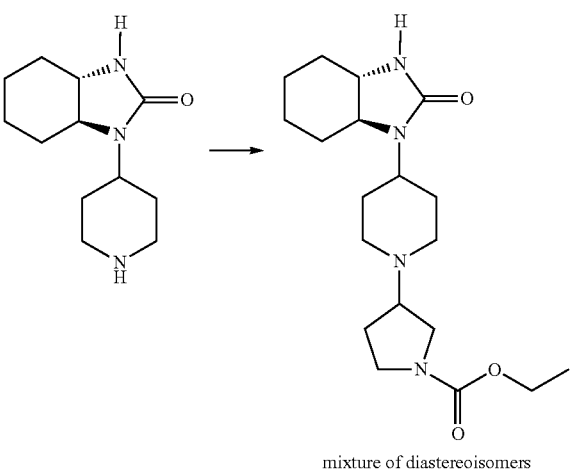

mixture of diastereoisomers

The two diastereoisomers from Step A were separated by chiral HPLC (OD column, 40% Isopropanol/60% hexane) to provided title compounds as pure enantiomers (Isomer 1 and Isomer 2).

Isomer 1 (72 mg): HPLC Retention time=6.33 min, K': 0.52 (Chiralpak OD column, 4.6×250 mm, 40% Isopropanol/60% hexane). 1H NMR (400 MHz, CHLOROFORM-D): δ ppm 1.21 (t, J=7.03 Hz, 3H), 1.26-1.46 (m, 4H), 1.52-1.86 (m, 6H), 1.93 (d, J=10.74 Hz, 1H), 1.96-2.13 (m, 4H), 2.25 (d, J=10.74 Hz, 1H), 2.60-2.80 (m, 1H), 2.80-2.91 (m, 1H), 2.90-3.03 (m, 3H), 3.06 (q, J=9.57 Hz, 1H), 3.17-3.34 (m, 1H), 3.49 (t, J=9.67 Hz, 1H), 3.52-3.64 (m, 1H), 3.63-3.81 (m, 1H), 4.08 (q, J=7.03 Hz, 2H), 4.66-4.91 (m, 1H). MS (M+1): 365.3.

Isomer 2 (32 mg): HPLC Retention time=6.99 min, K': 0.68 (Chiralpak OD column, 4.6×250 mm, 40% Isopropanol/60% hexane). 1H NMR (400 MHz, CHLOROFORM-D): δ ppm 1.21 (t, J=7.03 Hz, 3H), 1.26-1.46 (m, 4H), 1.52-1.86 (m, 6H), 1.93 (d, J=10.74 Hz, 1H), 1.96-2.13 (m, 4H), 2.25 (d, J=10.74 Hz, 1H), 2.60-2.80 (m, 1H), 2.80-2.91 (m, 1H), 2.90-3.03 (m, 3H), 3.06 (q, J=9.57 Hz, 1H), 3.17-3.34 (m, 1H), 3.49 (t, J=9.67 Hz, 1H), 3.52-3.64 (m, 1H), 3.63-3.81 (m, 1H), 4.08 (q, J=7.03 Hz, 2H), 4.66-4.91 (m, 1H). MS (M+1): 365.3.

Following the similar procedure of Step A of the Example 14 and Example 15, ethyl 3-[4-[(3aS,7aS)-2-oxo-3a,4,5,6,7,7a-hexahydro-3H-benzoimidazol-1-yl]-1-piperidyl]pyrrolidine-1-carboxylate was prepared as a mixture of two diastereoisomers.

Step B

Separation of Diastereoisomers

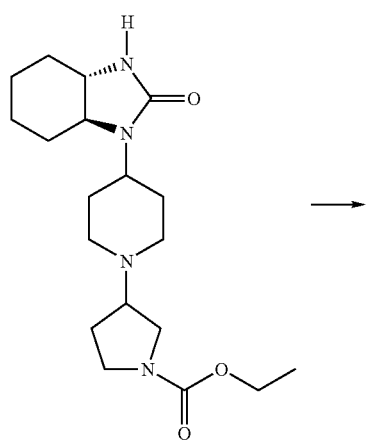

→

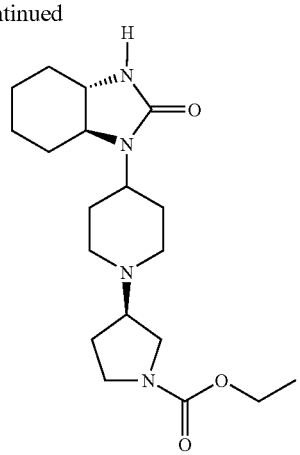

The two diastereoisomers from Step A were separated by chiral HPLC (OD column, 30% Isopropanol/70% hexane) to provided title compounds as pure enantiomers (Isomer 1 and Isomer 2).

Isomer 1: HPLC Retention time=9.05 min, K': 2.34 (Chiralpak AD column, 4.6×250 mm, 30% Isopropanol/70% hexane). 1H NMR (400 MHz, CHLOROFORM-D): δ ppm 1.21 (t, J=7.13 Hz, 3H), 1.26-1.48 (m, 4H), 1.58-1.87 (m, 7H), 1.93 (d, J=10.55 Hz, 1H), 1.99-2.13 (m, 3H), 2.25 (d, J=10.94 Hz, 1H), 2.65-2.79 (m, 1H), 2.79-2.89 (m, 1H), 2.91-3.13 (m, 4H), 3.16-3.34 (m, 1H), 3.49 (t, J=10.45 Hz, 1H), 3.53-3.64 (m, 1H), 3.65-3.83 (m, 1H), 4.08 (q, J=7.10 Hz, 2H), 4.77 (s, 1H). MS (M+1): 365.3

Isomer 2: HPLC Retention time=14.41 min, K': 1.18 (Chiralpak OD column, 4.6×250 mm, column 30% Isopropanol/70% Hexane). 1H NMR (400 MHz, CHLOROFORM-D): δ ppm 1.22 (t, J=7.13 Hz, 3H), 1.25-1.47 (m, 4H), 1.56-1.87 (m, 7H), 1.93 (d, J=10.74 Hz, 1H), 1.97-2.16 (m, 3H), 2.26 (d, J=10.74 Hz, 1H), 2.65-2.81 (m, 1H), 2.82-2.91 (m, 1H), 2.91-3.02 (m, 3H), 3.07 (q, J=9.57 Hz, 1H), 3.21-3.35 (m, 1H), 3.39-3.64 (m, 1H), 3.65-3.85 (m, 2H), 4.09 (q, J=7.10 Hz, 2H), 4.74 (s, 1H). MS (M+1): 365.3

Example 18

Tert-butyl 4-[4-[(3aS,7aS)-2-oxo-3a,4,5,6,7,7a-hexahydro-3H-benzoimidazol-1-yl]-1-piperidyl]piperidine-1-carboxylate

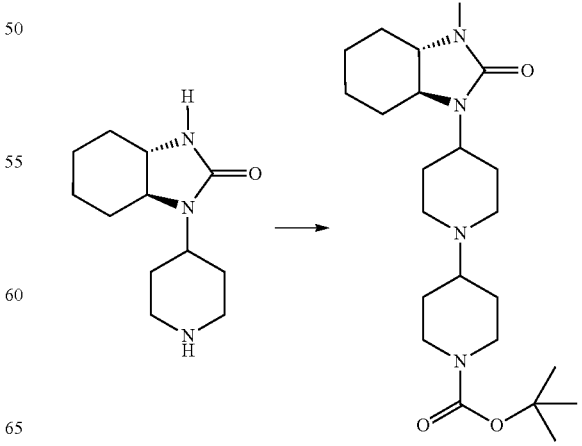

HCl salt of (3aS,7aS)-1-piperidin-4-yloctahydro-2H-benzimidazol-2-one (2 g, 7.72 mmol) was dissolved in MeOH (30 mL) and MP carbonate (12 g) was added. The mixture was stirred for one hour at rt and then filtered and concentrated in vacuo to provide a white solid. To a stirred solution of above freebase and tert-butyl 4-oxopiperidine-1-carboxylate (1.8 g, 9.04 mmol) in MeOH (40 mL) was added a solution of sodium cyanoborohydride (1 g, 14.49 mmol) and zinc chloride (0.73 g, 5.36 mmol) in MeOH (20 mL). The resulting solution was stirred at room temperature over night then concentrated in vacuo. A solution of 1N NaOH was added and aqueous phase was extracted several times with dichloromethane. The combined organic phases were washed with brine, dried and then concentrated in vacuo. The residue was purified using flash chromatography (linear gradient starting from 1-12% methanol in dichloromethane) to provide the desired compound as a white solid (2 g, 88%). 1H NMR (400 MHz, CHLOROFORM-D): δ ppm 1.21-1.49 (m, 4H), 1.41 (s, 9H), 1.57-1.67 (m, 1H), 1.66-1.84 (m, 7H), 1.93 (d, J=11.13 Hz, 1H), 2.05-2.32 (m, 5H), 2.29-2.43 (m, 1H), 2.53-2.71 (m, 2H), 2.76-3.05 (m, 4H), 3.56-3.79 (m, 1H), 3.90-4.24 (m, 2H), 4.76 (s, 1H). MS (M+1): 407.3

Example 19

(3aS,7aS)-1-[1-(4-piperidyl)-4-piperidyl]-3a,4,5,6,7,7a-hexahydro-3H-benzoimidazol-2-one

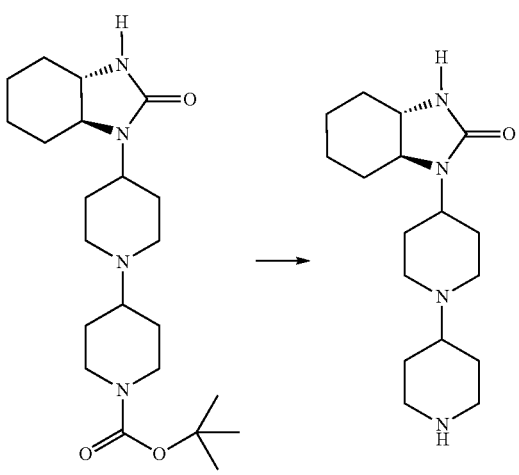

tert-butyl 4-(2-oxooctahydro-1H-benzimidazol-1-yl)-1,4'-bipiperidine-1'-carboxylate (1.2 g, 2.95 mmol) was dissolved in a mixture of 4M HCl in dioxane (15 mL) and water (5 mL). The mixture was stirred at rt for 1 hour then concentrated in vacuo to provide the title compound as a white solid (0.7 g). 1H NMR (400 MHz, CHLOROFORM-D) free base: δ ppm 1.22-1.53 (m, 5H), 1.49-1.69 (m, 1H), 1.69-1.88 (m, 7H), 1.94 (m, 1H), 2.04-2.52 (m, 6H), 2.60 (t, J=11.33 Hz, 2H), 2.82-3.09 (m, 4H), 3.17 (d, J=12.89 Hz, 2H), 3.59-3.88 (m, 1H), 4.47-4.68 (m, 1H). MS (M+1): 307.3.

Example 20

(3aS,7aS)-1-[1-[1-(cyclopropanecarbonyl)-4-piperidyl]-4-piperidyl]-3a,4,5,6,7,7a-hexahydro-3H-benzoimidazol-2-one

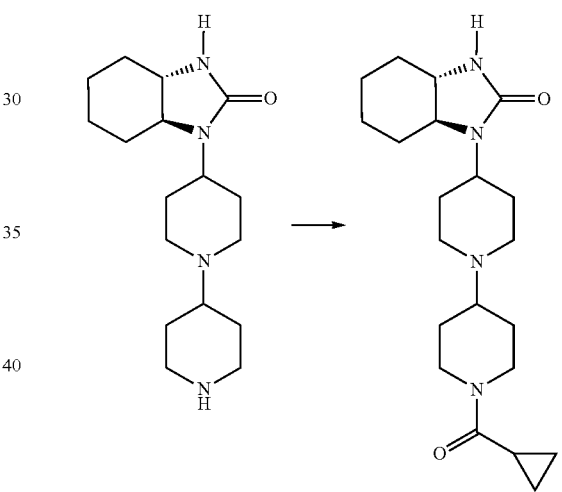

To a mixture of (3aS,7aS)-1-(1,4'-bipiperidin-4-yl)octahydro-2H-benzimidazol-2-one. 2 HCl (0.2 g, 0.53 mmol) in DMF (10 mL) was added diisopropylethylamine (0.28 mL, 1.61 mmol) and cyclopropanecarboxylic acid (0.06 mL, 0.75 mmol) at room temperature. The mixture was then sonicated to help dissolve the starting material. HATU (0.2 g, 0.53 mmol) was then added, and the reaction was stirred at room temperature. The solvent was removed under reduced pressure. The residue was dissolved in dichloromethane (80 mL) and the mixture was washed with 1N NaOH (10 mL), brine (5 mL) and concentrated in vacuo. The crude product was purified by high pH Prep. LCMS to provide the title compound, which was converted to its HCl salt (0.15 g, 69%).

Example 21-47

Examples 21-47 Were Prepared via HATU Coupling Method Similar to Example 20 Starting from (3aS,7aS)-1-(1,4'-bipiperidin-4-yl)octahydro-2H-benzimidazol-2-one (Either in Free Base Form or Salt Form) and Corresponding Carboxylic Acid

| Structure (Example) | Name | Data |
|---|---|---|
| 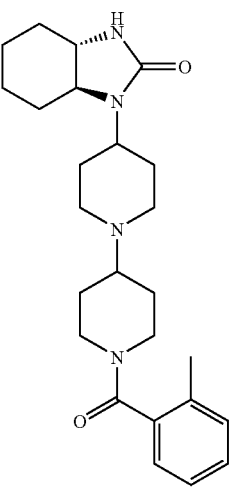 (21) | (3aS,7aS)-1-[1-[1-(2-methylbenzoyl)-4-piperidyl]-4-piperidyl]-3a,4,5,6,7,7a-hexahydro-3H-benzoimidazol-2-one | 1H NMR (400 MHz, CHLOROFORM-D): δ ppm 1.19-1.51 (m, 6H), 1.53-1.80 (m, 7H), 1.79-1.94 (m, 2H), 2.06-2.31 (m, 3H), 2.19 (s, 3H), 2.32-2.53 (m, 1H), 2.68 (t, J=12.30 Hz, 1H), 2.77-3.00 (m, 5H), 3.42 (d, J=13.87 Hz, 1H), 3.55-3.75 (m, 1H), 4.76 (d, J=12.11 Hz, 1H), 5.11 (s, 1H), 6.98-7.24 (m, 4H). MS (M + 1): 425.3 |
| 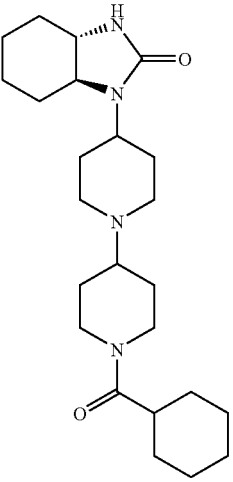 (22) | (3aS,7aS)-1-[1-[1-(cyclohexanecarbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.16-1.56 (m, 11H), 1.59-1.99 (m, 14H), 2.12-2.33 (m, 3H), 2.38-2.53 (m, 3H), 2.83-3.05 (m, 5H), 3.65-3.79 (m, 1H), 3.94 (d, J=15.43 Hz, 1H), 4.58 (s, 1H), 4.65 (d, J=13.48 Hz, 1H). MS (M + 1): 417.3. |

-continued

| Structure (Example) | Name | Data |
|---|---|---|
| (23) | (3aS,7aS)-1-[1-[1-(2-fluorobenzoyl)-4-piperidyl]-4-piperidyl]-3a,4,5,6,7,7a-hexahydro-3H-benzoimidazol-2-one | 1H NMR (400 MHz, CHLOROFORM-D): δ ppm 1.18-1.45 (m, 5H), 1.45-1.58 (m, 1H), 1.59-1.83 (m, 7H), 1.85-1.97 (m, 2H), 2.14-2.32 (m, 3H), 2.48 (t, J=11.03 Hz, 1H), 2.73 (t, J=12.21, 1H), 2.82-3.10 (m, 5H), 3.56 (d, J=13.48 Hz, 1H), 3.64-3.78 (m, 1H), 4.64-4.87 (m, 2H), 6.93-7.10 (m, 1H), 7.11-7.21 (m, 1H), 7.27-7.43 (m, 2H). MS (M + 1): 429.3 |
| (24) | (3aS,7aS)-1-[1-[1-(4-methoxybenzoyl)-4-piperidyl]-4-piperidyl]-3a,4,5,6,7,7a-hexahydro-3H-benzoimidazol-2-one | 1H NMR (400 MHz, METHANOL-D4): δ ppm 1.24-1.57 (m, 5H), 1.57-2.04 (m, 11H), 2.19-2.42 (m, 3H), 2.65 (t, J=11.52 Hz, 1H), 2.80-3.18 (m, 7H), 3.55-3.71 (m, 1H), 3.82 (s, 3H), 4.53-4.72 (m, 1H), 6.98 (d, J=7.42 Hz, 2H), 7.37 (d, J=7.42 Hz, 2H). MS (M + 1): 441.3. |
| (25) | (3aS,7aS)-1-[1-[1-(3-methylfuran-2-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.17-1.56 (m, 5H), 1.56-1.88 (m, 9H), 1.92 (d, J=10.55 Hz, 1H), 2.19 (s, 3H), 2.19-2.34 (m, 3H), 2.41-2.56 (m, 1H), 2.60-3.02 (m, 7H), 3.60-3.77 (m, 1H), 4.15-4.63 (m, 1H), 4.89 (s, 1H), 6.26 (s, 1H), 7.24-7.35 (m, 1H). MS (M + 1): 415.3 |

| Structure (Example) | Name | Data |
|---|---|---|
| 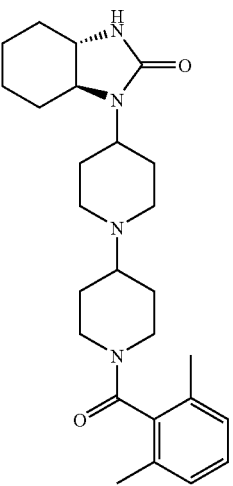<br>(26) | (3aS,7aS)-1-[1-[1-(2,6-dimethylbenzoyl)-4-piperidyl]4-piperidyl]-3a,4,5,6,7,7a-hexahydro-3H-benzoimidazol-2-one | 1H NMR (400 MHz, METHANOL-D4)-HCl salt: δ 1.27-1.57 (m, 6H), 1.56-1.67 (m, 1H), 1.67-1.75 (m, 1H), 1.74-2.02 (m, 6H), 2.06 (d, J=12.50 Hz, 1H), 2.17 (s, 3H), 2.21-2.36 (m,3H), 2.28 (s, 3H), 2.55-2.66 (m, 1H), 2.77-2.90 (m, 1H), 2.88-3.14 (m, 5H), 3.36-3.46 (m, 1H), 3.54-3.71 (m, 1H), 4.81 (d, J=15.23 Hz, 1H), 6.96-7.14 (m, 2H), 7.13-7.24 (m, 1H). MS (M + 1): 439.1. |
| 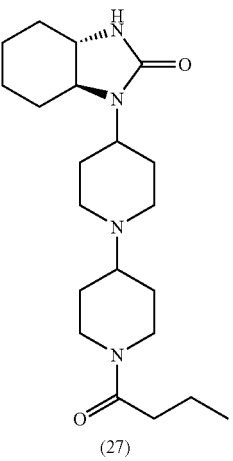<br>(27) | (3aS,7aS)-1-[1-(1-butanoyl-4-piperidyl)-4-piperidyl]-3a,4,5,6,7,7a-hexahydro-3H-benzoimidazol-2-one | 1H NMR (400 MHz, CHLOROFORM-D): δ ppm 0.94 (t, J=7.32 Hz, 3H), 1.24-1.49 (m, 6H), 1.52-1.68 (m, 3H), 1.68-1.86 (m, 7H), 1.94 (d, J=10.94 Hz, 1H), 2.14-2.35 (m, 5H), 2.39-2.56 (m, 2H), 2.82-3.05 (m, 5H), 3.62-3.78 (m, 1H), 3.88 (d, J=13.28 Hz, 1H), 4.61 (m, 2H). MS (M + 1): 377.3. |
| 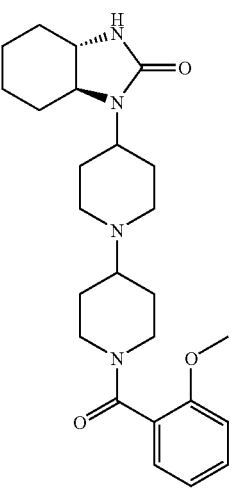<br>(28) | (3aS,7aS)-1-[1-[1-(2-methoxybenzoyl)-4-piperidyl]-4-piperidyl]-3a,4,5,6,7,7a-hexahydro-3H-benzoimidazol-2-one | 1H NMR (400 MHz, CHLOROFORM-D):<br>δ ppm 1.17-1.57 (m, 5H), 1.56-2.02 (m, 9H), 2.11-2.34 (m, 3H), 2.41-2.53 (m, 1H), 2.59-2.78 (m, 1H) 2.77-3.07 (m, 5H), 3.32-3.44 (m, 1H), 3.49 (d, J=13.48 Hz, 1H), 3.59-3.75 (m, 1H), 3.78 (d, J=7.62 Hz, 3H), 4.69-4.88 (m, 2H), 6.87 (d, J=8.40 Hz, 1H), 6.91-6.98 (m, 1H), 7.17 (d, J=16.70 Hz, 1H), 7.26-7.36 (m, 1H). MS (M + 1): 441.1. |

| Structure (Example) | Name | Data |
|---|---|---|
| 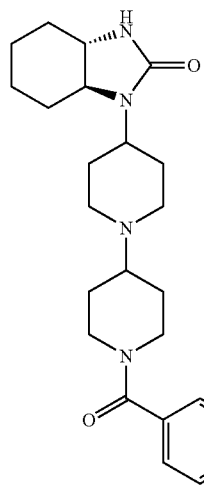<br>(29) | (3aS,7aS)-1-[1-[1-(3-methoxybenzoyl)-4-piperidyl]-4-piperidyl]-3a,4,5,6,7,7a-hexahydro-3H-benzoimidazol-2-one | 1H NMR (400 MHz, CHLOROFORM-D):<br>δ ppm 1.26-1.58 (m, 5H), 1.58-2.01 (m, 9H), 2.11-2.35 (m, 3H), 2.42-2.56 (m, 1H), 2.63-2.83 (m, 1H), 2.86-3.09 (m, 5H), 3.63-3.95 (m, 3H), 3.80 (s, 3H), 4.47-4.64 (m, 1H), 4.66-4.83 (m, 1H), 6.83-7.00 (m, 3H), 7.18-7.34 (m, 1H).<br>MS (M + 1): 441.3 |
| 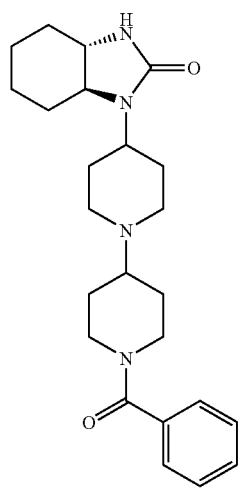<br>(30) | (3aS,7aS)-1-[1-(1-benzoyl-4-piperidyl]-4-piperidyl]-3a,4,5,6,7,7a-hexahydro-3H-benzoimidazol-2-one | HCl salt-1H NMR (400 MHz, METHANOL-D4): δ ppm 1.28-1.57 (m, 5H), 1.62-1.89 (m, 4H), 1.89-2.13 (m, 4H), 2.13-2.34 (m, 3H), 2.35-2.53 (m, 1H), 2.84-3.09 (m, 3H), 3.09-3.25 (m, 3H), 3.47-3.70 (m, 4H), 3.69-3.83 (m, 1H), 3.84-3.99 (m, 1H), 7.27-7.58 (m, 5H).<br>MS (M + 1): 411.2. |
| 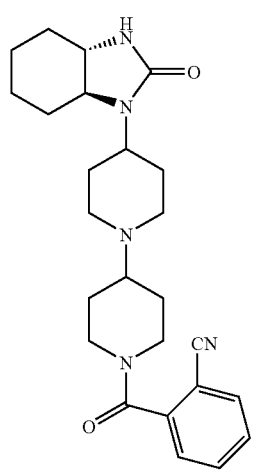<br>(31) | 2-[4-[4-[(3aS,7aS)-2-oxo-3a,4,5,6,7,7a-hexahydro-3H-benzoimidazol-1-yl]-1-piperidyl]piperidine-1-carbonyl]benzonitrile | HCl salt-1H NMR (400 MHz, METHANOL-D4): δ ppm 1.30-1.54 (m, 5H), 1.71-2.04 (m, 7H), 2.05-2.47 (m, 5H), 2.78-3.21 (m, 6H), 3.40-3.68 (m, 4H), 3.67-3.85 (m, 1H), 7.43-7.98 (m, 4H).<br>MS (M + 1): 436.3 |

| Structure (Example) | Name | Data |
|---|---|---|
| 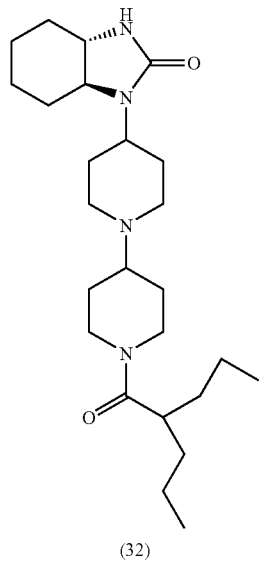<br>(32) | (3aS,7aS)-1-[1-[1-(2-propylpentanoyl)-4-piperidyl]-4-piperidyl]-3a,4,5,6,7,7a-hexahydro-3H-benzoimidazol-2-one | 1H NMR (400 MHz, METHANOL-D4): δ ppm 0.80-1.00 (m, 6H), 1.11-1.35 (m, 4H), 1.32-1.48 (m, 6H), 1.48-1.67 (m, 5H), 1.75-1.89 (m, 2H), 1.89-2.08 (m, 3H), 2.13-2.33 (m, 4H), 2.33-2.52 (m, 1H), 2.64 (t, J=12.30 Hz, 1H), 2.78-2.93 (m, 1H), 2.91-3.06 (m, 2H), 3.07-3.24 (m, 3H), 3.40-3.54 (m, 1H), 3.56-3.71 (m, 2H), 3.70-3.85 (m, 1H), 4.36 (d, J=13.67 Hz, 1H), 4.79 (d, J=14.06 Hz, 1H).<br>MS (M + 1): 433.5. |
| 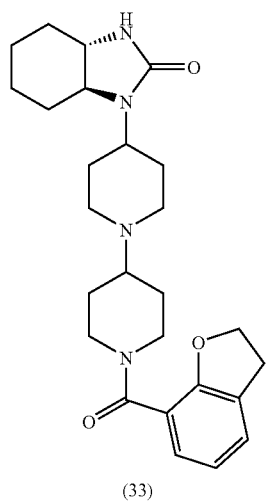<br>(33) | (3aS,7aS)-1-[1-[1-(2,3-dihydrobenzofuran-7-carbonyl]-4-piperidyl]-4-piperidyl]-3a,4,5,6,7,7a-hexahydro-3H-benzoimidazol-2-one | 1H NMR (400 MHz, METHANOL-D4): δ ppm 1.31-1.51 (m, 5H), 1.65-2.30 (m, 11H), 2.34-2.48 (m, 1H), 2.75-2.90 (m, 1H), 2.96-3.06 (m, 2H), 3.06-3.20 (m, 2H), 3.25 (t, J=8.79 Hz, 2H), 3.40-3.54 (m, 1H), 3.55-3.69 (m, 3H), 3.68-3.87 (m, 2H), 4.62 (t, J=9.37 Hz, 2H), 4.82 (d, J=12.89 Hz, 1H), 6.92 (t, J=7.62 Hz, 1H), 7.12 (d, J=7.03 Hz, 1H), 7.33 (d, J=7.42 Hz, 1H).<br>MS (M + 1): 453.3. |

| Structure (Example) | Name | Data |
|---|---|---|
| 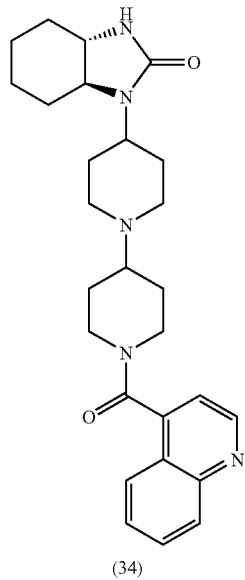<br>(34) | (3aS,7aS)-1-[1-[1-(quinoline-1-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.15-1.52 (m, 6H), 1.55-1.87 (m, 10H), 1.89-2.11 (m, 2H), 2.40-2.62 (m, 1H), 2.77-3.11 (m, 6H), 3.38 (d, J=13.28 Hz, 1H), 3.73 (s, 1H), 4.47 (s, 1H), 4.93 (t, J=11.72 Hz, 1H), 7.27-7.36 (m, 1H), 7.59 (q, J=7.81 Hz, 1H), 7.71-7.90 (m, 2H), 8.15 (d, J=7.81 Hz, 1H), 8.95 (s, 1H).<br>MS (M + 1): 462.3. |
| 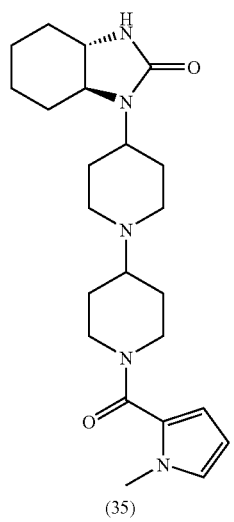<br>(35) | (3aS,7aS)-1-[1-[1-(1-methylpyrrole-2-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.25-1.55 (m, 5H), 1.57-1.72 (m, 3H), 1.72-2.00 (m, 7H), 2.12-2.36 (m, 3H), 2.53 (t, J=11.33 Hz, 1H), 2.79-3.10 (m, 6H), 3.69-3.83 (m, 1H), 3.77 (s, 3H), 4.43 (s, 1H), 4.56 (d, J=12.50 Hz, 2H), 6.04-6.10 (m, 1H), 6.28-6.36 (m, 1H), 6.68 (s, 1H).<br>MS (M + 1): 414.2. |

| Structure (Example) | Name | Data |
|---|---|---|
| 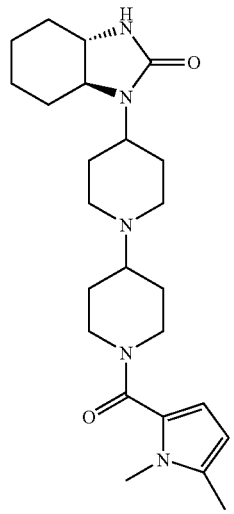<br>(36) | (3aS,7aS)-1-[1-[1-(1,5-dimethylpyrrole-2-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.11-1.57 (m, 6H), 1.62-2.01 (m, 10H), 2.23 (s, 3H), 2.31 (d, J=10.16 Hz, 2H), 2.52 (s, 1H), 2.74-3.16 (m, 6H), 3.63 (s, 3H), 3.78 (s, 1H), 4.48 (s, 1H), 4.58 (d, J=12.89 Hz, 2H), 5.85 (d, J=3.52 Hz, 1H), 6.23 (d, J=3.52 Hz, 1H).<br>MS (M + 1): 428.3. |
| 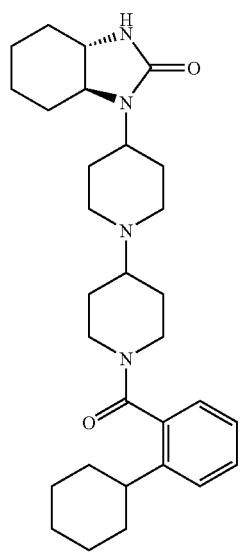<br>(37) | (3aS,7aS)-1-[1-[1-(2-cyclohexylbenzoyl)-4-piperidyl]-4-piperidyl]-3a,4,5,6,7,7a-hexahydro-3H-benzoimidazol-2-one | 1H NMR (400 MHz, METHANOL-D4): δ ppm 1.18-1.46 (m, 10H), 1.46-1.67 (m, 3H), 1.67-2.08 (m, 12H), 2.20-2.46 (m, 3H), 2.53 (t, J=10.55 Hz, 1H), 2.59-2.75 (m, 1H), 2.82 (t, J=13.28 Hz, 1H), 2.89-3.16 (m, 5H), 3.48 (t, J=12.50 Hz, 1H), 3.62 (t, J=12.11 Hz, 1H), 4.77 (t, J=13.67 Hz, 1H), 7.06 (d, J=7.03 Hz, 1H), 7.11-7.18 (m, 1H), 7.17-7.27 (m, J=7.42, 7.42 Hz, 1H), 7.31-7.41 (m, 1H).<br>MS (M + 1): 493.3. |

| Structure (Example) | Name | Data |
|---|---|---|
| 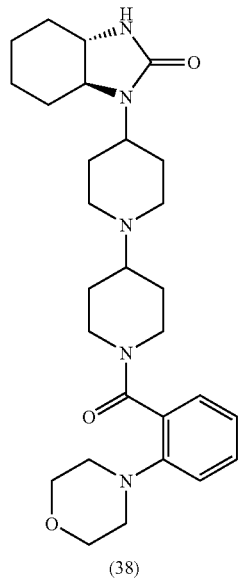<br>(38) | (3aS,7aS)-1-[1-[1-(2-morpholin-4-ylbenzoyl)-4-piperidyl]-4-piperidyl]-3a,4,5,6,7,7a-hexahydro-3H-benzoimidazol-2-one | 1H NMR (400 MHz, CHLOROFORM-D):<br>δ ppm 1.14-1.61 (m, 4H), 1.61-1.89 (m, 8H), 1.89-2.03 (m, 2H), 2.18-2.41 (m, 3H), 2.44-2.64 (m, 1H), 2.66-2.87 (m, 4H), 2.88-3.14 (m, 4H), 3.16-3.26 (m, 1H), 3.28-3.38 (m, 1H), 3.38-3.50 (m, 1H), 3.67-3.92 (m, 5H), 4.47 (s, 1H), 4.85 (t, J=11.72 Hz, 1H), 6.95-7.12 (m, 2H), 7.16-7.20 (7.26-7.30) (m, 1H), 7.35 (t, J=7.81 Hz, 1H)<br>MS (M + 1): 496.3. |
| 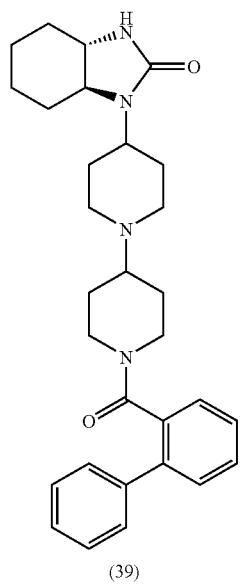<br>(39) | (3aS,7aS)-1-[1-[1-(2-phenylbenzoyl)-4-piperidyl]-4-piperidyl]-3a,4,5,6,7,7a-hexahydro-3H-benzoimidazol-2-one | 1H NMR (400 MHz, CHLOROFORM-D):<br>δ ppm 0.82-0.99 (m, 1H), 1.01-1.19 (m, 1H), 1.21-1.46 (m, 4H), 1.48-1.84 (m, 7H), 1.84-1.96 (m, 1H), 1.98-2.13 (m, 2H), 2.16-2.34 (m, 3H), 2.34-2.54 (m, 2H), 2.60 (t, J=11.91 Hz, 1H), 2.72-2.87 (m, 1H), 2.87-3.03 (m, 2H), 3.12-3.29 (m, 1H), 3.54-3.74 (m, 1H), 4.66-4.82 (m, 2H), 7.19-7.46 (m, 8H), 7.52 (d, J=7.81 Hz, 1H).<br>MS (M + 1): 487.3. |

| Structure (Example) | Name | Data |
|---|---|---|
| 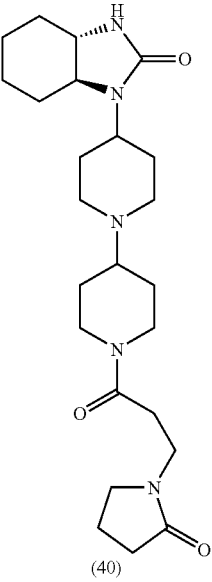<br>(40) | (3aS,7aS)-1-[1-[1-[3-(2-oxopyrrolidin-1-yl)propanoyl]-4-piperidyl]-4-piperidyl]-3a,4,5,6,7,7a-hexahydro-3H-benzoimidazol-2-one | HCl salt-1H NMR (400 MHz, METHANOL-D4): δ ppm 1.32-1.52 (m, 5H), 1.54-1.73 (m, 1H), 1.73-2.03 (m, 6H), 2.04-2.14 (m, 2H), 2.14-2.27 (m, 2H), 2.28-2.56 (m, 5H), 2.57-2.84 (m, 3H), 2.94-3.09 (m, 2H), 3.10-3.25 (m, 3H), 3.46-3.75 (m, 7H), 3.77-3.93 (m, 1H), 4.14 (d, J=13.67 Hz, 1H), 4.67 (d, J=13.28 Hz, 1H).<br>MS (M + 1): 446.3. |
| 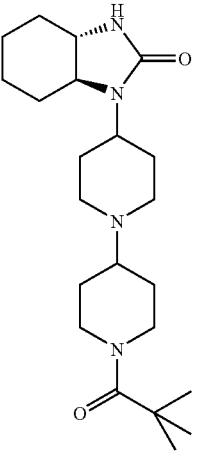<br>(41) | (3aS,7aS)-1-[1-[1-(2,2-dimethylpropanoyl)-4-piperidyl]-4-piperidyl]-3a,4,5,6,7,7a-hexahydro-3H-benzoimidazol-2-one | 1H NMR (400 MHz, METHANOL-D4): δ ppm 1.19-1.30 (m, 1H), 1.28 (s, 9H), 1.33-1.50 (m, 4H), 1.52-1.73 (m, 2H), 1.75-1.90 (m, 2H), 1.88-2.10 (m, 3H), 2.13-2.34 (m, 4H), 2.35-2.52 (m, 1H), 2.82-2.95 (m, 2H), 2.96-3.07 (m, 2H), 3.06-3.22 (m, 2H), 3.39-3.54 (m, 1H), 3.55-3.70 (m, 2H), 3.69-3.86 (m, 1H), 4.60 (d, J=11.72 Hz, 2H).<br>MS (M + 1): 391.2. |
| 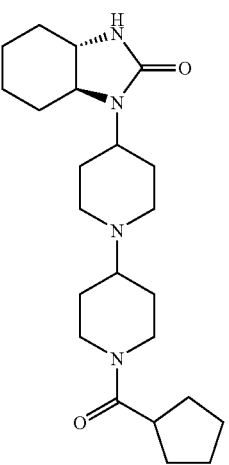<br>(42) | (3aS,7aS)-1-[1-[1-(cyclopentanecarbonyl)-4-piperidyl]-4-piperidyl]-3a,4,5,6,7,7a-hexahydro-3H-benzoimidazol-2-one | 1H NMR (400 MHz, METHANOL-D4) HCl salt: δ ppm 1.28-1.47 (m, 5H), 1.51-2.04 (m, 13H), 2.08-2.34 (m, 4H), 2.34-2.51 (m, 1H), 2.63 (t, J=12.89 Hz, 1H), 2.94-3.22 (m, 7H), 3.40-3.53 (m, 1H), 3.56-3.67 (m, 2H), 3.68-3.83 (m, 1H), 4.28 (d, J=14.06 Hz, 1H), 4.72 (d, J=15.62 Hz, 1H).<br>MS (M + 1): 403.3 |

| Structure (Example) | Name | Data |
|---|---|---|
| 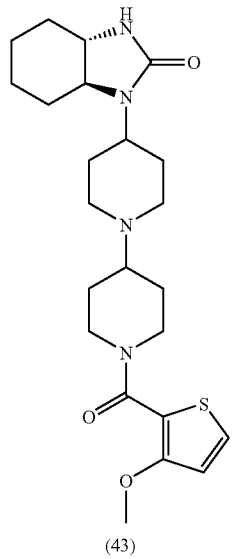<br>(43) | (3aS,7aS)-1-[1-[1-(3-methoxythiophene-2-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.27-1.57 (m, 6H), 1.61-1.71 (m, 1H), 1.69-1.89 (m, 8H), 1.94 (d, J=10.55 Hz, 1H), 2.17-2.35 (m, 3H), 2.42-2.56 (m, 1H), 2.77-3.09 (m, 6H), 3.61-3.81 (m, 1H), 3.88 (s, 1H), 6.75 (d, J=5.27 Hz, 1H), 7.30 (d, J=5.47 Hz, 1H).<br>MS (M + 1): 447.3 |
| 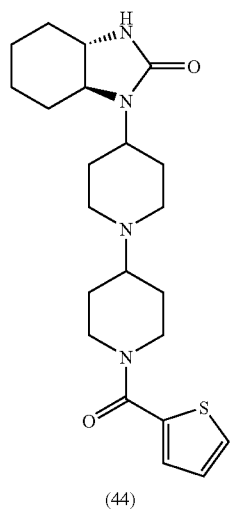<br>(44) | (3aS,7aS)-1-[1-[1-(thiophene-2-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.25-1.60 (m, 6H), 1.60-2.05 (m, 9H), 2.11-2.33 (m, 3H), 2.48-2.60 (m, 1H), 2.88-3.10 (m, 6H), 3.64-3.80 (m, 1H), 4.25-4.62 (m, 2H), 4.52 (s, 1H), 7.02 (d, J=4.98 Hz, 1H), 7.13-7.32 (m, 1H), 7.41 (d, J=5.08 Hz, 1H).<br>MS (M + 1): 417.3 |

| Structure (Example) | Name | Data |
|---|---|---|
| 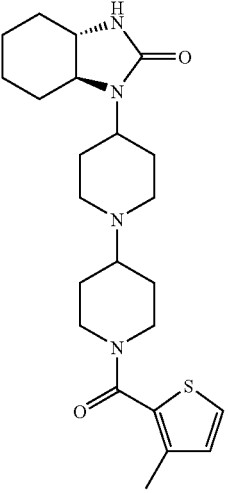 (45) | (3aS,7aS)-1-[1-[1-(3-methylthiophene-2-carbonyl)-4-piperidyl]-4-piperidyl]-3a,4,5,6,7,7a-hexahydro-3H-benzoimidazol-2-one | 1H NMR (400 MHz, CHLOROFORM-D): δ ppm 1.19-1.52 (m, 5H), 1.57-1.66 (m, 1H), 1.66-1.87 (m, 7H), 1.84-2.02 (m, 1H), 2.12-2.32 (m, 3H), 2.21 (s, 3H), 2.46 (t, J=11.13 Hz, 1H), 2.74-3.04 (m, 6H), 3.40 (s, 1H), 3.62-3,78 (m, 1H), 4.00-4.51 (m, 2H), 4.74-4.91 (m, 1H), 6.78 (d, J=5.08 Hz, 1H), 7.22 (d, J=4.69 Hz, 1H). MS (M + 1): 431.3 |
| 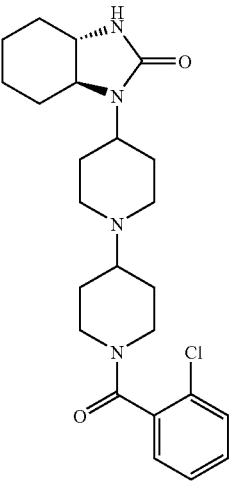 (46) | (3aS,7aS)-1-[1-[1-(2-chlorobenzoyl)-4-piperidyl]-4-piperidyl]-3a,4,5,6,7,7a-hexahydro-3H-benzoimidazol-2-one | 1H NMR (400 MHz, CHLOROFORM-D): δ ppm 1.24-1.49 (m, 4H), 1.51-1.87 (m, 7H), 1.88-2.01 (m, 2H), 2.18-2.36 (m, 3H), 2.44-2.60 (m, 1H), 2.70-2.86 (m, 1H), 2.88-3.03 (m, 5H), 3.03-3.16 (m, 1H), 3.44 (s, 1H), 3.41-3.55 (m, 1H), 3.66-3.83 (m, 1H), 4.82 (t, J=15.04 Hz, 1H), 5.04 (s, 1H), 7.19-7.36 (m, 3H), 7.37-7.46 (m, 1H). MS (M + 1): 445.3, 446.3 |
| 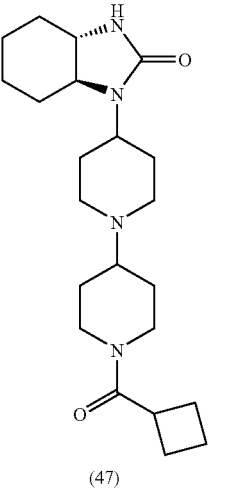 (47) | (3aS,7aS)-1-[1-[1-(cyclobutanecarbonyl)-4-piperidyl]-4-piperidyl]-3a,4,5,6,7,7a-hexahydro-3H-benzoimidazol-2-one | HCl salt-1H NMR (400 MHz, METHANOL-D4) δ ppm 1.30-1.50 (m, 5H), 1.53-1.71 (m, 2H), 1.74-2.08 (m, 6H), 2.11-2.37 (m, 6H), 2.36-2.51 (m, 1H), 2.65 (t, J=12.70 Hz, 1H), 2.93-3.20 (m, 6H), 3.36-3.53 (m, 2H), 3.53-3.70 (m, 3H), 3.70-3.89 (m, 1H), 3.97 (d, J=14.45 Hz, 1H), 4.67 (d, J=12.89 Hz, 1H). MS (M + 1): 389.2 |

Example 48

Isopropyl 4-[(3aR,7aR)-2-oxooctahydro-1H-benz-imidazol-1-yl]-1,4'-bipiperidine-1'-carboxylate

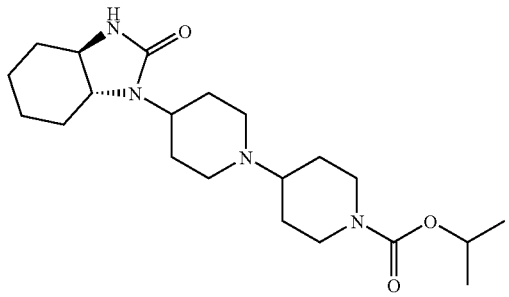

and concentrated under reduced pressure. The residue was dissolved in acetone (300 mL) and HCl (50 mL, 5N to 6N in 2-propanol) was added and was heated at reflux overnight. The mixture was concentrated in vacuo, diluted with dichloromethane (100 ml) and extracted with HCl 1N (4×100 ml). The aqueous extracts were combined and basified with NaOH pallets. The solution was then extracted with dichloromethane (3×100 mL), combined organic extracts were dried with anhydrous sodium sulphate, filtered and concentrated in vacuo to afford the titled compound (23 g, 66%) $^1$H-NMR (300 MHz, $CD_3OD$): δ 7.30 (5H, m), 5.10 (2H, s) 4.21 (2H, d, J=13.5 Hz) 2.87 (4H, t, J=6.2 Hz), 2.77-2.70 (1H, m) 2.62-2.58 (2H, m), 2.40 (2H, t, J=6.2 Hz) 1.86 (2H, d, J=12.0 Hz), 1.75 (2H, t, J=5.6 Hz) 1.42 (2H, m).

Step B

The preparation of 4-((R,R)-2-amino-cyclohexylamino)-[1,4']bipiperidinyl-1'carboxylic acid benzyl ester

Step A

The preparation of benzyl 4-oxo-1,4'-bipiperidine-1'-carboxylate

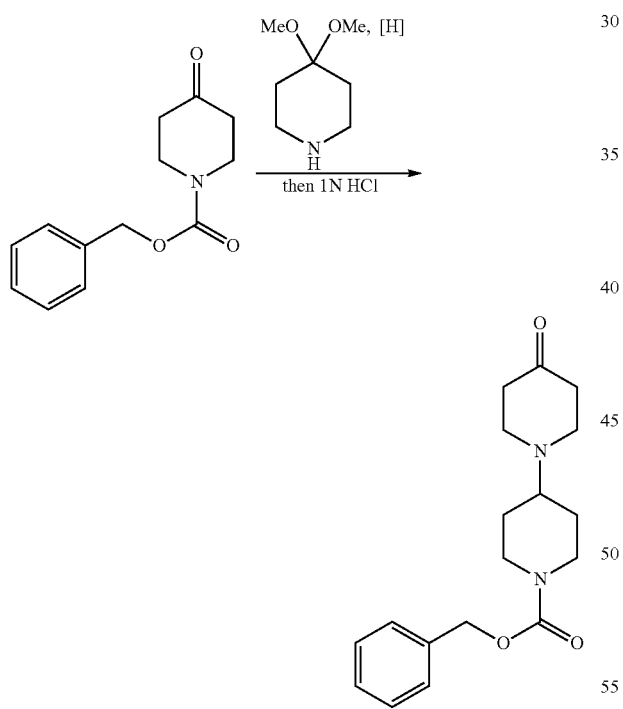

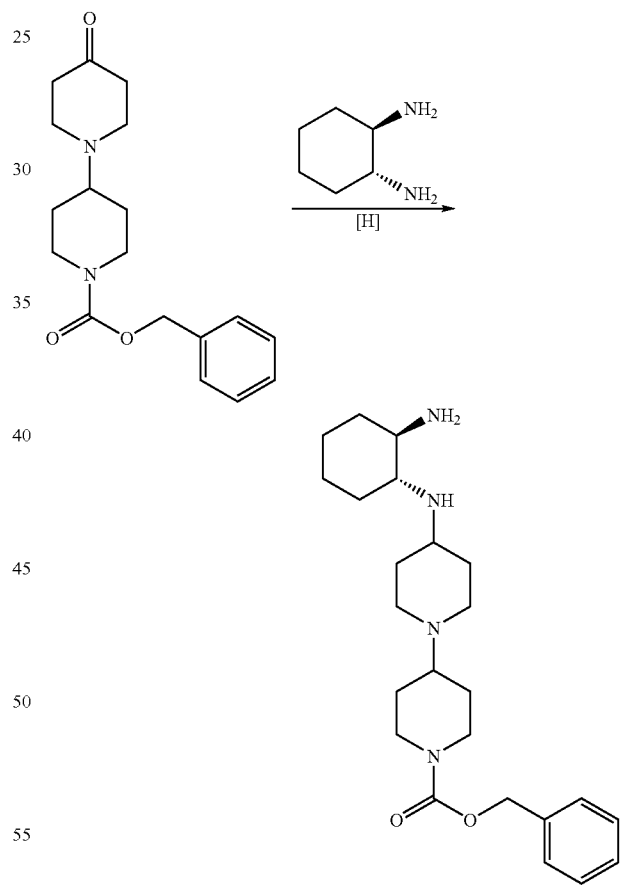

Benzyl 4-oxopiperidine-1-carboxylate (29.5 g, 126 mmol), 4,4-dimethoxypiperidine hydrochloride (20 g, 110 mmol), and trietylamine (16.9 mL, 1121 mmol) were stirred in 1,2-dichloroethane (600 mL). Sodium triacetoxyborohydride (30.4, 143 mmol) was added at 0° C. (over 30 minutes) followed by acetic acid (8.2 mL, 143 mmol) and the solution was stirred at room temperature for 24 h. 1N NaOH (100 mL) was added to the mixture and the solution was extracted with dichloromethane (3×100 mL). The combined organic extracts were dried with anhydrous sodium sulfate, filtered The (R,R)-1,2-diaminocyclohexane (7.2 g, 63.2 mmol), acetic acid (2.71 ml, 47.4 mmol), sodium triacetoxyborohydride (8.71 g, 41.1 mmol) were stirred in a mixture of 1,2-dichloroethane (125 mL). N—CBZ-piperidinylpiperidone (10.0 g, 31.6 mmol) solution in dichloromethane (125 mL) was added at 0° C. (over 3 hours) and the solution was stirred at room temperature for 3 days. A 1N NaOH solution (100 mL) was added to the mixture and was extracted with dichloromethane (3×100 mL). The combined organic extracts were dried with anhydrous sodium sulphate, filtered and concentrated under reduced pressure to give the title product (14.22 g), which was used for next step without purification.

Step C

The preparation of 4-((3aR,7aR-2-Oxo-octahydro-benzimidazol-1-yl)-[1,4']-bipiperidinyl-1'-carboxylic acid benzyl ester

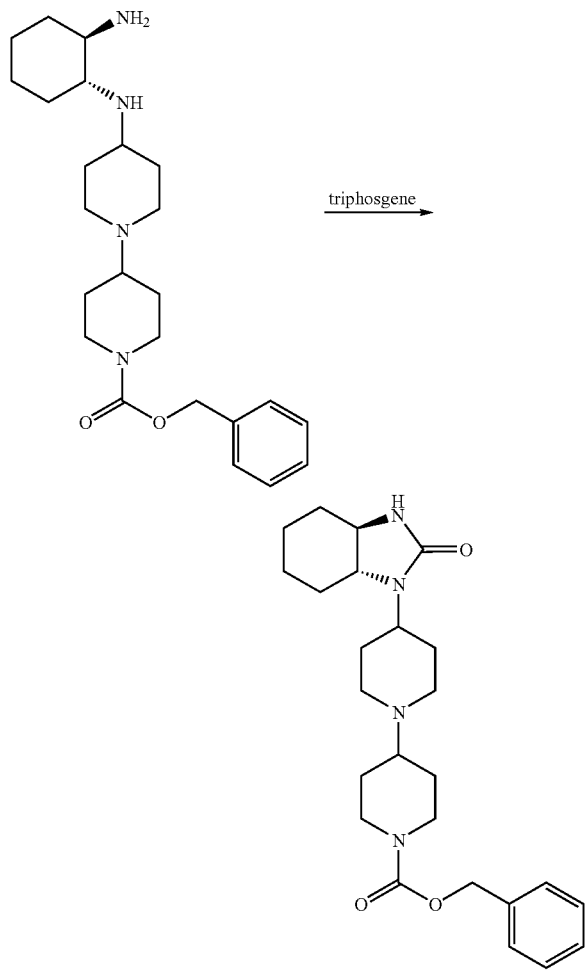

A solution of triphosgene (4.7 g, 15.8 mmol) and trietylamine (8.8 mL, 63.2 mmol) in anhydrous dichloromethane (300 mL) was added with a solution of N—CBZ-4-(R,R)-(2-oxo-octahydro-benzoimidazol-1-yl)-piperidine (5.80 g, 19.8 mmol) in dichloromethane (100 mL) dropwise and was stirred at room temperature for 24 h. A 5% aqueous sodium bicarbonate (100 mL) was added to the mixture, the layers were separated and the aqueous layer was extracted with dichloromethane (3×100 mL). The combined organic portions were washed with 5% aqueous sodium bicarbonate (100 mL), dried with anhydrous sodium sulphate, filtered, and concentrated in vacuo. The residue was purified by flash-chromatography using 0-40% methanol in AcOEt and was further purified by recrystallization in acetonitrile to provide the titled compound (2.05 g, 14% in 2 steps), $^{1}$H-NMR (300 MHz, CD$_3$OD): δ 7.3 (5H, m), 5.1 (2H, s) 4.77 (1H, m) 4.21 (2H, m) 3.72 (1H, m) 2.96 (4H, m), 2.74 (2H, t, J=11.4 Hz) 2.41 (1H, t, J=11.2 Hz) 2.17-2.29 (3H, m), 1.92-1.98 (1H, m) 1.62-1.77 (8H, m), 1.30-1.41 (6H, m). $^{13}$C-NMR (75 MHz, CD$_3$OD): δ 163.9, 155.4, 137.1, 128.7, 128.2, 128.1, 67.3, 62.3, 62.1, 58.9, 51.3, 49.4, 49.1, 43.9, 32.4, 30.7, 29.8, 29.0, 28.4, 28.2, 24.4, 24.0

Step D

The preparation of (3aR,7aR)-1-(1,4'-bipiperidin-4-yl)octahydro-2H-benzimidazol-2-one

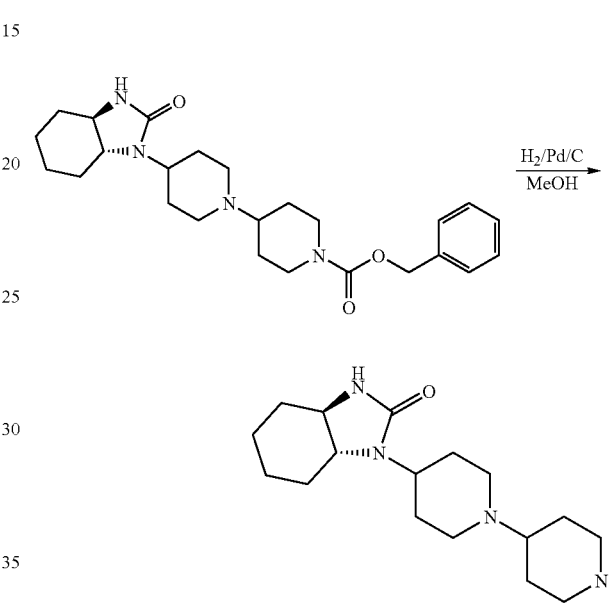

To a solution of benzyl 4-[(3aR,7aR)-2-oxooctahydro-1H-benzimidazol-1-yl]-1,4'-bipiperidine-1'-carboxylate-(880 mg, 2.0 mmol) in methanol (25 mL) was added 10% Pd/C (0.1 g), the mixture was hydrogenated at 40 psi for 12 h. Filtration of catalyst and concentration of solvents afforded crude product (600 mg, 98%), which was used for the next step without further purification. MS (M+1): 307.31

Step E

The preparation of isopropyl 4-[(3aR,7aR)-2-oxooctahydro-1H-benzimidazol-1-yl]-1,4'-bipiperidine-1'-carboxylate

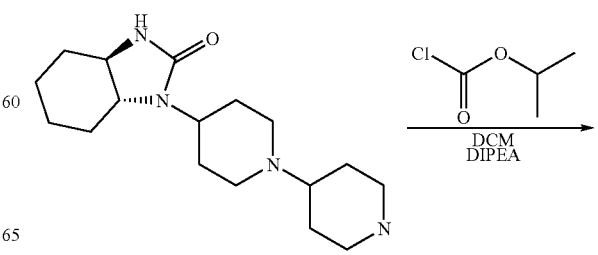

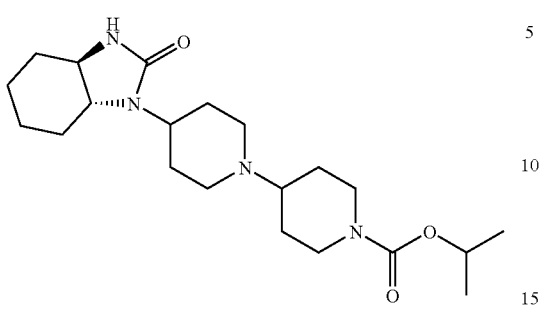

The crude product from step A ((3aR,7aR)-1-(1,4'-bipiperidin-4-yl)octahydro-2H-benzimidazol-2-one, 0.25 mmol) was dissolved in dry dichloromethane (5 mL), and cooled to −20° C. A solution of 0.1N isopropyl chloroformate in dichloromethane (2.2 mL, 0.9 eq.) was added drop wise and the reaction mixture was stirred at −20° C. for 10 min. Saturated NaHCO$_3$ (5 ml) was added followed by dichloromethane (20 mL), the phases were separated and the aqueous was extracted with dichloromethane (2×10 ml). The combined organic phases were washed with brine, dried over Na$_2$SO$_4$, filtered, and concentrated in vacuo. The crude produced was purified with high pH prep-LCMS to give the title compound (42 mg, 43%). 1H NMR (400 MHz, METHANOL-D4): δ ppm 1.21 (d, J=6.25 Hz, 6H), 1.30-1.49 (m, 6H), 1.53-1.73 (m, 2H), 1.74-2.04 (m, 7H), 2.17-2.37 (m, 3H), 2.43-2.57 (m, 1H), 2.64-2.85 (m, 2H), 2.87-3.11 (m, 4H), 3.50-3.73 (m, 1H), 4.10-4.21 (m, 2H), 4.74-4.84 (m, 1H). MS (M+1): 393.2

Example 49

(3aR,7aR)-1-[1'-(cyclopropylcarbonyl)-1,4'-bipiperidin-4-yl]octahydro-2H-benzimidazol-2-one

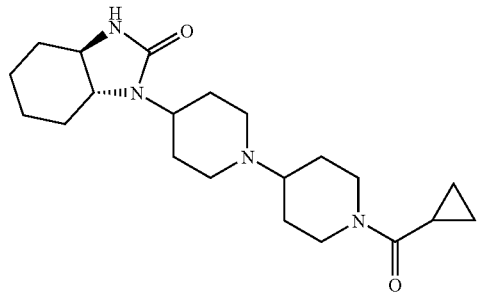

To the solution of (3aR,7aR)-1-(1,4'-bipiperidin-4-yl)octahydro-2H-benzimidazol-2-one, 0.25 mmol) in dry DMF (3 mL) was added cyclopropanecarboxylic acid (26 mg, 0.3 mmol) followed by HATU (114 mg, 0.3 mmol) and diisopropylethylamine (0.10 mL, 0.5 mmol) and the mixture was stirred at room temperature for 1 h. The reaction was quenched with water (5 mL) and the solvent was removed in vacuo. Dichloromethane (15 mL) was added and washed with saturated NaHCO$_3$ (10 mL) and brine (10 mL) and dried over Na$_2$SO$_4$. The crude product was purified with high pH prep-LCMS to provide the title compound (48 mg, 51%) as white powder. 1H NMR (400 MHz, METHANOL-D4): δ ppm 0.61-0.81 (m, 4H), 1.16-1.43 (m, 6H), 1.50-1.67 (m, 2H), 1.68-1.98 (m, 8H), 2.13-2.29 (m, 3H), 2.44-2.62 (m, 2H), 2.80-3.10 (m, 5H), 3.48-3.66 (m, 1H), 4.31 (d, J=13.28 Hz, 1H), 4.47 (d, J=13.28 Hz, 1H). MS (M+1): 375.2

Example 50

(3aR,7aR)-1-[1'-(propylcarbonyl)-1,4'-bipiperidin-4-yl]octahydro-2H-benzimidazol-2-one

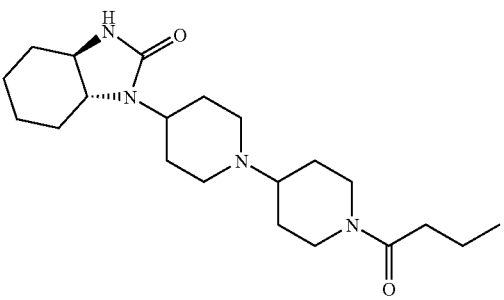

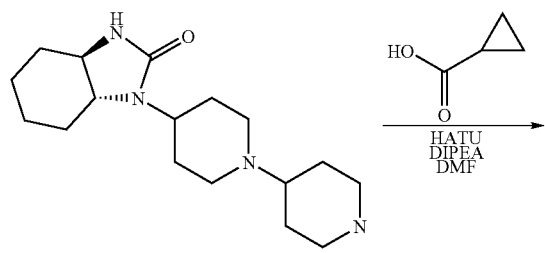

To the solution of (3aR,7aR)-1-(1,4'-bipiperidin-4-yl)octahydro-2H-benzimidazol-2-one, 0.25 mmol) in dry DMF (3 mL) was added butyric acid (26 mg, 0.3 mmol) followed by HATU (114 mg, 0.3 mmol) and diisopropylethylamine (0.10 mL, 0.5 mmol) and the mixture was stirred at room temperature for 1 h. The reaction was quenched with water (5 mL) and the solvent was removed in vacuo. Dichloromethane (15 mL) was added and washed with saturated NaHCO$_3$ (10 mL) and brine (10 mL), and dried over Na$_2$SO$_4$. The crude product was purified with high pH prep-LCMS to to provide the title compound (53 mg, 56%) as white powder. 1H NMR (400 MHz, METHANOL-D4): δ ppm 0.94 (t, J=7.42 Hz, 3H), 1.25-1.48 (m, 6H), 1.51-1.65 (m, 3H), 1.68 (d, J=11.72 Hz, 1H), 1.74-2.01 (m, 7H), 2.19-2.32 (m, 3H), 2.35 (t, J=7.62 Hz, 2H), 2.55 (t, J=12.11 Hz, 2H), 2.89-3.11 (m, 5H), 3.56-3.69 (m, 1H), 4.01 (d, J=13.28 Hz, 1H), 4.57 (d, J=13.28 Hz, 1H). MS (M+1): 377.2

Example 51

(3aR,7aR)-1-[1'-(cyclopentylcarbonyl)-1,4'-bipiperidin-4-yl]octahydro-2H-benzimidazol-2-one

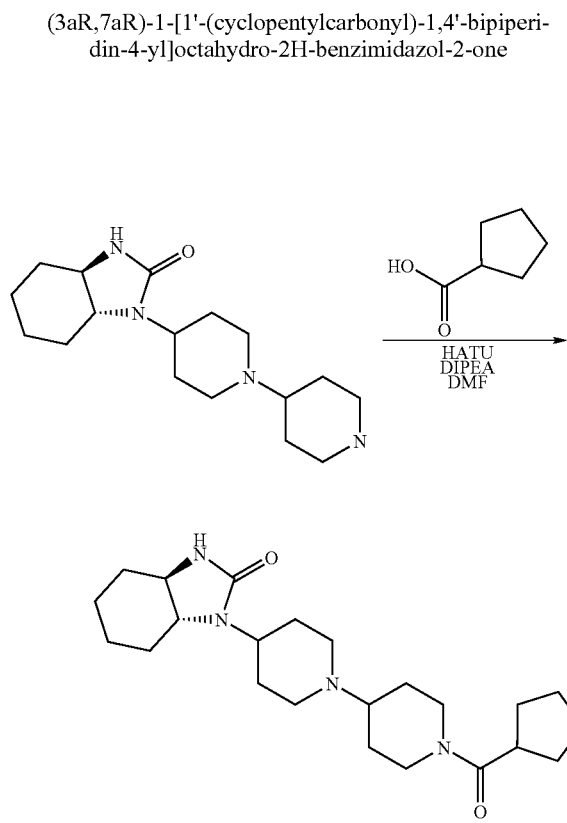

To the solution of (3aR,7aR)-1-(1,4'-bipiperidin-4-yl)octahydro-2H-benzimidazol-2-one, 0.25 mmol) in dry DMF (3 mL) was added cyclopentanecarboxylic acid (34 mg, 0.3 mmol) followed by HATU (114 mg, 0.3 mmol) and diisopropylethylamine (0.10 mL, 0.5 mmol) and the mixture was stirred at room temperature for 1 h. The reaction was quenched with water (5 mL) and the solvent was removed in vacuo. Dichloromethane (15 mL) was added and washed with saturated NaHCO$_3$ (10 mL) and brine (10 mL) and dried over Na$_2$SO$_4$. The crude product was purified with high pH prep-LCMS to yield (3aR,7aR)-1-[1'-(cyclopentylcarbonyl)-1,4'-bipiperidin-4-yl]octahydro-2H-benzimidazol-2-one (64 mg, 63%) as white powder. 1H NMR (400 MHz, METHANOL-D4): δ ppm 1.25-1.49 (m, 6H), 1.53-1.73 (m, 8H), 1.76-2.03 (m, 9H), 2.18-2.36 (m, 3H), 2.51-2.62 (m, 2H), 2.91-3.11 (m, 6H), 3.56-3.68 (m, 1H), 4.13 (d, J=13.28 Hz, 1H), 4.58 (d, J=13.28 Hz, 1H). MS (M+1): 403.3

Example 52

(3aR,7aR)-1-{1'-[3-(2-oxopyrrolidin-1-yl)propanoyl]-1,4'-bipiperidin-4-yl}octahydro-2H-benzimidazol-2-one

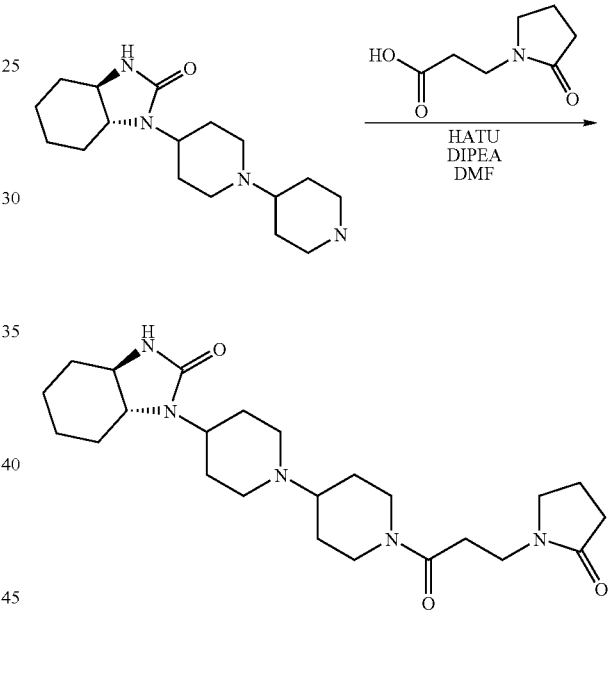

To the solution of (3aR,7aR)-1-(1,4'-bipiperidin-4-yl)octahydro-2H-benzimidazol-2-one (0.25 mmol) in dry DMF (3 mL) was added 3-(2-oxopyrrolidin-1-yl)propanoic acid (47 mg, 0.3 mmol) followed by HATU (114 mg, 0.3 mmol) and diisopropylethylamine (0.10 mL, 0.5 mmol). The mixture was stirred at room temperature for 1 h, and the reaction was quenched with water (5 mL) and the solvent was removed in vacuo. Dichloromethane (15 mL) was added and washed with saturated NaHCO$_3$ (10 mL) and brine (10 mL) and dried over Na$_2$SO$_4$. The crude product was purified with High pH prep-LCMS to provide the title compound (53 mg, 47%) as white powders. 1H NMR (400 MHz, METHANOL-D4): δ ppm 1.26-1.51 (m, 6H), 1.55-1.73 (m, 2H), 1.75-2.08 (m, 9H), 2.19-2.37 (m, 5H), 2.56 (t, J=11.91 Hz, 2H), 2.64 (t, J=7.03 Hz, 2H), 2.87-3.14 (m, 5H), 3.43-3.55 (m, 4H), 3.55-3.69 (m, 1H), 3.99 (d, J=13.28 Hz, 1H), 4.54 (d, J=13.28 Hz, 1H). MS (M+1): 446.3

Example 53-57

The Examples in the Following Table was Prepared from (3aR,7aR)-1-(1,4'-bipiperidin-4-yl)octahydro-2H-benzimidazol-2-one or Its Salt and Corresponding Acid Following the Similar Procedure Described in Example 52

| Structure (Example) | Name | Data |
|---|---|---|
| (53) | (3aR,7aR)-1-[1-(1-benzoyl-4-piperidyl)-4-piperidyl]-3a,4,5,6,7,7a-hexahydro-3H-benzoimidazol-2-one | 1H NMR (400 MHz, CHLOROFORM-D): δ ppm 1.25-1.61 (m, 5H), 1.62-1.99 (m, 10H), 2.15-2.35 (m, 3H), 2.44-2.59 (m, 1H), 2.65-2.84 (m, 1H), 2.87-3.08 (m, 5H), 3.53-3.95 (m, 2H), 4.51 (s, 1H), 4.61-4.87 (m, 1H), 7.30-7.50 (m, 5H). MS (M + 1): 411.2 |
| (54) | (3aR,7aR)-1-[1-[1-(2-methylbenzoyl)-4-piperidyl]-4-piperidyl]-3a,4,5,6,7,7a-hexahydro-3H-benzoimidazol-2-one | 1H NMR (400 MHz, CHLOROFORM-D): δ ppm 1.21-1.58 (m, 6H), 1.58-1.86 (m, 7H), 1.87-1.99 (m, 2H), 2.07-2.37 (m, 3H), 2.24 (s, 3H), 2.40-2.56 (m, 1H), 2.73 (t, J=12.11 Hz, 1H), 2.84-3.07 (m, 5H), 3.49 (d, J=13.87 Hz, 1H), 3.64-3.84 (m, 1H), 4.55 (s, 1H), 4.82 (d, J=11.91 Hz, 1H), 7.04-7.27 (m, 4H). MS (M + 1): 425.3 |

| Structure (Example) | Name | Data |
|---|---|---|
| 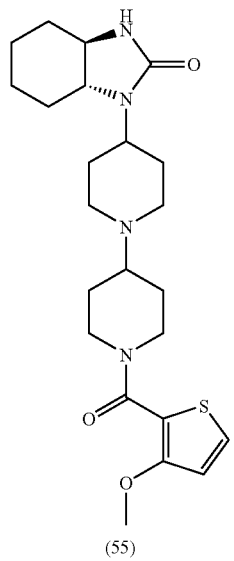<br>(55) | (3aR,7aR)-1-[1-[1-(3-methoxythiophene-2-carbonyl)-4-piperidyl]-4-piperidyl]-3a,4,5,6,7,7a-hexahydro-3H-benzoimidazol-2-one | 1H NMR (400 MHz, METHANOL-D4) - HCl salt-δ ppm 1.27-1.57 (m, 5H), 1.63 (d, J=12.89 Hz, 1H), 1.72 (d, J=14.45 Hz, 1H), 1.75-2.06 (m, 7H), 2.19-2.38 (m, 4H), 2.51-2.69 (m, 1H), 2.85-3.17 (m, 8H), 3.54-3.73 (m, 1H), 3.91 (s, 3H), 6.95 (d, J=5.47 Hz, 1H), 7.53 (d, J=6.64 Hz, 1H).<br>MS (M + 1): 447.0 |
| 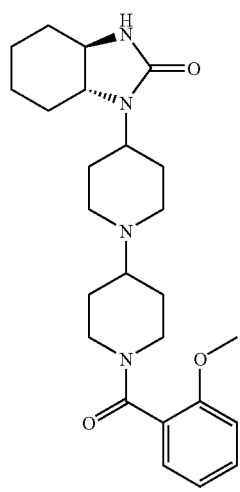<br>(56) | (3aR,7aR)-1-[1-[1-(2-methoxybenzoyl)-4-piperidyl]-4-piperidyl]-3a,4,5,6,7,7a-hexahydro-3H-benzoimidazol-2-one | 1H NMR (400 MHz, CHLOROFORM-D)<br>δ ppm 1.17-1.57 (m, 5H), 1.56-2.02 (m, 9H), 2.11-2.34 (m, 3H), 2.41-2.53 (m, 1H), 2.59-2.78 (m, 1H) 2.77-3.07 (m, 5H), 3.32-3.44 (m, 1H), 3.49 (d, J=13.48 Hz, 1H), 3.59-3.75 (m, 1H), 3.78 (d, J=7.62 Hz, 3H), 4.69-4.88 (m, 2H), 6.87 (d, J=8.40 Hz, 1H), 6.91-6.98 (m, 1H), 7.17 (d, J=16.70 Hz, 1H), 7.26-7.36 (m, 1H).<br>MS (M + 1): 441.1 |

-continued

| Structure (Example) | Name | Data |
|---|---|---|
| 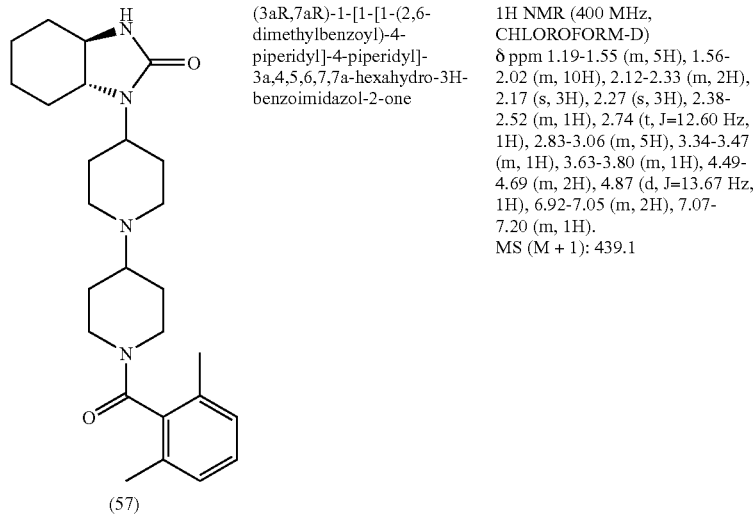 (57) | (3aR,7aR)-1-[1-[1-(2,6-dimethylbenzoyl)-4-piperidyl]-4-piperidyl]-3a,4,5,6,7,7a-hexahydro-3H-benzoimidazol-2-one | 1H NMR (400 MHz, CHLOROFORM-D) δ ppm 1.19-1.55 (m, 5H), 1.56-2.02 (m, 10H), 2.12-2.33 (m, 2H), 2.17 (s, 3H), 2.27 (s, 3H), 2.38-2.52 (m, 1H), 2.74 (t, J=12.60 Hz, 1H), 2.83-3.06 (m, 5H), 3.34-3.47 (m, 1H), 3.63-3.80 (m, 1H), 4.49-4.69 (m, 2H), 4.87 (d, J=13.67 Hz, 1H), 6.92-7.05 (m, 2H), 7.07-7.20 (m, 1H). MS (M + 1): 439.1 |

Example 58

(trans (+/−))-1-[1-[1-(thiophene-2-carbonyl)-4-piperidyl]-4-piperidyl]-3a,4,5,6,7,7a-hexahydro-3H-benzoimidazol-2-one

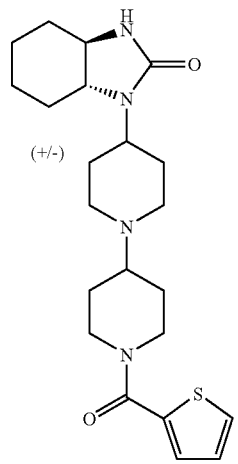

Step A

The preparation of tert-butyl 4-[(trans (+/−))-2-oxooctahydro-1H-benzimidazol-1-yl]-1,4'-bipiperidine-1'-carboxylate

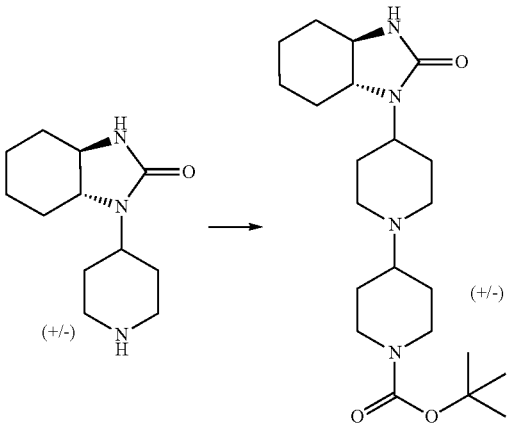

To a solution of (±)-(trans)-1-piperidin-4-yloctahydro-2H-benzimidazol-2-one. HCl (1.54 g, 5.95 mmol) in dichloromethane (30 mL) was added acetic acid (2 mL) and tert-butyl 4-oxopiperidine-1-carboxylate (2.75 g, 13.82 mmol). To this mixture was then added with sodium triacetoxy borohyrdide (4.4 g, 20.75 mmol) and stirred at room temperature over night. More sodium triacetoxy borohyrdide (0.6 g, 2.83 mmol) was then added and the mixture stirred at room temperature overnight. The mixture was then quenched with water, diluted in dichloromethane (200 mL), washed with 1N NaOH (7 mL) and brine (5 mL), dried and concentrated in vacuo. The crude product was then purified over silica gel (dichloromethane/ethylactate then dichloromethane/MeOH gradient) to provide the title compound as a white solid (1 g). MS (M+1): 407.21

Step B

The preparation of (trans (+/−))-1-(1,4'-bipiperidin-4-yl)octahydro-2H-benzimidazol-2-one

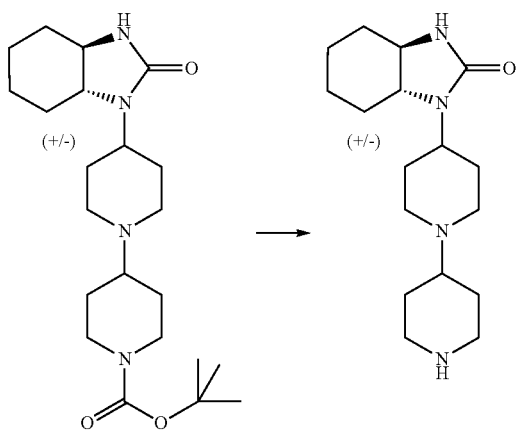

To a solution of tert-butyl 4-[(trans (+/−))-2-oxooctahydro-1H-benzimidazol-1-yl]-1,4'-bipiperidine-1'-carboxylate (1 g) in dichloromethane (20 mL) was added TFA (2 mL) and the mixture was stirred at room temperature over night. More TFA (2 mL) was then added and the mixture stirred for another 2 hours and then concentrated in vacuo to give the titled product. MS (M+1): 307.19

Step B

The preparation of (trans (+/−))-1-[1-[1-(thiophene-2-carbonyl)-4-piperidyl]-4-piperidyl]-3a,4,5,6,7,7a-hexahydro-3H-benzoimidazol-2-one

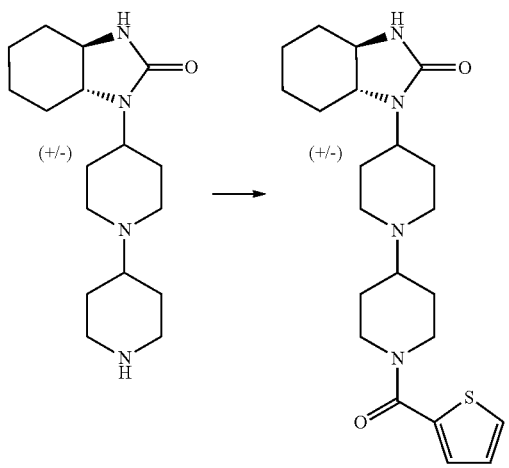

To a solution of (trans (+/−))-1-(1,4'-bipiperidin-4-yl)octahydro-2H-benzimidazol-2-one. 2TFA (180 mg, 0.31 mmol) in a mixture of dichloromethane and chloroform (1:4) was added diisopropylethylamine (0.2 mL, 1.1 mmol) followed by thiophene-2-carbonyl chloride (0.1 mL, 0.6 mmol) at room temperature. The mixture stirred 48 hours and then quenched with water. Diluted in dichloromethane (60 mL) and washed with 1N NaOH (5 mL) and brine (5 mL) and concentrated in vacuo. The crude was purified by high pH prep LCMS (acetonitrile/water) to provide 26 mg of the title compound as a white solid. 1H NMR (400 MHz, CHLOROFORM-D): δ ppm 1.26-1.58 (m, 6H), 1.59-2.03 (m, 9H), 2.12-2.34 (m, 3H), 2.44-2.64 (m, 1H), 2.82-3.06 (m, 6H), 3.62-3.84 (m, 1H), 4.29-4.57 (m, 2H), 4.63 (s, 1H), 7.01 (d, J=5.08 Hz, 1H), 7.18-7.27 (m, 1H), 7.35-7.46 (m, 1H). MS (M+1): 417.3

Example 59

(trans (+/−))-1-[1-[1-(2-phenylacetyl)-4-piperidyl]-4-piperidyl]-3a,4,5,6,7,7a-hexahydro-3H-benzoimidazol-2-one

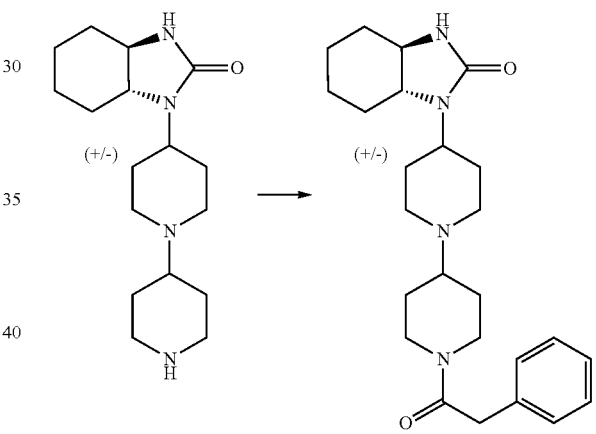

To a solution of (trans (+/−))-1-(1,4'-bipiperidin-4-yl)octahydro-2H-benzimidazol-2-one. 2TFA (180 mg, 0.31 mmol) in a mixture of dichloromethane and chloroform (1:4) was added diisopropylethylamine (0.2 mL, 1.1 mmol) followed by phenylacetyl chloride (0.1 mL, 0.6 mmol) at room temperature. The mixture stirred 48 hours and then quenched with water. The residue was then diluted in dichloromethane (60 mL) and washed with 1N NaOH (5 mL) and brine (5 mL) and then concentrated in vacuo. Crude was purified by high pH prep LCMS (acetonitrile/water) to provide 32 mg of the HCl salt of the title compound as a white solid. 1H NMR (400 MHz, CHLOROFORM-D) δ ppm 1.00-1.53 (m, 6H), 1.57-1.90 (m, 9H), 1.97 (d, J=10.74 Hz, 1H), 2.07-2.25 (m, 2H), 2.29 (d, J=11.33 Hz, 1H), 2.36-2.49 (m, 1H), 2.49-2.64 (m, 1H), 2.75-3.14 (m, 5H), 3.61-3.82 (m, 2H), 3.91 (d, J=13.09 Hz, 1H), 4.52-4.86 (m, 2H), 7.25 (s, 5H). MS (M+1): 425.3

Example 60 and 61

Ethyl 4-[(3aR,7aS)-2-oxooctahydro-1H-benzimidazol-1-yl]-1,4'-bipiperidine-1'-carboxylate and Ethyl 4-[(3aS,7aR)-2-oxooctahydro-1H-benzimidazol-1-yl]-1,4'-bipiperidine-1'-carboxylate

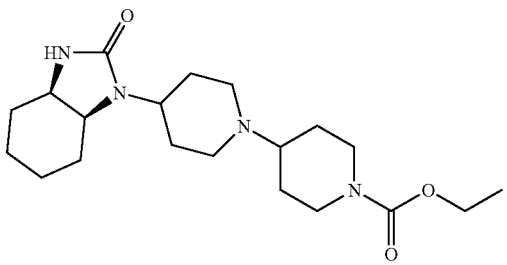

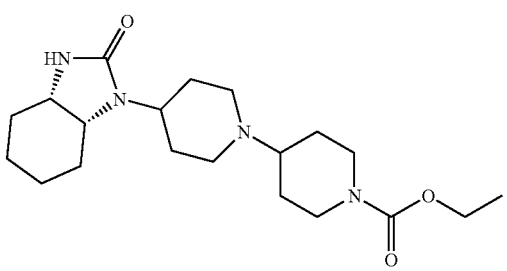

Step A

The preparation of cis (+/−)-ethyl 4-(2-oxooctahydro-1H-benzimidazol-1-yl)-1,4'-bipiperidine-1'-carboxylate

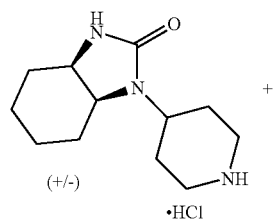

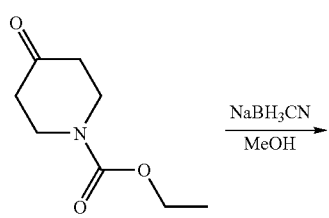

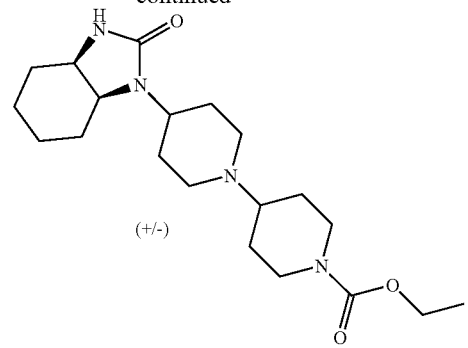

To a solution of cis-(+/−)-1-piperidin-4-yloctahydro-2H-benzimidazol-2-one hydrochloride salt (150 mg, 0.58 mmol) in 5 mL MeOH was added ethyl 4-oxopiperidine-1-carboxylate (119 mg, 0.69 mmol) and potassium acetate (1 eq). The mixture was stirred at room temperature for 30 min and sodium cyanoborohydride (182 mg, 2.90 mmol) was added. The mixture was stirred at room temperature overnight and concentrated in vacuo. The residue was dissolved in 20 mL DICHLOROMETHANE, and was washed with water. Organic layer was dried over MgSO$_4$, filtered and concentrated in vacuo. The crude was purified by High pH prep-LCMS to afford the desired racemic mixture as white solid (102 mg, 46%). MS (M+1): 379.3

Step B

Chiral Separation

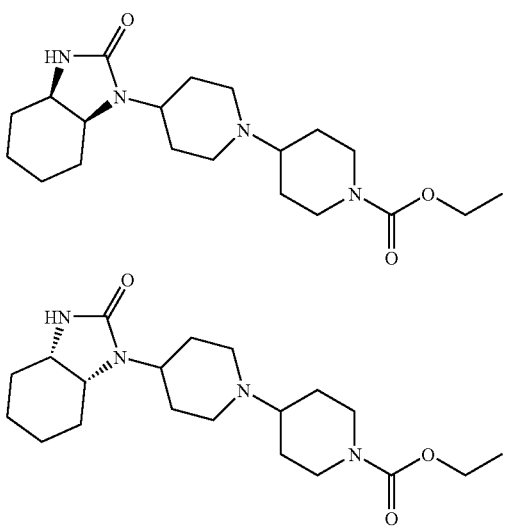

The racemic mixture of cis (+/−)-ethyl 4-(2-oxooctahydro-1H-benzimidazol-1-yl)-1,4'-bipiperidine-1'-carboxylate (102 mg) was separated by chiral AD column (20% EtOH/Hex.) to afford both enantiomers, Isomer 1 (30 mg) and Isomer 2 (35 mg).

Isomer 1: HPLC retention time=5.146 min, K': 0.24 (Chiralpak AD column, 4.6×250 mm column 40% Isopropanol/60% hexane) $^1$H NMR (400 MHz, CDCl$_3$): δ ppm 1.12-1.22 (m, 1H), 1.25 (t, J=7.13 Hz, 3H), 1.34-1.50 (m, 3H), 1.49-1.96 (m, 15H), 2.27 (q, J=11.72 Hz, 2H), 2.36-2.50

(m, 1H), 2.64-2.81 (m, 2H), 2.87-3.02 (m, 2H), 3.53-3.63 (m, 1H), 3.62-3.75 (m, 1H), 4.00 (s, 1H), 4.12 (q, J=7.10 Hz, 1H), 4.20 (s, 1H). MS (M+1): 379.3

Isomer 2: HPLC retention time=5.706 min, K': 0.37 (Chiralpak AD column, 4.6×250 mm column 40% Isopropanol/60% hexane). $^1$H NMR (400 MHz, CDCl$_3$): δ ppm 1.12-1.23 (m, 1H), 1.25 (t, J=7.03 Hz, 3H), 1.34-1.49 (m, 3H), 1.48-2.10 (m, 13H), 2.18-2.35 (m, 2H), 2.35-2.53 (m, 1H), 2.72 (dd, J=11.82 Hz, 2H), 2.85-3.07 (m, 2H), 3.50-3.74 (m, 3H), 3.98-4.38 (m, 4H). MS (M+1): 379.3

Example 62

Isopropyl 4-[(3aR,7aS)-2-oxooctahydro-1H-benzimidazol-1-yl]-1,4'-bipiperidine-1'-carboxylate

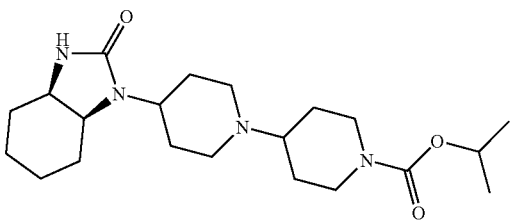

Step A

The preparation of (1R,2R) (2-benzyloxycyclohexyl) carbamic acid tert-butyl ester

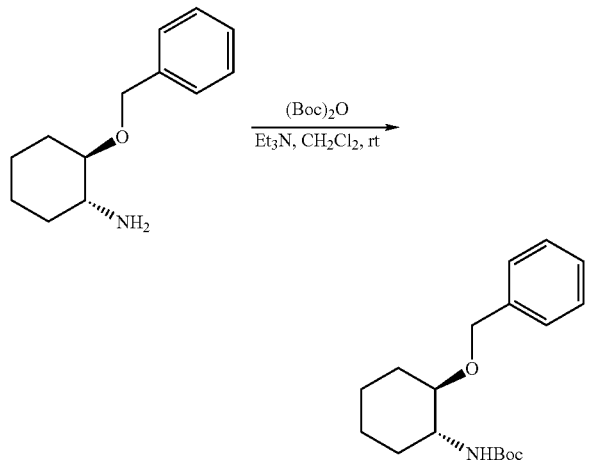

To a solution of 2-benzyloxycyclohexylamine (5 g, 24.39 mmol) in dichloromethane (60 mL), di-tert-butyldicarbonate (6.4 g, 29.28 mmol) was added followed by the addition of triethylamine (6.75 mL) at 0° C. The reaction mixture was stirred at room temperature for 4 h, diluted with dichloromethane (80 mL), washed with saturated sodium bicarbonate solution (2×100 mL). The organic layer was separated, dried over anhydrous sodium sulfate and concentrated. The crude compound obtained was purified by column chromatography on silica gel using 2% MeOH/dichloromethane to give the desired compound as a solid (7 g, 95%). MS (M+1): 306.07

Step B

The preparation of (1R,2R) (2-Hydroxycyclohexyl)-carbamic acid tert-butyl ester

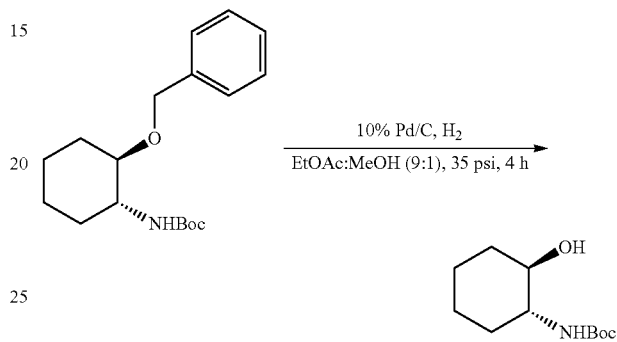

To a solution of (1R,2R) (2-benzyloxycyclohexyl) carbamic acid tert-butyl ester (7 g, 23 mmoles) in a 9:1 mixture of ethyl acetate and methanol (80 mL), 10% Pd—C (1.13 g) was added and hydrogenated at 35 psi for 4 h. The catalyst was removed by filtration through a celite pad. The filtrate was concentrated to give the title compound as an oil (4.7 g, 95%). MS: (M+1): 215.95

Step C

The preparation of methanesulphonic acid (1R,2R) (2-tert-butoxycarbonylamino)cyclohexyl ester

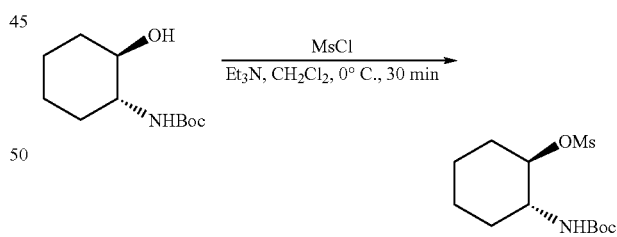

To a mixture of (1R,2R) (2-hydroxy-cyclohexyl)-carbamic acid tert-butyl ester (4.7 g, 21.86 mmol) and triethylamine (6.08 mL) in dichloromethane (80 mL), methanesulphonyl chloride (2.0 mL, 26.23 mmol) was added at 0° C. The reaction mixture was stirred at ° C. for 30 min and then brought to room temperature. Reaction mixture was diluted with dichloromethane (30 mL), washed with saturated sodium bicarbonate solution (80 mL), organic layer was separated and dried over anhydrous sodium sulfate. The solvent was removed under reduced pressure and the product was purified by flash chromatography (Dichloromethane: MeOH=98:2) to give the tile compound as an oil (5.6 g, 87%). MS: (M+1): 294.12

Step D

The preparation of (1R,2S) (2-Azidocyclohexyl-carbamic acid) tert-butyl ester

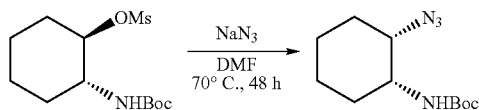

To a solution of (1R,2R) methanesulphonic acid (2-tert-butoxycarbonylamino)cyclohexyl ester (5.6 g, 19.11 mmol) in DMF (60 mL), sodium azide (7.45 g, 114.66 mmol) was added and the reaction mixture was stirred at 70° C. for 18 h. TLC examination indicated the reaction is incomplete, then additional 2.48 g of sodium azide was added, and stirring is continued for 24 h. Solvent was removed under reduced pressure, the residue was dissolved in ethyl acetate (100 mL), washed with saturated sodium bicarbonate solution (2×35 mL) and brine (2×40 mL). The organic layer was collected and dried on sodium sulfate. The solvent was removed under reduced pressure and the product was purified by flash chromatography (Dichloromethane: MeOH=99:1) to give the title compound as a solid (1.8 g, 40%). MS (M+1): 241.04

Step E

The preparation of (1R,2S) (2-amino-cyclohexyl)-carbamic acid tert-butyl ester

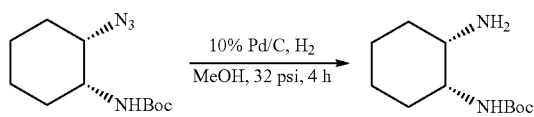

To a solution of compound (1R,2S) (2-Azidocyclohexyl-carbamic acid) tert-butyl ester (1.8 g, 7.5 mmol) in methanol (20 mL), 10% Pd—C (360 mg) was added and hydrogenated at 32 psi for 4 h Parr hydrogenator. The reaction mixture was filtered on a celite pad and the filtrate was concentrated to give the title compound as a solid (1.1 g, 69%), which was used without further purification. MS: (M+1): 215.07

Step F

The preparation of (1S,2R)-4-(2-tert-butoxycarbonylamino)-piperidine-1-carboxylic acid benzyl ester

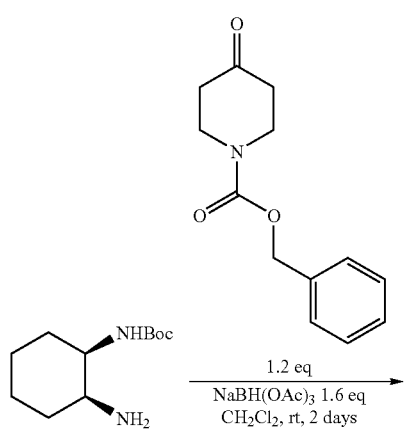

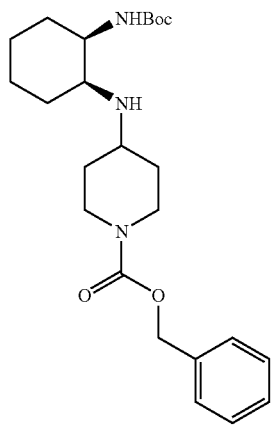

To a mixture of (1R,2S) (2-amino-cyclohexyl)-carbamic acid tert-butyl ester (1.1 g, 5.14 mmol) and N-benzyloxycarbonyl-4-pipeperidone (1.35 g, 6.16 mmol) in dichloromethane (50 mL), sodium triacetoxyborohydride (1.72 g, 8.2 mmol) was added and the reaction mixture was stirred for 2 days at room temperature. Reaction mixture was washed with sat. sodium bicarbonate solution (2×30 mL), organic layer was separated and dried over Na₂SO₄ and concentrated under reduced pressure to give the crude product which was further purified by triturating with diethyl ether to give the title compound (2 g, 90%). MS: (ESI) (M+1): 432.17

Step G

The preparation of {4-(2-aminocyclohexylamino)-piperidine-1-carboxylic acid benzyl ester)}

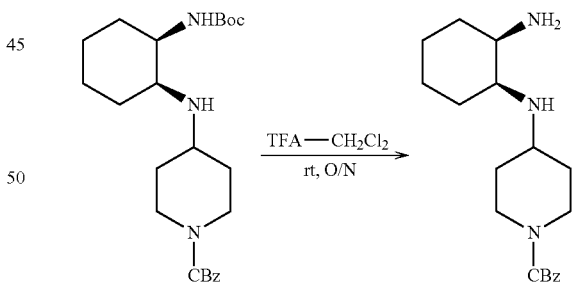

To a solution of compound (1S,2R)-4-(2-tert-butoxycarbonylamino)-piperidine-1-carboxylic acid benzyl ester (2 g, 4.6 mmol) in dichloromethane (45 mL), TFA (5 mL) was added and stirred at room temperature for 18 h. Volatiles were removed under reduced pressure. The product was dissolved in ethyl acetate (60 mL) and washed with 10% sodium carbonate solution (2×20 ml) and brine (2×20 mL) and dried over anhydrous sodium sulfate. The solvent was removed under reduced pressure to give the title compound (1.48 g, 96%). MS: (ESI) (M+1): 332.16

113

Step H

The preparation of 4-(2-oxo-octahydro-benzoimidazol-1-yl)-piperidine-1-carboxylic acid benzyl ester

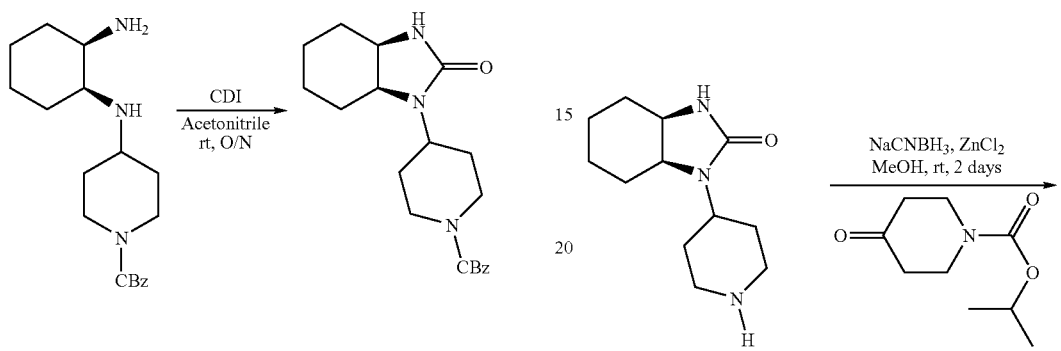

To a solution of compound {4-(2-aminocyclohexylamino)-piperidine-1-carboxylic acid benzyl ester)} (1.48 g, 4.47 mmoles) in acetonitrile (50 mL), 1,1'-carbonyldiimidazole (0.86 g, 5.36 mmole) was added and the reaction mixture was stirred at room temperature for 18 h. Reaction mixture was concentrated under reduced pressure, dissolved again in dichloromethane (60 mL) washed with water (2×100 mL) and dried over anhydrous sodium sulfate. The solvent was removed under reduced pressure to give the title compound as a solid (1.45 g, 90%). MS: (M+1): 358.13

Step I

The preparation of (1-piperidin-4-yl-octahydro)-benzoimidazol-2-one

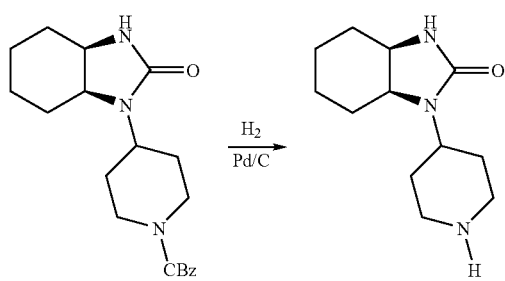

To a solution of compound 4-(2-oxo-octahydro-benzoimidazol-1-yl)-piperidine-1-carboxylic acid benzyl ester (1.45 g, 4.06 mmol) in methanol (25 mL), 10% Pd/C (200 mg) was added and hydrogenated at 32 psi in a Parr hydrogenator for 4 h. The catalyst was removed by filtration on a celite pad and the filtrate was concentrated to give the title compound as a solid (0.9 g, 90.6%). MS (M+1): 224.3

114

Step J

The preparation of isopropyl 4-[(3aR,7aS)-2-oxooctahydro-1H-benzimidazol-1-yl]-1,4'-bipiperidine-1'-carboxylate

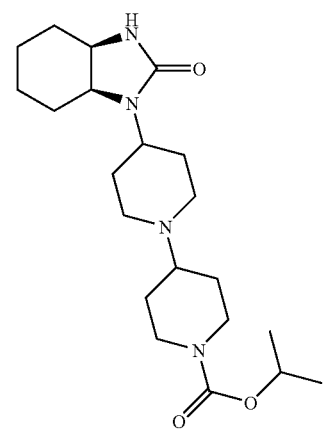

To a mixture of (1-piperidin-4-yl-octahydro)-benzoimidazol-2-one (0.9 g, 4 mmol) and 4-oxo-piperidine-1-carboxylic acid isopropyl ester (1.2 g, 6.48 mmol) in methanol (50 mL), sodium cyanoborohydride (0.750 g, 12 mmol) followed by zinc chloride (1.08 g, 8 mmol) were added and the reaction mixture was stirred at room temperature for 2 days. Solvent was removed under reduced pressure; to the residue 30 ml 1M NaOH solution was added. The product was extracted with dichloromethane (2×50 mL). The combined organic extracts were dried on MgSO$_4$, filtered and concentrated under reduced pressure to afford the crude material. The product was purified by flash chromatography (Dichloromethane: MeOH=95:5) to give the title compound as a white solid (0.395 g, 25%). MS: (M+1): 393.23

Example 63

Isopropyl 4-[(3aS,7aR)-2-oxooctahydro-1H-benzimidazol-1-yl]-1,4'-bipiperidine-1'-carboxylate

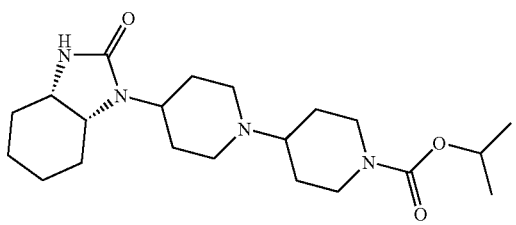

Step A

The preparation of cis-(+/−)-tert-butyl 4-(2-oxooctahydro-1H-benzimidazol-1-yl)-1,4'-bipiperidine-1'-carboxylate

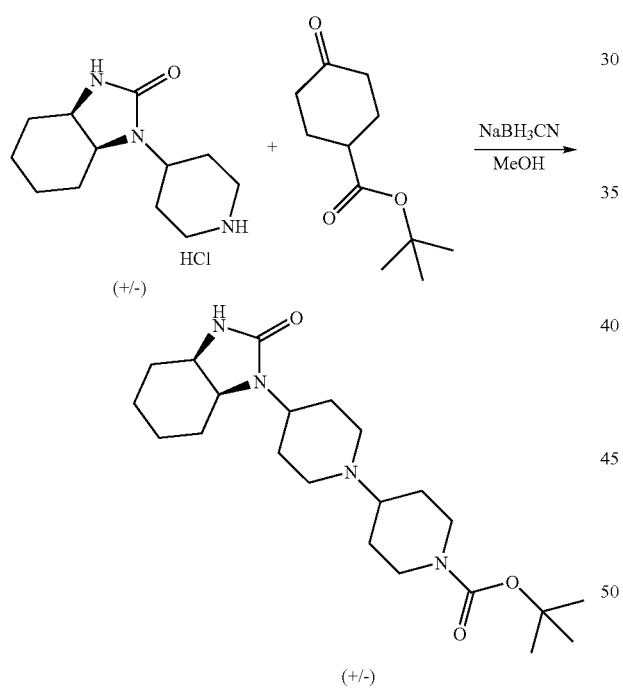

To a solution of cis-(+/−)-1-piperidin-4-yloctahydro-2H-benzimidazol-2-one Hydrochloride salt (263 mg, 1.01 mmol) in MeOH (5 mL) was added tert-butyl 4-oxopiperidine-1-carboxylate (241 mg, 1.21 mmol). The mixture was stirred at room temperature for 30 min before sodium cyanoborohydride (95 mg, 1.52 mmol) was added. The mixture was stirred overnight at room temperature, additional amount of tert-butyl 4-oxopiperidine-1-carboxylate and sodium cyanoborohydride (1 eq each) were added and stirred at room temperature for 3 more days. MeOH was concentrated in vacuo, the residue dissolved in dichloromethane (20 mL) and washed with water. The organic layer was dried over MgSO₄, filtered and concentrated in vacuo. To provide the title compound (244 mg, 59%) MS (M+1): 407.4

Step B

The preparation of cis-(+/−)-1-(1,4'-bipiperidin-4-yl)octahydro-2H-benzimidazol-2-one hydrochloride salt

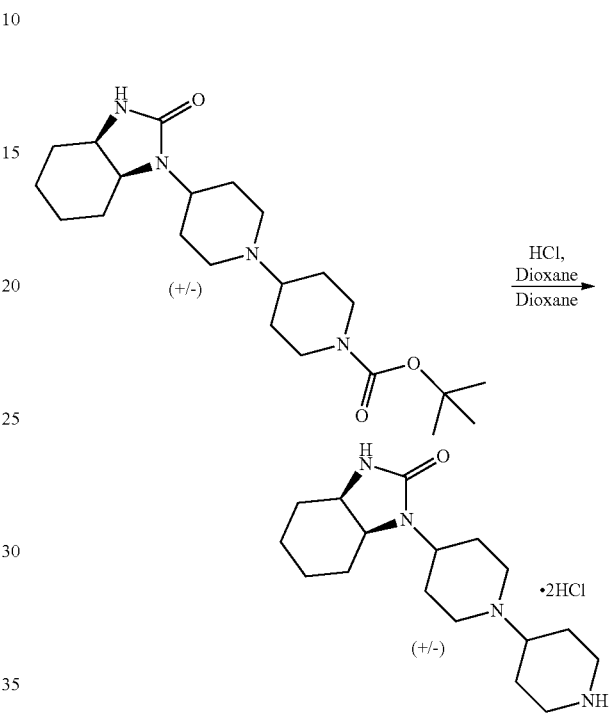

A 4N solution of hydrochloric acid in dioxane (1.0 mL, 4.0 mmol) was added to a solution of cis-(+/−)-tert-butyl 4-(2-oxooctahydro-1H-benzimidazol-1-yl)-1,4'-bipiperidine-1'-carboxylate (244 mg, 0.60 mmol) from Step A in dioxane (5 mL). The reaction was stirred at room temperature for 7 h and the mixture was concentrated in vacuo. The product (251 mg) was used directly for the next step without further purification. MS (M+1): 307.4

Step C

The preparation of cis-(+/−)-isopropyl 4-(2-oxooctahydro-1H-benzimidazol-1-yl)-1,4'-bipiperidine-1'-carboxylate

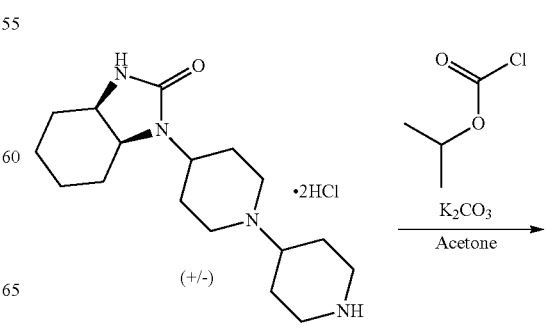

-continued

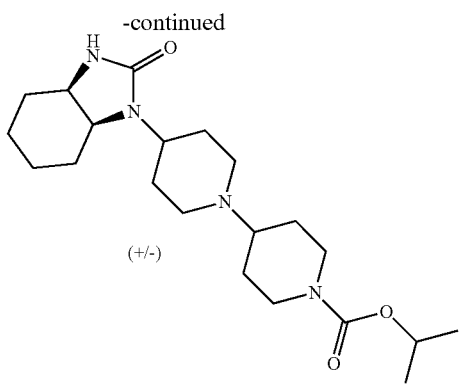
(+/-)

To a solution of cis-(+/−)-1-(1,4'-bipiperidin-4-yl)octahydro-2H-benzimidazol-2-one hydrochloride salt from step B (70 mg, 0.18 mmol) in 5 ml acetone was added potassium carbonate (49 mg, 0.36 mmol) followed by 1M isopropyl chloroformate in toluene (0.36 mL, 0.36 mmol) and the mixture was stirred at room temperature for 3 h. Removal of solvent gave a residue, which was dissolved in dichloromethane, and then water was added. The mixture was passed through VARIAN CHEM ELUT™ cartridges. The cartridge was rinsed with dichloromethane (2×20 mL). The dichloromethane solution was concentrated in vacuo and the crude product was purified by high pH prep-LCMS H to afford the title compound (40 mg, 56%). $^1$H NMR (400 MHz, CDCl$_3$): δ ppm 1.14-1.21 (m, 1H), 1.23 (d, J=6.25 Hz, 6H), 1.33-1.48 (m, 3H), 1.48-1.67 (m, 6H), 1.66-1.95 (m, 8H), 2.43 (t, J=10.94 Hz, 1H), 2.71 (t, J=12.21 Hz, 2H), 2.95 (dd, J=21.09, 10.35 Hz, 2H), 3.52-3.63 (m, 2H), 3.68 (t, J=12.01 Hz, 1H), 4.02 (s, 1H), 4.20 (s, 2H), 4.80-4.98 (m, 1H). MS (M+1): 393.3

Step D

Chiral Separation

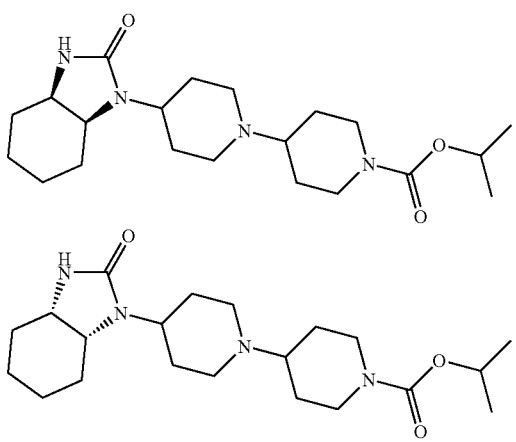

The racemic mixture obtained in from step C (35 mg) was separated on chiral OD column (30% EtOH/Hexane) to provide enantiomers, isomer 1 and isomer 2.

Isomer 1 (Example 63) (10 mg): (Identified as Example 63 by comparing retention time with Example 62 prepared by independent method described above) HPLC retention time=7.956 min, K': 0.92 (Chiralpak OD column, 4.6×250 mm column 20% Ethanol/80% hexane): 1H NMR (400 MHz, CDCl$_3$) δ ppm 1.24 (d, J=6.25 Hz, 6H), 1.33-1.46 (m, 1H), 1.50-1.66 (m, 15H), 1.65-1.78 (m, 2H), 1.75-2.08 (m, 4H), 2.21-2.56 (m, 1H) 2.64-3.13 (m, 2H), 3.49-3.86 (m, 2H), 4.00-4.41 (m, J=67.57 Hz, 2H), 4.84-4.96 (m, 1H). MS (M+1): 393.2.

Isomer 2 (Example 62) (10 mg): HPLC retention time=9.160 min (Identical retention time as Example 62 prepared by independent method described above), K': 1.21 (Chiralpak OD column, 4.6×250 mm column 20% Ethanol/80% hexane) $^1$H NMR (400 MHz, CDCl$_3$) δ ppm 0.84-1.15 (m, 2H), 1.24 (d, J=6.25 Hz, 6H), 1.30-1.51 (m, 5H), 1.48-1.78 (m, 11H), 1.78-1.97 (m, 2H), 1.96-2.22 (m, 1H), 2.21-2.61 (m, 1H), 2.61-3.09 (m, 2H), 3.18-3.82 (m, 3H), 3.89-4.46 (m, 2H), 4.83-4.97 (m, 1H). MS (M+1): 393.2

Example 64 cis(+/−)-1-(1'-benzoyl-1,4'-bipiperidin-4-yl)octahydro-2H-benzimidazol-2-one

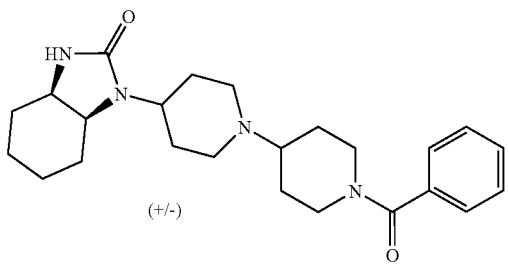
(+/-)

Step A

The preparation of cis-(+/−)-benzyl-4-(2-oxooctahydro-1H-benzimidazol-1-yl)-1,4'-bipiperidine-1'-carboxylate

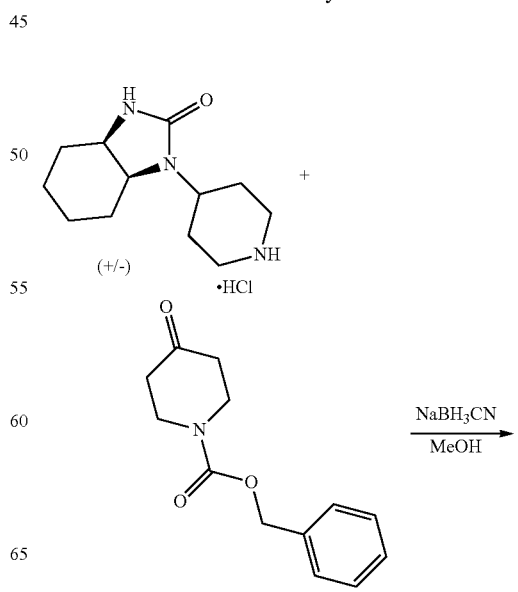

-continued

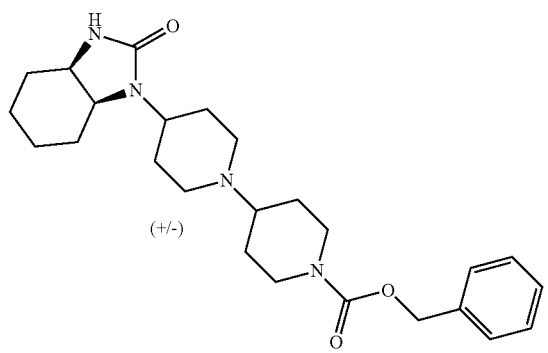

Following the similar procedure described in step A of Example 60 and 61, cis-(+/−)-benzyl-4-(2-oxooctahydro-1H-benzimidazol-1-yl)-1,4'-bipiperidine-1'-carboxylate (800 mg, 94%) was obtained. MS (M+1): 441.4

Step B: The preparation of cis-(+/−)-1-(1,4'-bipiperidin-4-yl)octahydro-2H-benzimidazol-2-one

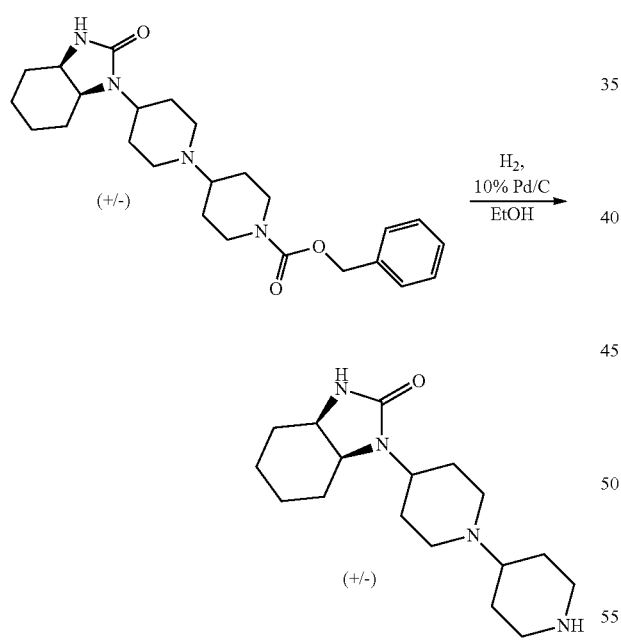

To a solution of cis-(+/−)-benzyl-4-(2-oxooctahydro-1H-benzimidazol-1-yl)-1,4'-bipiperidine-1'-carboxylate (800 mg, 1.82 mmol) in EtOH (50 mL) was added 10% Pd/C (80 mg) and the mixture was hydrogenated at 40 psi for 3 h. Filtration of catalyst on celite and removal of solvent afforded the title compound (372 mg, 67%), which was used without further purification. MS (M+1): 306.0

Step C

The preparation of cis(+/−)-1-(1'-benzoyl-1,4'-bipiperidin-4-yl)octahydro-2H-benzimidazol-2-one

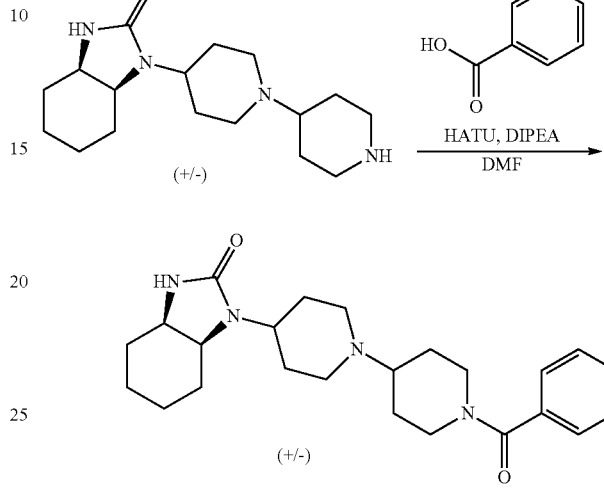

A solution of benzoic acid (21 mg, 0.17 mmol), HATU (63 mg, 0.17 mmol) and diisopropylethylamine (0.06 mL, 0.34 mmol) in dry DMF (3 mL) was stirred at room temperature for 10 minutes. Crude cis-(+/−)-1-(1,4'-bipiperidin-4-yl)octahydro-2H-benzimidazol-2-one from Step B: The preparation of B (51 mg, 0.17 mmol) was added to the solution and the mixture was stirred at room temperature for overnight. The solvent was removed in vacuo, the residue was dissolved in dichloromethane (15 mL), washed with saturated NaHCO$_3$ and brine and dried over Na$_2$SO$_4$. The crude product was purified with high pH prep-LCMS to provide the title compound (28 mg, 41%). $^1$H NMR (400 MHz, CDCl$_3$): δ ppm 1.14-1.29 (m, 1H), 1.33-1.48 (m, 2H), 1.50-2.00 (m, 13H), 2.19-2.36 (m, 2H), 2.46-2.60 (m, 1H), 2.65-2.86 (m, 1H), 2.88-3.10 (m, 3H), 3.53-3.63 (m, 2H), 3.63-3.74 (m, 1H), 3.74-3.91 (m, 1H), 4.02 (s, 1H), 4.77 (d, J=9.18 Hz, 1H), 7.36-7.44 (m, 5H). MS (M+1): 411.2

Example 65 cis (+/−)-1-[1'-(cyclopentylcarbonyl)-1,4'-bipiperidin-4-yl]octahydro-2H-benzimidazol-2-one

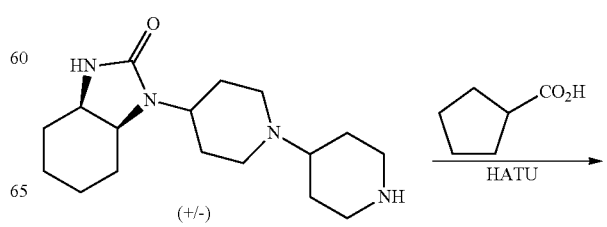

-continued

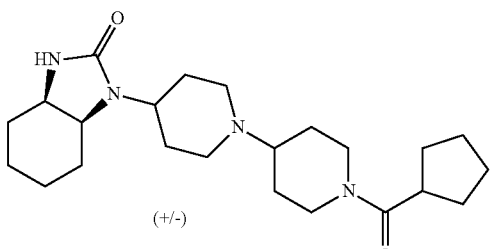
(+/-)

Following the procedure of step C of Example 64, cis (+/−)-1-[1'-(cyclopentylcarbonyl)-1,4'-bipiperidin-4-yl]octahydro-2H-benzimidazol-2-one (20 mg, 20%) was obtained. $^1$H NMR (400 MHz, CDCl$_3$) δ ppm 1.07-1.27 (m, 1H), 1.31-1.47 (m, 3H), 1.47-1.98 (m, 20H), 2.14-2.37 (m, 2H), 2.39-2.65 (m, 2H), 2.81-3.06 (m, 4H), 3.49-3.66 (m, 2H), 3.68 (t, J=11.91 Hz, 1H), 3.93-4.13 (m, 2H), 4.69 (d, J=13.28 Hz, 1H). MS (M+1): 403.3

Example 66 cis (+/−)-1-[1'-(3-thienylcarbonyl)-1,4'-bipiperidin-4-yl]octahydro-2H-benzimidazol-2-one

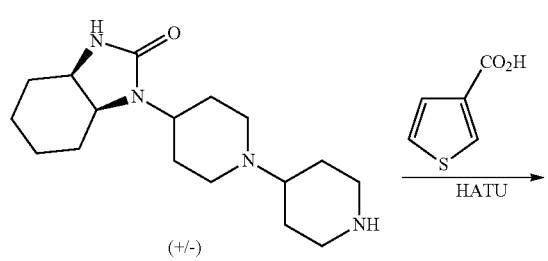
(+/-)

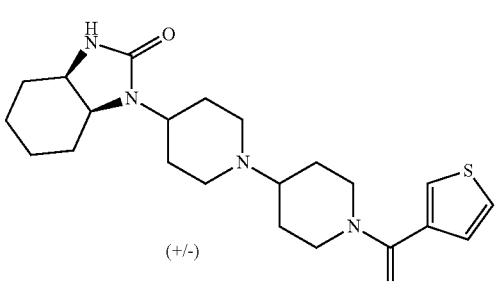
(+/-)

Following the procedure of step C of Example 64, cis (+/−)-1-[1'-(3-thienylcarbonyl)-1,4'-bipiperidin-4-yl]octahydro-2H-benzimidazol-2-one (17 mg, 19%) was obtained. $^1$H NMR (400 MHz, CDCl$_3$) δ ppm 1.13-1.30 (m, 1H), 1.31-2.04 (m, 17H), 2.14-2.40 (m, 2H), 2.46-2.62 (m, 1H), 2.65-3.16 (m, 3H), 3.53-3.63 (m, 2H), 3.63-3.75 (m, 1H), 3.94-4.12 (m, 1H), 4.71 (s, 1H), 7.17 (dd, J=4.98, 1.07 Hz, 1H), 7.33 (dd, J=5.08, 2.93 Hz, 1H), 7.50 (dd, J=2.83, 0.88 Hz, 1H). MS (M+1): 417.3

Example 67 cis (+/−)-1-[1'-(2-thienylcarbonyl)-1,4'-bipiperidin-4-yl]octahydro-2H-benzimidazol-2-one

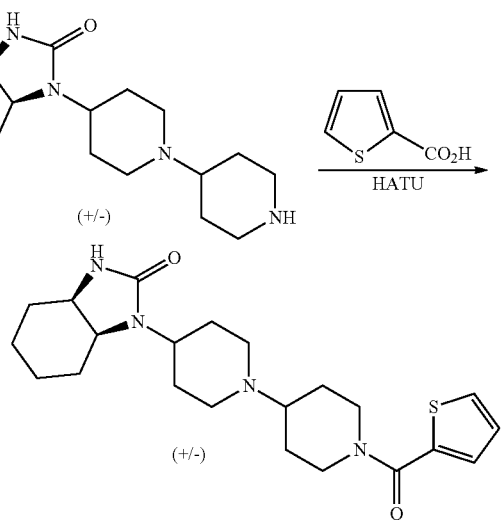
(+/-)

Following the procedure of step C of Example 64, cis (+/−)-1-[1'-(2-thienylcarbonyl)-1,4'-bipiperidin-4-yl]octahydro-2H-benzimidazol-2-one (39 mg, 33%) was obtained. $^1$H NMR (400 MHz, CDCl$_3$): δ ppm 1.13-1.28 (m, 1H), 1.33-1.45 (m, 1H), 1.45-1.98 (m, 15H), 2.19-2.35 (m, 2H), 2.45-2.62 (m, 1H), 2.85-3.08 (m, 4H), 3.53-3.63 (m, 2H), 3.63-3.76 (m, 1H), 4.03 (s, 1H), 4.50 (s, 1H), 7.04 (dd, J=4.98, 3.61 Hz, 1H), 7.25-7.30 (m, 1H), 7.43 (dd, J=4.98, 0.88 Hz, 1H). MS (M+1): 417.3

Example 68 cis (+/−)-1-(1'-butyryl-1,4'-bipiperidin-4-yl)octahydro-2H-benzimidazol-2-one

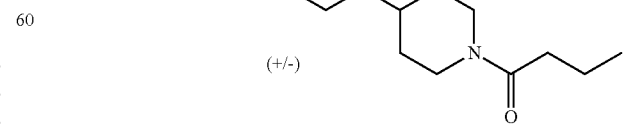
(+/-)

Following the procedure of step C of Example 64, cis (+/−)-1-(1'-butyryl-1,4'-bipiperidin-4-yl)octahydro-2H-benzimidazol-2-one (20 mg, 18%) was obtained. ¹H NMR (400 MHz, CDCl₃): δ ppm 0.96 (t, J=7.32 Hz, 3H), 1.12-1.28 (m, 1H), 1.30-1.97 (m, 17H), 2.16-2.37 (m, 4H), 2.39-2.60 (m, 2H), 2.81-3.08 (m, 3H), 3.50-3.63 (m, 2H), 3.62-3.79 (m, 1H), 3.91 (d, J=12.50 Hz, 1H), 4.01 (s, 1H), 4.68 (d, J=12.89 Hz, 1H). MS (M+1): 377.3

Example 69

(3aS,7aS)-1-methyl-3-[1-[1-[3-(2-oxopyrrolidin-1-yl)propanoyl]-4-piperidyl]-4-piperidyl]-3a,4,5,6,7,7a-hexahydrobenzoimidazol-2-one

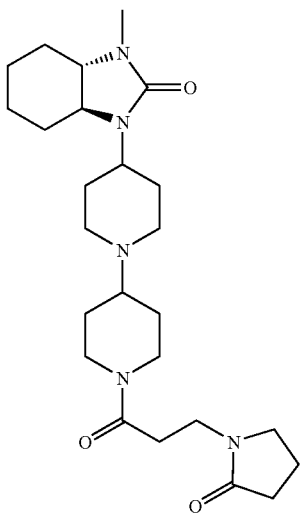

Step A

The preparation of tert-butyl 4-[(3aS,7aS)-3-methyl-2-oxooctahydro-1H-benzimidazol-1-yl]piperidine-1-carboxylate

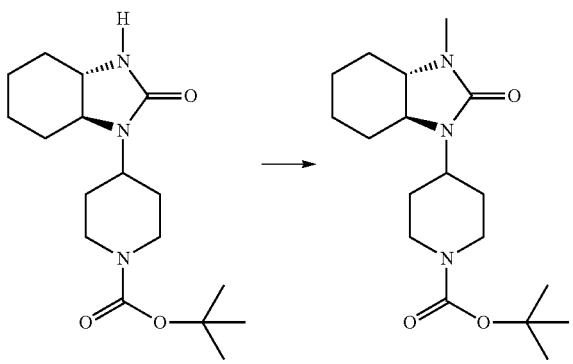

To a solution of (3aS,7aS)-1-piperidin-4-yloctahydro-2H-benzimidazol-2-one (1.5 g, 4.64 mmol) in DMF (30 mL) was added NaH (0.56 g, 14 mmol) and was stirred for one hour at room temperature. Methyl iodide (0.35 mL, 5.65 mmol) was then added dropwise and was stirred for 2 h at room temperature. The reaction was then quenched by slow addition of ice/water and the solvent was removed under reduced pressure. The residue was dissolved in dichloromethane, washed with saturated NaHCO₃ aqueous solution and then with brine, dried and concentrated in vacuo to give the title compound, which was used for the next step without purification. MS (M+1): 338.3

Step B

The preparation of (3aS,7aS)-1-methyl-3-piperidin-4-yloctahydro-2H-benzimidazol-2-one

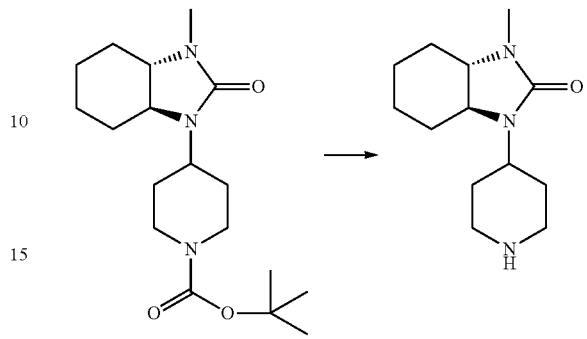

Crude tert-butyl 4-[(3aS,7aS)-3-methyl-2-oxooctahydro-1H-benzimidazol-1-yl]piperidine-1-carboxylate was dissolved in dioxane (10 mL) and 4 M HCl (5 mL) was then added. The mixture was stirred at room temperature and then concentrated in vacuo to provide a yellow-pale solid (1.38 g). The salt was then treated with MP-carbonate to give the free base of the title compound. MS (M+1): 238.3

Step C

The preparation of tert-butyl 4-[(3aS,7aS)-3-methyl-2-oxooctahydro-1H-benzimidazol-1-yl]-1,4'-bipiperidine-1'-carboxylate

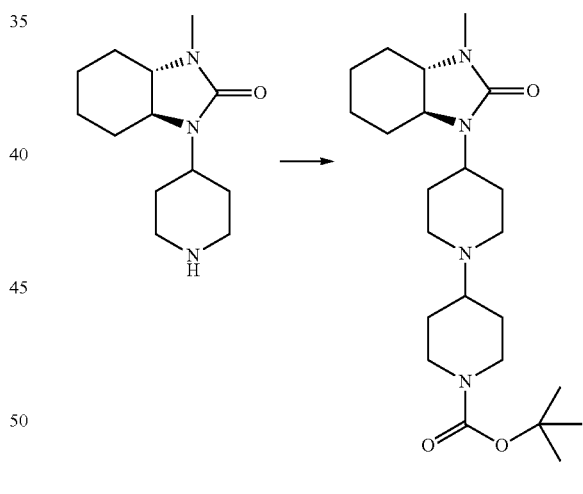

(3aS,7aS)-1-methyl-3-piperidin-4-yloctahydro-2H-benzimidazol-2-one (1.13 g, 4.75 mmol) was dissolved in MeOH (10 mL) and tert-butyl 4-oxopiperidine-1-carboxylate (1 g, 5.02 mmol) was then added. A solution containing sodium cyanoborohydride (0.49 g, 7.10 mmol) and ZnCl2 (0.38 g, 2.79 mmol) in MeOH (2 mL) was added and the mixture and stirred at room temperature overnight. The solvent was then removed under reduced pressure and the residue was dissolved in dichloromethane (150 mL). Organic layer was washed with 1N NaOH (10 mL) and brine (5 mL), dried and concentrated in vacuo. The residue was purified by column chromatography (dichloromethane-MeOH gradient) to provide the title compound as a white solid (1.6 g, 80%). MS (M+1): 421.4.

Step D

The preparation of (3aS,7aS)-1-(1,4'-bipiperidin-4-yl)-3-methyloctahydro-2H-benzimidazol-2-one

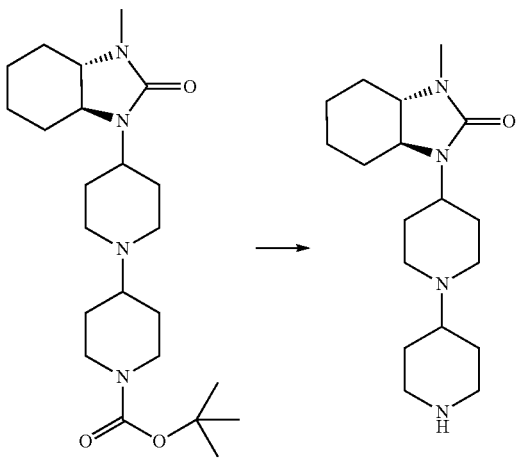

Tert-butyl 4-[(3aS,7aS)-3-methyl-2-oxooctahydro-1H-benzimidazol-1-yl]-1,4'-bipiperidine-1'-carboxylate (1.6 g, 3.80 mmol) was dissolved in MeOH (20 mL), 4M HCl in dioxane was added (4 mL) and the mixture stirred at room temperature for 2 hours. The mixture was then concentrated in vacuo to provide a yellow-pale solid which was washed with MeOH to give the HCl salt of the title compound as a white solid (1.1 g, 60% for 4 Step B: The preparation of s). MS (M+1): 321.3

Step E

The preparation of (3aS,7aS)-1-methyl-3-[1-[1-[3-(2-oxopyrrolidin-1-yl)propanoyl]-4-piperidyl]-4-piperidyl]-3a,4,5,6,7,7a-hexahydrobenzoimidazol-2-one)

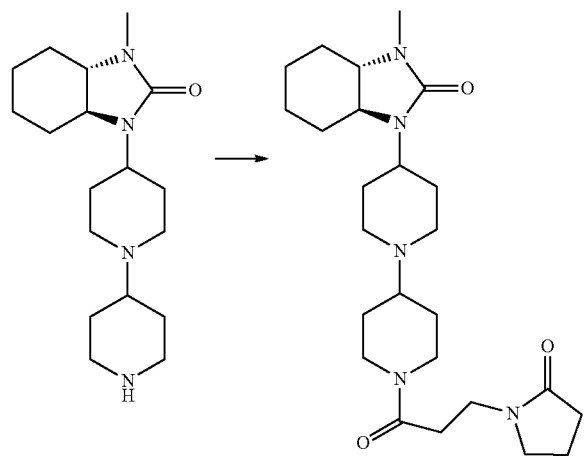

To a solution of (3aS,7aS)-1-(1,4'-bipiperidin-4-yl)-3-methyloctahydro-2H-benzimidazol-2-one. 2HCl (71 mg, 0.18 mmol) in DMF (4 mL) was added diisopropylethylamine (0.1 mL, 0.57 mmol) and 3-(2-oxopyrrolidin-1-yl)propanoic acid (34 mg, 0.2 mmol) at room temperature, the mixture was sonicated to dissolve the starting materials and HATU (75 mg, 0.2 mmol) was then added. The solvent was removed under reduced pressure and the mixture was diluted in dichloromethane (60 mL). The mixture was washed with 1N NaOH (5 mL) and brine (5 mL) and concentrated in vacuo. The residue was then purified by high pH prep LCMS to provide the title compound as a white solid (44 mg, 49%). HCl salt-1H NMR (400 MHz, METHANOL-D4) δ ppm 1.24-1.53 (m, 4H), 1.53-1.71 (m, 1H), 1.76-2.11 (m, 7H), 2.10-2.37 (m, 4H), 2.41 (t, J=8.20 Hz, 3H), 2.55-2.81 (m, 4H), 2.66 (s, 3H), 2.87-3.01 (m, 1H), 3.05-3.22 (m, 3H), 3.39-3.67 (m, 8H), 3.74-3.89 (m, 1H), 4.14 (d, J=14.45 Hz, 1H), 4.67 (d, J=13.67 Hz, 1H). MS (M+1): 460.2

Example 70

(3aS,7aS)-3-[1-[1-(cyclopropanecarbonyl)-4-piperidyl]-4-piperidyl]-1-methyl-3a,4,5,6,7,7a-hexahydrobenzoimidazol-2-one

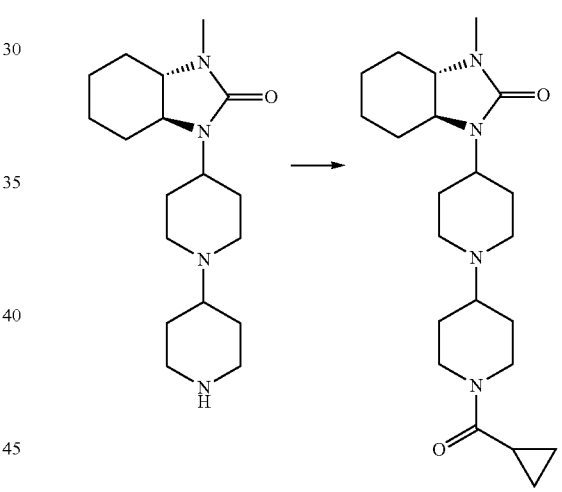

To a solution of (3aS,7aS)-1-(1,4'-bipiperidin-4-yl)-3-methyloctahydro-2H-benzimidazol-2-one. 2HCl (71 mg, 0.18 mmol) in DMF (4 mL) was added diisopropylethylamine (0.1 mL, 0.57 mmol) and cyclopropanecarboxylic acid (32 μL, 0.4 mmol) at room temperature, the mixture was sonicated to dissolve the starting materials and HATU (75 mg, 0.2 mmol) was then added. The reaction mixture was stirred at room temperature and the solvent was removed under reduced pressure. The residue was dissolved in dichloromethane (60 mL), the mixture was washed with 1N NaOH (5 mL) and brine (5 mL) and then concentrated in vacuo. The crude product was then purified by high pH prep-LCMS to provide the title compound as a white solid, which was converted to its HCl salt (60 mg, 78%). 1H NMR (400 MHz, METHANOL-D4) δ ppm 0.72-0.95 (m, 4H), 1.24-1.53 (m, 6H), 1.61 (d, J=12.50 Hz, 1H), 1.70 (d, J=14.06 Hz, 1H), 1.79-2.02 (m, 7H), 2.03-2.12 (m, 1H), 2.21-2.38 (m, 3H), 2.50-2.65 (m, 2H), 2.65 (s, 3H), 2.87-2.98 (m, 1H), 2.99-3.12 (m, 2H), 3.14 (d, J=13.28 Hz, 1H), 3.34 (s, 1H), 3.51-3.73 (m, 1H), 4.40 (d, J=13.28 Hz, 1H), 4.56 (d, J=12.89 Hz, 1H). MS (M+1): 389.2.

Example 71

(3aS,7aS)-1-methyl-3-[1-[1-(2-methylbenzoyl)-4-piperidyl]-4-piperidyl]-3a,4,5,6,7,7a-hexahydrobenzoimidazol-2-one

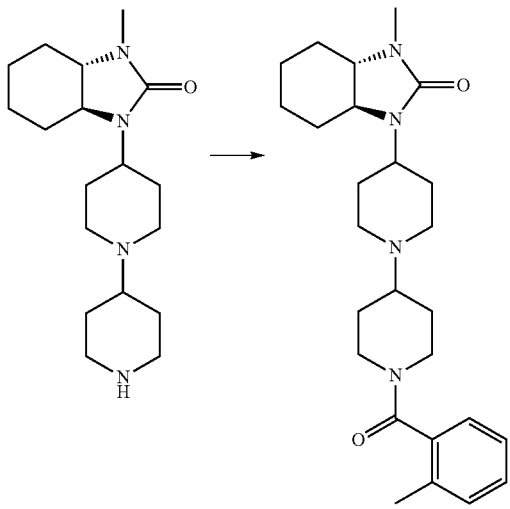

To a solution of (3aS,7aS)-1-(1,4'-bipiperidin-4-yl)-3-methyloctahydro-2H-benzimidazol-2-one. 2HCl (71 mg, 0.18 mmol) in DMF (4 mL) was added diisopropylethylamine (0.1 mL, 0.57 mmol) and 2-methylbenzoic acid (30 mg, 0.2 mmol) at room temperature, the mixture was then sonicated to dissolve the starting material and HATU (75 mg, 0.2 mmol) was then added. The reaction mixture was stirred at room temperature and the solvent was removed under reduced pressure. The mixture was dissolved in dichloromethane (60 mL), washed with 1N NaOH (5 mL) and brine (5 mL) and then concentrated in vacuo. The residue was then purified by high pH prep. LCMS to provide the title compound as a white solid (44 mg, 51%). (HCl salt) 1H NMR (400 MHz, METHANOL-D4) δ ppm 1.23-1.56 (m, 5H), 1.60 (d, J=12.89 Hz, 1H), 1.69 (d, J=11.72 Hz, 1H), 1.74-1.96 (m, 6H), 1.97-2.11 (m, 2H), 2.23 (s, 3H), 2.15-2.38 (m, 3H), 2.51-2.62 (m, 2H), 2.64 (s, 3H), 2.83 (t, J=11.91 Hz, 1H), 2.94 (t, J=10.16 Hz, 1H), 3.04 (t, J=11.72 Hz, 3H), 3.39-3.54 (m, 1H), 3.57-3.71 (m, 1H), 4.74 (d, J=12.89 Hz, 1H), 7.03-7.42 (m, 4H). MS (M+1): 439.3.

Example 72

(3aS,7aS)-1-[1-[1-(3-methoxythiophene-2-carbonyl)-4-piperidyl]-4-piperidyl]-3-methyl-3a,4,5,6,7,7a-hexahydrobenzoimidazol-2-one

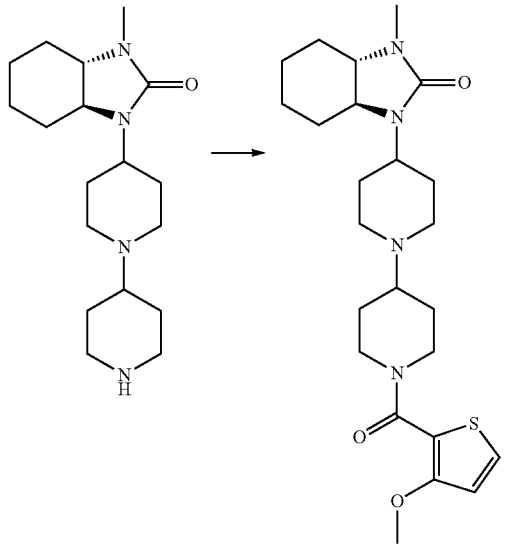

To a solution of (3aS,7aS)-1-(1,4'-bipiperidin-4-yl)octahydro-2H-benzimidazol-2-one. 2HCl (71 mg, 0.18 mmol) in DMF (4 mL) was added diisopropylethylamine (0.1 mL, 0.57 mmol) and 3-methoxythiophene-2-carboxylic acid (35 mg, 0.2 mmol) at room temperature, the mixture was then sonicated to dissolve the starting materials and HATU (75 mg, 0.2 mmol) was then added. The solvent was removed under reduced pressure and the mixture was diluted in dichloromethane (60 mL). The mixture was washed with 1N NaOH (5 mL) and brine (5 mL) and concentrated in vacuo. The residue was then purified by high pH prep. LCMS to provide the title compound as a white solid (49 mg, 55%). 1H NMR (400 MHz, CHLOROFORM-D) δ ppm 1.21-1.41 (m, 4H), 1.42-1.56 (m, 2H), 1.57-1.67 (m, 1H), 1.67-1.88 (m, 7H), 1.99 (d, J=8.98 Hz, 2H), 2.15-2.34 (m, 3H), 2.40-2.57 (m, 2H), 2.65 (s, 3H), 2.78-2.89 (m, 2H), 2.93 (t, J=9.96 Hz, 2H), 3.43 (s, 1H), 3.64-3.81 (m, 1H), 3.85 (s, 3H), 4.11-4.47 (m, 1H), 6.74 (d, J=5.47 Hz, 1H), 7.29 (d, J=5.47 Hz, 1H). MS (M+1): 461.2.

Example 73

Ethyl 4-[4-[(3aS,7aS)-2-oxo-3-prop-2-enyl-3a,4,5,6,7,7a-hexahydrobenzoimidazol-1-yl]-1-piperidyl]piperidine-1-carboxylate

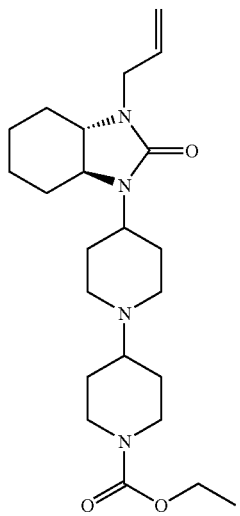

Step A

Preparation of tert-butyl 4-[(3aS,7aS)-3-allyl-2-oxooctahydro-1H-benzimidazol-1-yl]piperidine-1-carboxylate

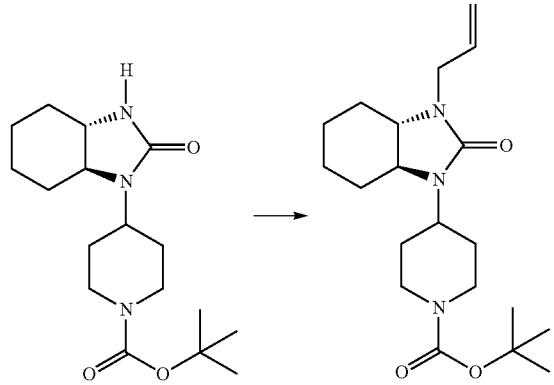

To a solution of (3aS,7aS)-1-piperidin-4-yloctahydro-2H-benzimidazol-2-one (0.4 g, 1.24 mmol) in DMF (10 mL) was added NaH (123 mg, 3.1 mmol). The mixture was then stirred for one hour at room temperature. Allyl iodide (0.13 mL, 1.36 mmol) was then added drop wise and the stirring continued for 2 hours. The reaction was quenched by slow addition of ice/water and the solvent was removed under reduced pressure. The residue diluted in dichloromethane (120 mL) and was washed with water (5 mL) and then brine, dried and concentrated in vacuo to provide the title compound, which was used for the next step without any purification. MS (M+1): 364.4.

Step B

Preparation of (3aS,7aS)-1-allyl-3-piperidin-4-yloctahydro-2H-benzimidazol-2-one

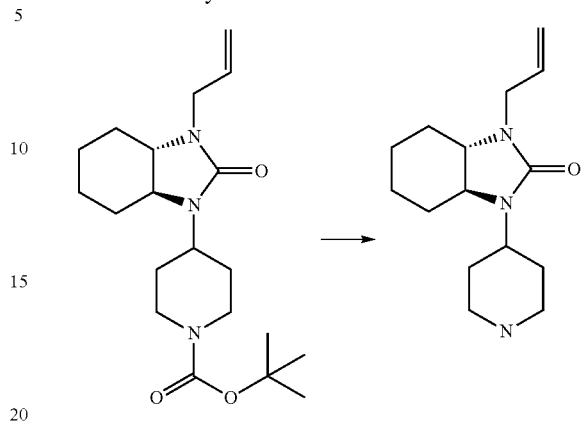

Tert-butyl 4-[(3aS,7aS)-3-allyl-2-oxooctahydro-1H-benzimidazol-1-yl]piperidine-1-carboxylate was dissolved in methanol (20 mL) and 4 M HCl (7 mL) was then added. The mixture was stirred at room temperature and then concentrated in vacuo. The salt was then converted to freebase by using MP-carbonate. MS (M+1): 264.2.

Step C

Preparation of ethyl 4-[(3aS,7aS)-3-allyl-2-oxooctahydro-1H-benzimidazol-1-yl]-1,4'-bipiperidine-1'-carboxylate

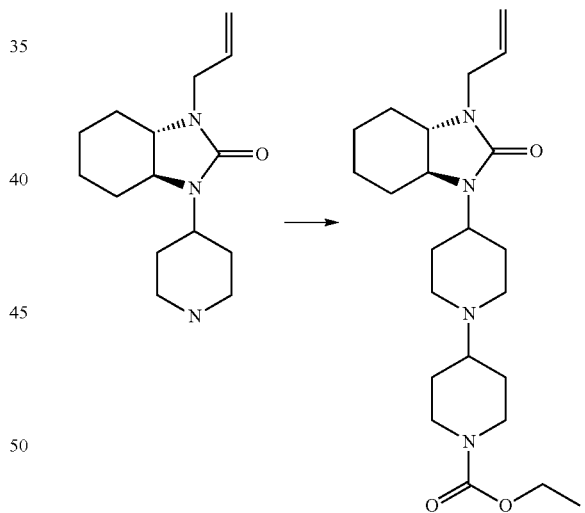

(3aS,7aS)-1-allyl-3-piperidin-4-yloctahydro-2H-benzimidazol-2-one (183 mg, 0.69 mmol) was dissolved in MeOH (2 mL) and ethyl 4-oxopiperidine-1-carboxylate (100 µL, 0.66 mmol) was added. A solution of sodium cyanoborohydride (82 mg, 1.19 mmol) and zinc chloride (47 mg, 0.34 mmol) in MeOH (1 mL) was then added drop wise at room temperature. The mixture was then stirred for 3 hours and then more sodium cyanoborohydride (40 mg) was added and the mixture stirred at room temperature over night. The solvent was then removed under reduced pressure and the residue was diluted in dichloromethane (80 mL). Washed with 1N NaOH (5 mL) and brine, dried and concentrated in vacuo. The residue was purified by high pH prep LCMS to provide the title compound (120 mg). 1H NMR (400 MHz, METHA- NOL-D4) δ ppm 1.24 (t, J=7.03 Hz, 3H), 1.28-1.48 (m, 6H), 1.53-1.64 (m, 1H), 1.65-1.74 (m, 1H), 1.77-1.99 (m, 6H), 1.99-2.10 (m, 1H), 2.22-2.36 (m, 3H), 2.42-2.58 (m, 1H), 2.69-2.86 (m, 3H), 2.89-3.11 (m, 3H), 3.56-3.71 (m, 1H), 3.72-3.78 (m, 2H), 4.09 (q, J=7.16 Hz, 2H), 4.17 (d, J=13.28 Hz, 2H), 5.03-5.26 (m, 2H), 5.62-5.84 (m, 1H). MS (M+1): 419.2

Example 74

Ethyl 4-[(3aS,7aS)-3-isopropyl-2-oxooctahydro-1H-benzimidazol-1-yl]-1,4'-bipiperidine-1'-carboxylate

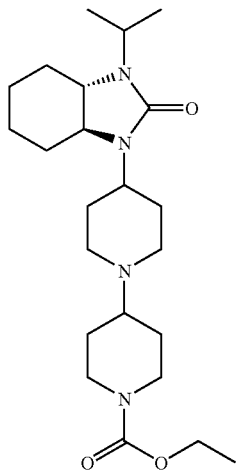

Step A

Preparation of tert-butyl 4-[(3aS,7aS)-3-isopropyl-2-oxooctahydro-1H-benzimidazol-1-yl]piperidine-1-carboxylate

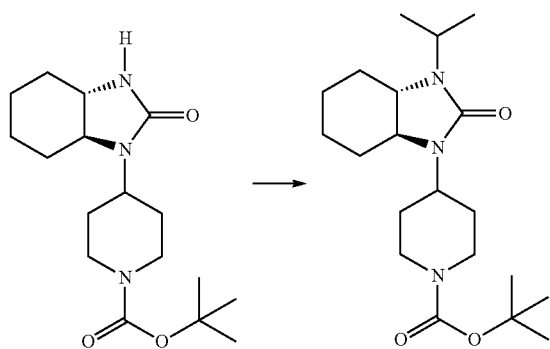

To a solution of (3aS,7aS)-1-piperidin-4-yloctahydro-2H-benzimidazol-2-one (0.4 g, 1.24 mmol) in DMF (10 mL) was added NaH (123 mg, 3.1 mmol) and the mixture was then stirred for one hour at room temperature. Isopropyl iodide (0.14 mL, 1.36 mmol) was then added drop wise and the stirring continued for 2 hours. The reaction was quenched by slow addition of ice/water and the solvent was removed under reduced pressure. The residue diluted in dichloromethane (120 mL) and was washed with water (5 mL) and brine, dried and concentrated in vacuo to give the title compound, which was used for the next step without any purification. MS (M+1): 366.3.

Step B

Preparation of (3aS,7aS)-1-isopropyl-3-piperidin-4-yloctahydro-2H-benzimidazol-2-one

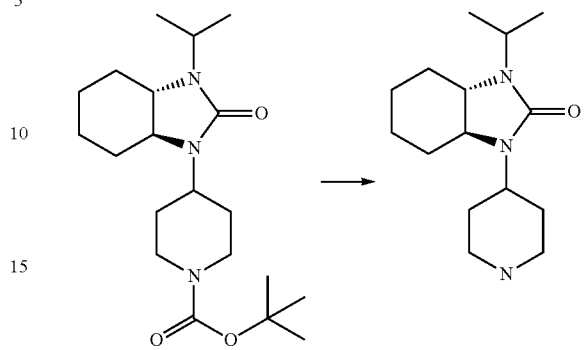

Tert-butyl 4-[(3aS,7aS)-3-isopropyl-2-oxooctahydro-1H-benzimidazol-1-yl]piperidine-1-carboxylate was dissolved in methanol (20 mL) and 4 M HCl (7 mL) was then added. The mixture was stirred at room temperature and then concentrated in vacuo to provide the title compound. MS (M+1): 266.34

Step C

Preparation of ethyl 4-[(3aS,7aS)-3-isopropyl-2-oxooctahydro-1H-benzimidazol-1-yl]-1,4'-bipiperidine-1'-carboxylate

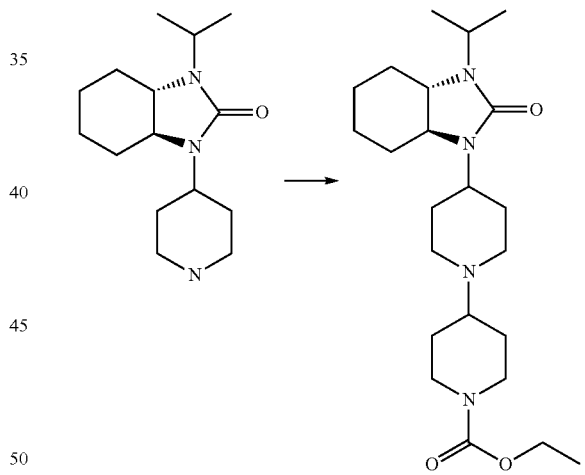

(3aS,7aS)-1-isopropyl-3-piperidin-4-yloctahydro-2H-benzimidazol-2-one (85 mg, 0.3 mmol) was dissolved in MeOH (2 mL) and ethyl 4-oxopiperidine-1-carboxylate (48 μL, 0.32 mmol) was added. A solution of sodium cyanoborohydride (31 mg, 0.45 mmol) and zinc chloride (20 mg, 0.15 mmol) in MeOH (1 mL) was then added drop wise at room temperature. The mixture was then stirred for 3 hours and then more sodium cyanoborohydride (40 mg) was added and the mixture stirred at room temperature over night. The solvent was then removed under reduced pressure and the residue was diluted in dichloromethane (80 mL) and was washed with 1N NaOH (5 mL), brine and then dried and concentrated in vacuo. The residue was purified by high pH prep LCMS to provide the title compound (30 mg). Free Base-1H NMR (400 MHz, METHANOL-D4): δ ppm 1.14 (dd, J=6.84, 5.27 Hz, 6H), 1.20 (t, J=7.23 Hz, 3H), 1.28-1.45 (m, 6H), 1.54 (d, J=12.50 Hz, 1H), 1.61-1.69 (m, 1H), 1.75-1.92 (m, 6H), 2.12-2.32 (m, 4H), 2.38-2.52 (m, 1H), 2.64-2.81 (m, 2H), 2.80-2.92 (m, 2H), 2.92-3.05 (m, 2H), 3.52-3.65 (m, 1H), 3.83-3.98 (m, 1H), 4.05 (q, J=7.03 Hz, 2H), 4.13 (d, J=13.28 Hz, 2H). MS (M+1): 421.4

Example 75

(3aS,7aS)-1-(1'-(1-methylcyclopropanecarbonyl)-1,4'-bipiperidin-4-yl)hexahydro-1H-benzo[d]imidazol-2(3H)-one

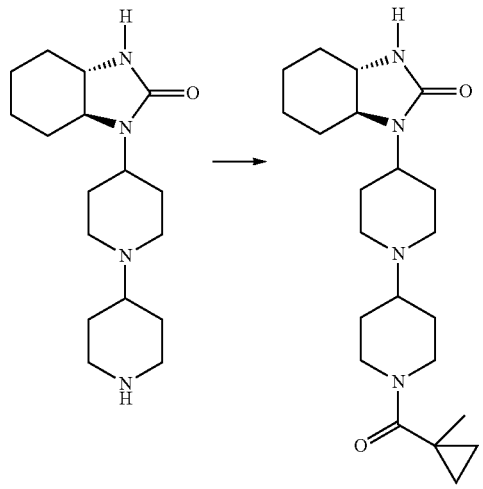

HBTU (284 mg, 0.75 mmol) was added to a solution of 1-methylcyclopropanecarboxylic acid (75 mg, 0.75 mmol), N,N-diisopropylethyl amine (194 mg, 1.50 mmol) and (3aS,7aS)-1-(1,4'-bipiperidin-4-yl)hexahydro-1H-benzo[d]imidazol-2(3H)-one (153.22 mg, 0.50 mmol) in DMA (10 mL) and stirred at room temperature for overnight. Concentrated in vacuo, diluted in dichloromethane (50 ml) and washed with sat. NaHCO$_3$ (10 mL). The organic layer was dried over MgSO$_4$, filtered and concentrated in vacuo. The crude product was purified by high pH Prep LCMS to give the titled compound (40 mg, 20.6%). 1H NMR (400 MHz, CHLOROFORM-D): δ ppm 0.51-0.59 (m, 2H) 0.86-0.94 (m, 2H) 1.30 (s, 3H) 1.33-1.45 (m, 6H) 1.68 (s, 1H) 1.74-1.84 (m, 7H) 1.96 (d, J=10.16 Hz, 1H) 2.21-2.32 (m, 3H) 2.48 (t, J=11.13 Hz, 1H) 2.76 (s, 1H) 2.92-3.03 (m, 4H) 3.71-3.81 (m, 1H) 4.49 (s, 3H). MS (M+1): 389.2

Example 76-81

Examples 76-81 Were Prepared via HBTU Coupling Method Similar to Example 75, Starting from (3aS,7aS)-1-(1,4'-bipiperidin-4-yl)octahydro-2H-benzimidazol-2-one and from the Corresponding Carboxylic Acid

| Structure (Example) | Name | Data |
|---|---|---|
| (76) | (3aS,7aS)-1-(1'-(2,2-difluorocyclopropanecarbonyl)-1,4'-bipiperidin-4-yl)hexahydro-1H-benzo[d]imidazol-2(3H)-one (mixture of diastereo isomers) | 1H NMR (400 MHz, CHLOROFORM-D): δ ppm 1.35-1.47 (m, 5H) 1.61-1.72 (m, 2H) 1.80 (dd, J=19.14, 9.37 Hz, 6H) 1.87-1.99 (m, 2H) 2.09-2.17 (m, 1H) 2.21-2.33 (m, 3H) 2.47-2.57 (m, 2H) 2.62-2.69 (m, 1H) 2.94 (m, 2H) 2.97-3.05 (m, 2H) 3.11 (td, J=11.72, 6.25 Hz, 1H) 3.71-3.81 (m, 1H) 4.07 (d, J=12.11 Hz, 1H) 4.53 (s, 1H) 4.57-4.67 (m, 1H). MS (M + 1) = 411.2 |

| Structure (Example) | Name | Data |
|---|---|---|
| 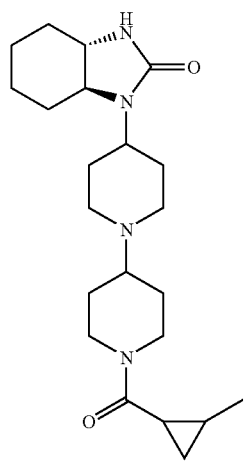 (77) | (3aS,7aS)-1-(1'-(2-methylcyclopropanecarbonyl)-1,4'-bipiperidin-4-yl)hexahydro-1H-benzo[d]imidazol-2(3H)-one (mixture of diastereo isomers) | 1H NMR (400 MHz, CHLOROFORM-D): δ ppm 0.52-0.59 (m, 1H) 1.11 (d, J=5.86 Hz, 3H) 1.15 (d, J=3.52 Hz, 1H) 1.33-1.45 (m, 7H) 1.63-1.73 (m, 1H) 1.77 (s, 2H) 1.79 (d, J=9.37 Hz, 5H) 1.96 (d, J=10.55 Hz, 1H) 2.30 (d, J=10.16 Hz, 3H) 2.47-2.59 (m, 2H) 2.93-3.03 (m, 5H) 3.71-3.81 (m, 1H) 4.23 (d, J=12.11 Hz, 1H) 4.59 (s, 1H) 4.64 (s, 1H). MS (M + 1) = 389.2 |
| 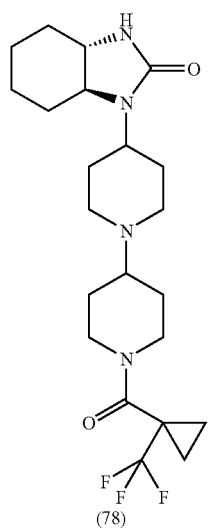 (78) | (3aS,7aS)-1-(1'-(1-(trifluoromethyl)cyclopropanecarbonyl)-1,4'-bipiperidin-4-yl)hexahydro-1H-benzo[d]imidazol-2(3H)-one | 1H NMR (400 MHz, CHLOROFORM-D): δ ppm 1.12-1.16 (m, 2H) 1.30-1.35 (m, 2H) 1.36-1.44 (m, 6H) 1.60 (s, 1H) 1.69 (m, 1H) 1.74-1.81 (m, 6H) 1.83 (s, 2H) 1.96 (d, J=11.33 Hz, 1H) 2.20-2.31 (m, 3H) 2.45-2.51 (m, 1H) 2.91-3.03 (m, 5H) 3.71-3.80 (m, 1H) 4.41 (s, 2H). MS (M + 1) = 443.2 |
| 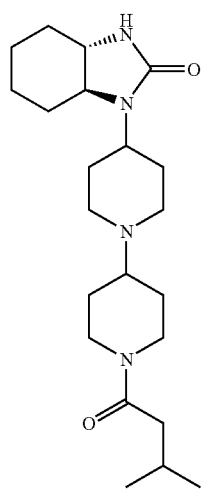 (79) | (3aS,7aS)-1-[1'-(3-methylbutanoyl)-1,4'-bipiperidin-4-yl]octahydro-2H-benzoimidazol-2-one | 1H NMR (400 MHz, CHLOROFORM-D): δ ppm 0.92 (d, J=6.64 Hz, 6H) 1.29-1.41 (m, 6H) 1.60-1.68 (m, 1H) 1.69-1.80 (m, 6H) 1.92 (d, J=10.94 Hz, 1H) 2.02-2.11 (m, J=13.48, 7.03, 6.74, 6.74 Hz, 1H) 2.15-2.27 (m, 5H) 2.39-2.51 (m, 2H) 2.87-2.99 (m, 6H) 3.66-3.76 (m, 1H) 3.88 (d, J=12.89 Hz, 1H) 4.53 (s, 1H) 4.65 (d, J=12.89 Hz, 1H). MS (M + 1) = 391.2 |

| Structure (Example) | Name | Data |
|---|---|---|
| 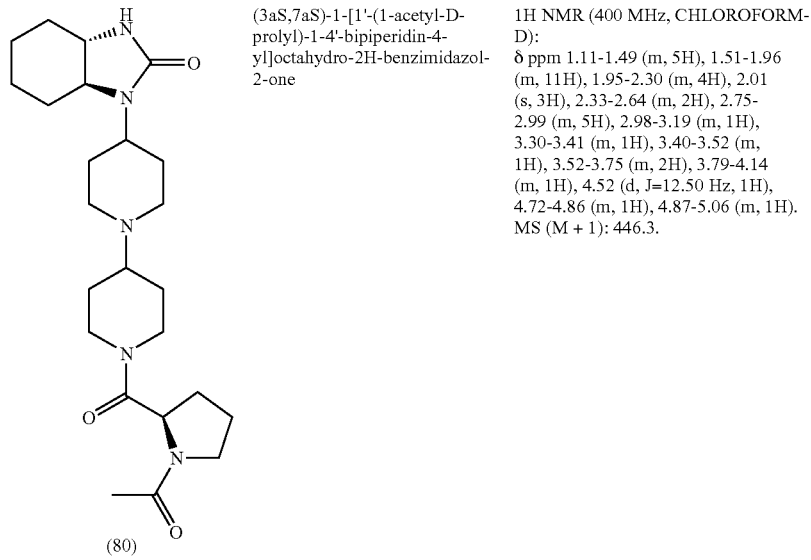 (80) | (3aS,7aS)-1-[1'-(1-acetyl-D-prolyl)-1-4'-bipiperidin-4-yl]octahydro-2H-benzimidazol-2-one | 1H NMR (400 MHz, CHLOROFORM-D): δ ppm 1.11-1.49 (m, 5H), 1.51-1.96 (m, 11H), 1.95-2.30 (m, 4H), 2.01 (s, 3H), 2.33-2.64 (m, 2H), 2.75-2.99 (m, 5H), 2.98-3.19 (m, 1H), 3.30-3.41 (m, 1H), 3.40-3.52 (m, 1H), 3.52-3.75 (m, 2H), 3.79-4.14 (m, 1H), 4.52 (d, J=12.50 Hz, 1H), 4.72-4.86 (m, 1H), 4.87-5.06 (m, 1H). MS (M + 1): 446.3. |
| 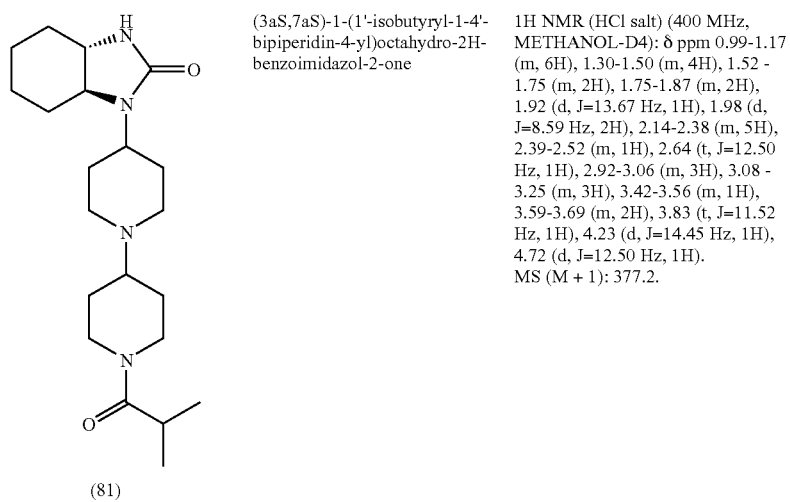 (81) | (3aS,7aS)-1-(1'-isobutyryl-1-4'-bipiperidin-4-yl)octahydro-2H-benzoimidazol-2-one | 1H NMR (HCl salt) (400 MHz, METHANOL-D4): δ ppm 0.99-1.17 (m, 6H), 1.30-1.50 (m, 4H), 1.52-1.75 (m, 2H), 1.75-1.87 (m, 2H), 1.92 (d, J=13.67 Hz, 1H), 1.98 (d, J=8.59 Hz, 2H), 2.14-2.38 (m, 5H), 2.39-2.52 (m, 1H), 2.64 (t, J=12.50 Hz, 1H), 2.92-3.06 (m, 3H), 3.08-3.25 (m, 3H), 3.42-3.56 (m, 1H), 3.59-3.69 (m, 2H), 3.83 (t, J=11.52 Hz, 1H), 4.23 (d, J=14.45 Hz, 1H), 4.72 (d, J=12.50 Hz, 1H). MS (M + 1): 377.2. |

Example 82

Isopropyl 4-((3aS,7aS)-2-oxooctahydro-1H-benzo[d]imidazol-1-yl)-1,4'-bipiperidine-1'-carboxylate

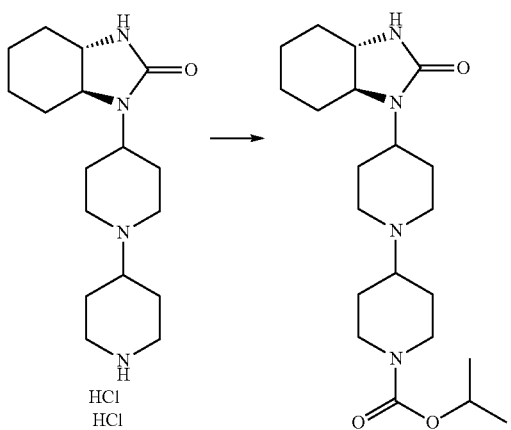

(3aS,7aS)-1-(1,4'-bipiperidin-4-yl)hexahydro-1H-benzo[d]imidazol-2(3H)-one dihydrochloride (0.68 g, 1.79 mmol) was dissolved in dichloromethane (20 mL) and triethylamine (0.75 mL, 5.38 mmol) was added. Isopropyl chloroformate (1.792 mL, 1.79 mmol) (solution 1M in toluene) was added drop wise at 0° C. The mixture was stirred for 2 hours then diluted in dichloromethane (60 mL) and the mixture made basic with 1N NaOH. The phases were separated and aq. phase was extracted with dichloromethane (2×25 mL). The combined organic phases were washed with brine (5 mL) and concentrated under reduced pressure. The crude was then purified by high pH prep LCMS to provide the title compound as a white solid (560 mg, 80%). 1H NMR (400 MHz, CHLOROFORM-D): δ ppm 1.22 (d, J=6.25 Hz, 6H), 1.26-1.49 (m, 6H), 1.58-1.70 (m, 2H), 1.72-1.84 (m, 7H), 1.94 (d, J=11.33 Hz, 1H), 2.14-2.32 (m, 3H), 2.33-2.47 (m, 1H), 2.69 (t, J=13.09 Hz, 2H), 2.84-2.96 (m, 2H), 2.96-3.06 (m, 1H), 3.65-3.81 (m, 1H), 4.07-4.28 (m, 2H), 4.43 (s, 1H), 4.80-4.94 (m, 1H). MS (M+1): 393.2

Example 83-86

The Examples in the Following Table was Prepared from (3aS,7aS)-1-(1,4'-bipiperidin-4-yl)octahydro-2H-benzimidazol-2-one or its Salt and With the Corresponding Chloroformate Following the Similar Method Described in Example 82

| Structure (Example) | Name | Data |
|---|---|---|
| (83) | prop-1-en-2-yl 4-((3aS,7aS)-2-oxooctahydro-1H-benzo[d]imidazol-1-yl)-1,4'-bipiperidine-1'-carboxylate | 1H NMR (400 MHz, CHLOROFORM-D): δ ppm 1.36 (d, J=10.55 Hz, 1H) 1.40-1.48 (m, 5H) 1.65-1.72 (m, 1H) 1.74-1.85 (m, 7H) 1.92-2.00 (m, 3H) 2.22-2.33 (m, 3H) 2.45 (ddd, J=11.23, 8.11, 3.32 Hz, 1H) 2.80 (s, 2H) 2.92-3.04 (m, 4H) 3.76 (ddd, J=16.60, 12.11, 4.10 Hz, 1H) 4.22 (s, 2H) 4.52 (s, 1H) 4.66 (d, J=5.47 Hz, 2H). (MS) (M + 1) = 391.2 |

| Structure (Example) | Name | Data |
|---|---|---|
| 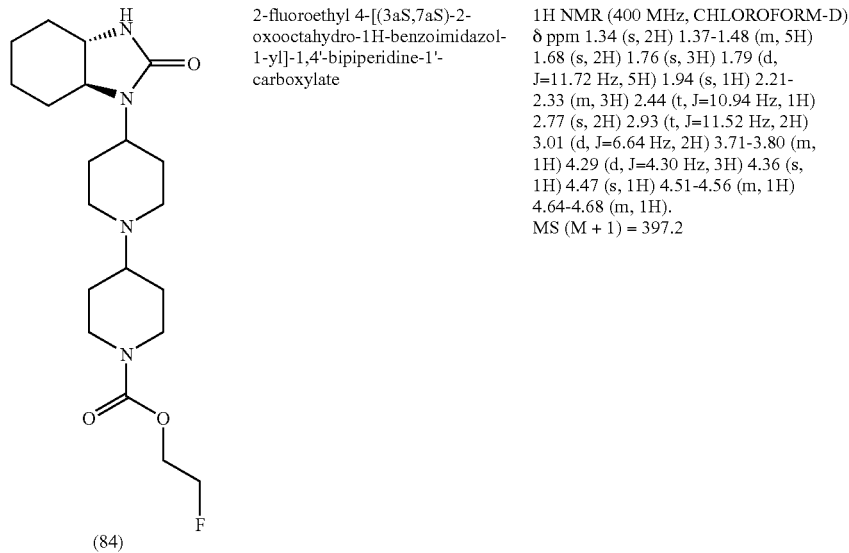<br>(84) | 2-fluoroethyl 4-[(3aS,7aS)-2-oxooctahydro-1H-benzoimidazol-1-yl]-1,4'-bipiperidine-1'-carboxylate | 1H NMR (400 MHz, CHLOROFORM-D) δ ppm 1.34 (s, 2H) 1.37-1.48 (m, 5H) 1.68 (s, 2H) 1.76 (s, 3H) 1.79 (d, J=11.72 Hz, 5H) 1.94 (s, 1H) 2.21-2.33 (m, 3H) 2.44 (t, J=10.94 Hz, 1H) 2.77 (s, 2H) 2.93 (t, J=11.52 Hz, 2H) 3.01 (d, J=6.64 Hz, 2H) 3.71-3.80 (m, 1H) 4.29 (d, J=4.30 Hz, 3H) 4.36 (s, 1H) 4.47 (s, 1H) 4.51-4.56 (m, 1H) 4.64-4.68 (m, 1H).<br>MS (M + 1) = 397.2 |
| 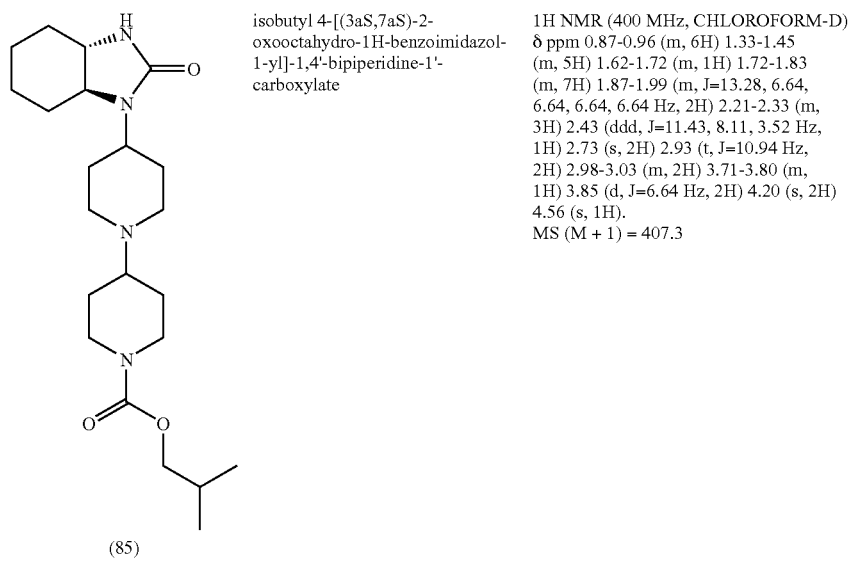<br>(85) | isobutyl 4-[(3aS,7aS)-2-oxooctahydro-1H-benzoimidazol-1-yl]-1,4'-bipiperidine-1'-carboxylate | 1H NMR (400 MHz, CHLOROFORM-D) δ ppm 0.87-0.96 (m, 6H) 1.33-1.45 (m, 5H) 1.62-1.72 (m, 1H) 1.72-1.83 (m, 7H) 1.87-1.99 (m, J=13.28, 6.64, 6.64, 6.64, 6.64 Hz, 2H) 2.21-2.33 (m, 3H) 2.43 (ddd, J=11.43, 8.11, 3.52 Hz, 1H) 2.73 (s, 2H) 2.93 (t, J=10.94 Hz, 2H) 2.98-3.03 (m, 2H) 3.71-3.80 (m, 1H) 3.85 (d, J=6.64 Hz, 2H) 4.20 (s, 2H) 4.56 (s, 1H).<br>MS (M + 1) = 407.3 |

| Structure (Example) | Name | Data |
|---|---|---|
| (86) | methyl 4-[(3aS,7aS)-2-oxooctahydro-1H-benzoimidazol-1-yl]-1,4'-bipiperidine-1'-carboxylate | 1H NMR (400 MHz, CHLOROFORM-D) δ ppm 1.09-1.51 (m, 6H), 1.55-1.84 (m, 8H), 1.92 (d, J=10.16 Hz, 1H), 2.09-2.31 (m, 3H), 2.37 (t, J=11.13 Hz, 1H), 2.58-2.78 (m, 2H), 2.87 (t, J=11.72 Hz, 2H), 2.92-3.05 (m, 2H), 3.62 (s, 3H), 3.53-3.77 (m, 1H), 3.96-4.31 (m, 2H), 4.97 (bs, 1H). MS (M + 1): 365.2. |

Example 87

Ethyl 4-[4-[(3aR,7aS)-2-oxo-3a,4,5,6,7,7a-hexahydro-3H-indol-1-yl]-1-piperidyl]piperidine-1-carboxylate

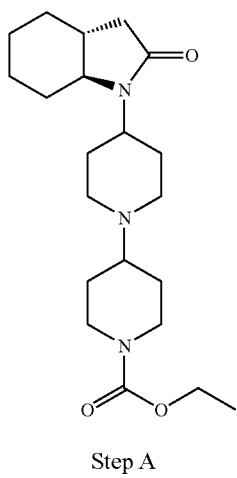

Step A

The preparation of {(1S,2S)-2-[(tert-butoxycarbonyl)amino]cyclohexyl}methyl methanesulfonate

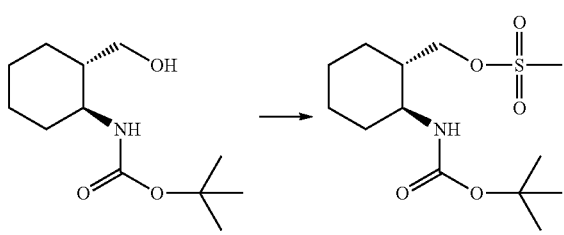

tert-butyl [(1S,2S)-2-(hydroxymethyl)cyclohexyl]carbamate (1.3 g, 5.68 mmol) was dissolved in dichloromethane (10 mL) and MsCl (0.52 mL, 6.75 mmol) was added dropwise at 0° C. Triethylamine (1 mL) was then added and the mixture stirred for 2 hours. The reaction mixture was quenched with ice and diluted in dichloromethane. Washed with a saturated solution of NaHCO₃ and brine, dried and concentrated in vacuo to provide the tile compound as brown solid (1.8 g). MS (M+1): 308.16

Step B

The preparation of tert-butyl [(1S,2R)-2-cyanomethyl)cyclohexyl]carbamate

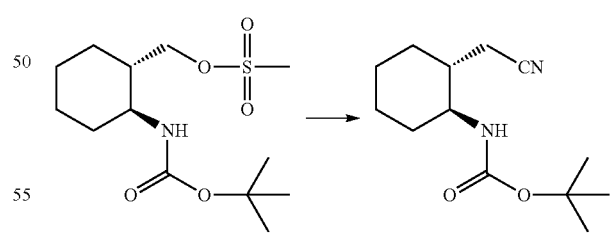

The crude of {(1S,2S)-2-[(tert-butoxycarbonyl)amino]cyclohexyl}methyl methanesulfonate (1.8 g) was dissolved in dry DMSO and potassium cyanide was added and the mixture was then heated at 90° C. under N₂ for 4 hours. The mixture was cooled and then poured on to water (50 mL) and extracted with ether (30 mL×3). The combined organic phases were washed with brine and concentrated in vacuo to provide the title compound.

Step C

The preparation of [(1R,2S)-2-aminocyclohexyl]acetonitrile

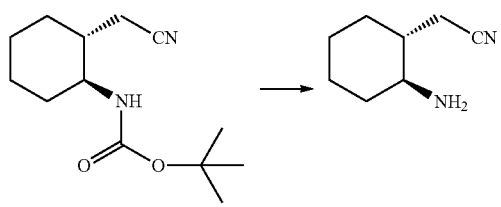

The crude of tert-butyl [(1S,2R)-2-cyanomethyl)cyclohexyl]carbamate was dissolved in dichloromethane (10 mL) and trifluoroacetic acid (2 mL) was added. The mixture stirred for 2 hours the concentrated in vacuo to provide the tile compound as a yellow oil. The mixture was then converted to freebase by MP carbonate work-up (1.1 g).

Step D

The preparation of tert-butyl 4-{[(1S,2R)-2-(cyanomethyl)cyclohexyl]amino}piperidine-1-carboxylate

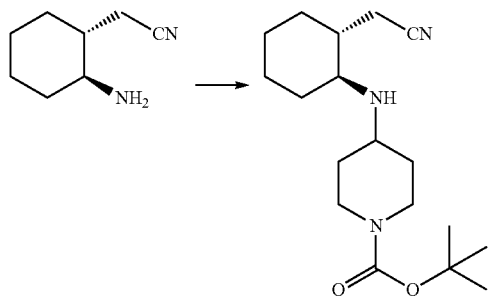

[(1R,2S)-2-aminocyclohexyl]acetonitrile (1.1 g) was dissolved in MeOH (10 mL) and sodium methoxyde (0.45 mL) was added. The mixture was stirred for 15 minutes then tert-butyl 4-oxopiperidine-1-carboxylate (0.85 g, 4.27 mmol) was added. A solution containing sodium cyanoborohydride (0.36 g, 5.22 mmol) and zinc chloride (0.35 g, 2.60 mmol) in MeOH (2 mL) was then added drop wise and the mixture stirred at room temperature. The solvent was then removed under reduced pressure and the residue was diluted in dichloromethane and was washed with 1N NaOH and brine. The crude was purified by high pH prep LCMS to provide 0.6 g of the title compound. MS (M+1): 322.27

Step E

The preparation of ((1R,2S)-2-{[1-(tert-butoxycarbonyl)piperidin-4-yl]amino}cyclohexyl)acetic acid

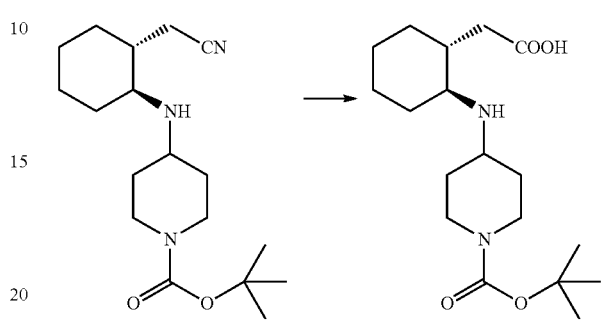

Tert-butyl 4-{[(1S,2R)-2-(cyanomethyl)cyclohexyl]amino}piperidine-1-carboxylate (90 mg, 0.28 mmol) was dissolved in ethanol (1 mL) and 1N NaOH was then added and was heated at 80 C for 3 hours. More 1N NaOH (1 mL) was added and the mixture stirred at room temperature over night. The mixture was concentrated in vacuo and dissolved in water (1 mL). Acidified to pH 3-4 with 2NHCl and the mixture was then concentrated in vacuo. Methanol was added, the precipitate filtered off and the filtrate was concentrated in vacuo to provide the title compound. MS (M+1): 341.3

Step F

The preparation of tert-butyl 4-[(3aR,7aS)-2-oxooctahydro-1H-indol-1-yl]piperidine-1-carboxylate

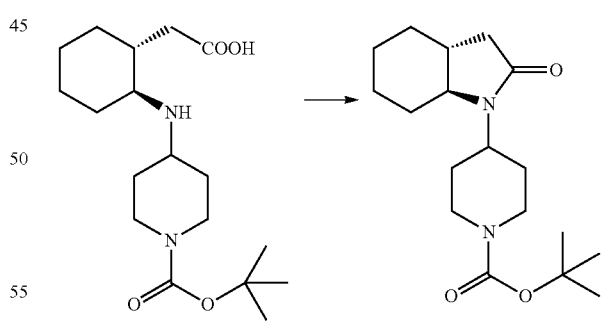

((1R,2S)-2-{[1-(tert-butoxycarbonyl)piperidin-4-yl]amino}cyclohexyl)acetic acid was dissolved in DMF (3 mL) and diisopropyl ethylamine (50 μL) and HATU (0.1 g, 0.26 mmol) was then added and the mixture stirred at room temperature over night. The solvent was then removed under reduced pressure and the mixture was diluted in dichloromethane. Washed with 1N NaOH and with brine and the solvent was then removed under reduced pressure to give the tile compound. MS (M+1): 323.24

147

Step G

The preparation of (3aR,7aS)-1-piperidin-4-yloctahydro-2H-indol-2-one

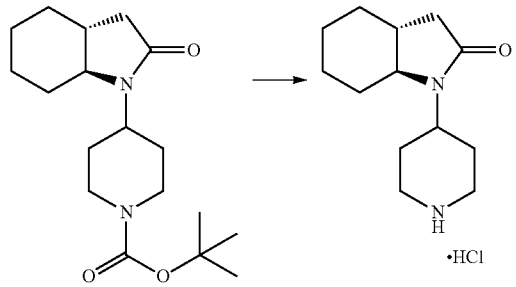

tert-butyl 4-[(3aR,7aS)-2-oxooctahydro-1H-indol-1-yl]piperidine-1-carboxylate was dissolved in MeOH (25 mL) and 4M HCl/dioxane (5 mL) was added. The mixture stirred at room temperature then concentrated in vacuo to give the tile compound. MS (M+1): 223.26

Step H

The preparation of ethyl 4-[(3aR,7aS)-2-oxooctahydro-1H-indol-1-yl]-1,4'-bipiperidine-1'-carboxylate

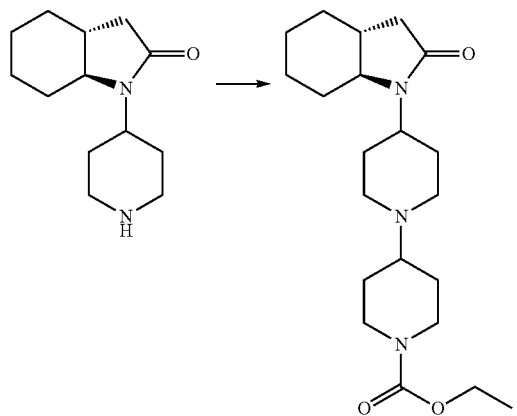

The crude of (3aR)-1-piperidin-4-yloctahydro-2H-indol-2-one (110 mg) was dissolved in MeOH (3 mL) and sodium methoxide (25 µL) was added followed by ethyl 4-oxopiperidine-1-carboxylate (77 µL, 0.5 mmol. A solution of sodium cyanoborohydride (35 mg, 0.5 mmol) and zinc chloride (29 mg, 0.25 mmol) in MeOH (1 mL) was added drop wise at room temperature and the mixture was stirred at room temperature over night. The solvent was then removed under reduced pressure and the residue dissolved in dichloromethane (60 mL). Washed with 1N NaOH (5 mL) and brine, dried and concentrated in vacuo. The residue was purified by high pH Prep LCMS to provide the title compound. 1H NMR (400 MHz, METHANOL-D4): δ ppm 1.24 (t, J=6.45 Hz, 3H), 1.27-1.49 (m, 6H), 1.62 (d, J=12.50 Hz, 2H), 1.55-1.73 (m, 1H), 1.78 (d, J=9.77 Hz, 1H), 1.82-2.17 (m, 7H), 2.18-2.33 (m, 3H), 2.33-2.43 (m, 1H), 2.49 (t, J=12.11 Hz, 1H), 2.69-2.86 (m, 2H), 3.02 (t, J=10.94 Hz, 2H), 3.12 (t, J=10.16 Hz, 1H), 3.72-3.85 (m, 1H), 4.09 (q, J=7.03 Hz, 2H), 4.16 (d, J=12.89 Hz, 2H). MS (M+1): 378.3

Example 88

Isopropyl 4-[(3aR,7aS)-2-oxooctahydro-1H-indol-1-yl]-1,4'-bipiperidine-1'-carboxylate

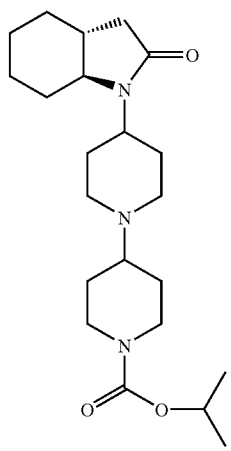

Step A

The preparation of tert-butyl 4-[(3aR,7aS)-2-oxooctahydro-1H-indol-1-yl]-1,4'-bipiperidine-1'-carboxylate

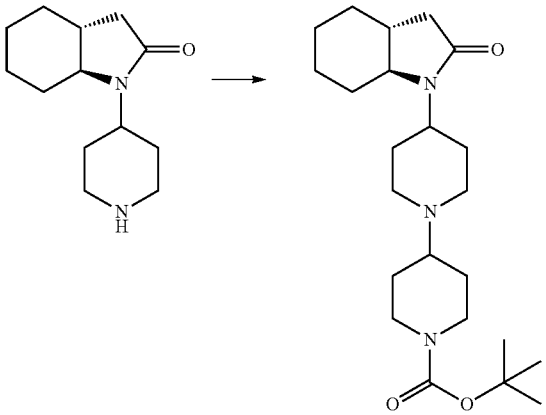

tert-butyl 4-[(3aR,7aS)-2-oxooctahydro-1H-indol-1-yl]-1,4'-bipiperidine-1'-carboxylate was prepared following similar reductive amination procedure described in Example 87, Step H

Step B

The preparation of (3aR,7aS)-1-(1,4'-bipiperidin-4-yl)octahydro-2H-indol-2-one

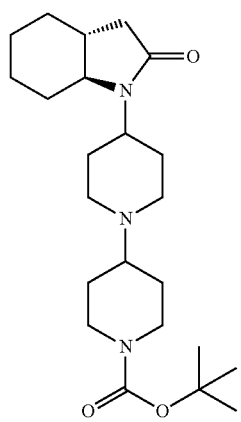

To a solution of tert-butyl 4-[(3aR,7aS)-2-oxooctahydro-1H-indol-1-yl]-1,4'-bipiperidine-1'-carboxylate (180 mg, 0.44 mmol) in MeOH (3 mL) was added 4M HCl (1 mL) and the mixture was stirred at room temperature. The solvents were then removed under reduced pressure to provide the title compound as yellow oil (120 mg). Ms (M+1): 306.3

Step C

The preparation of isopropyl 4-[(3aR,7aS)-2-oxooctahydro-1H-indol-1-yl]-1,4'-bipiperidine-1'-carboxylate

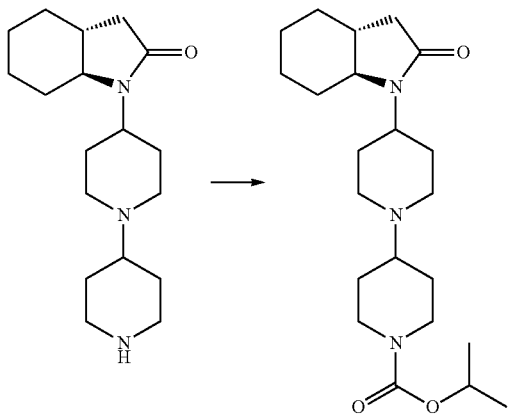

Following procedure similar to Example 82, the title compound was prepared from (3aR,7aS)-1-(1,4'-bipiperidin-4-yl)octahydro-2H-indol-2-one and isopropyl chloroformate. 1H NMR (400 MHz, METHANOL-D4) HCl salt: δ ppm 1.24 (d, J=5.86 Hz, 6H), 1.27-1.53 (m, 4H), 1.53-1.83 (m, 4H), 1.84-2.00 (m, 4H), 2.04-2.17 (m, 3H), 2.26 (d, J=6.64 Hz, 1H), 2.28-2.37 (m, 1H), 2.35-2.68 (m, 2H), 2.74-2.95 (m, 2H), 3.03-3.23 (m, 3H), 3.34-3.46 (m, 1H), 3.60 (d, J=12.89 Hz, 2H), 3.78-3.94 (m, 1H), 4.29 (d, J=14.06 Hz, 2H), 4.76-4.88 (m, 1H). MS (M+1): 392.3

Example 89

(3aR,7aS)-1-[1'-(2-methylbenzoyl)-1,4'-bipiperidin-4-yl]octahydro-2H-indol-2-one

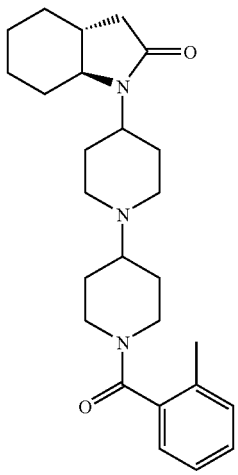

Step A

The preparation of 1-(2-methylbenzoyl)piperidin-4-one

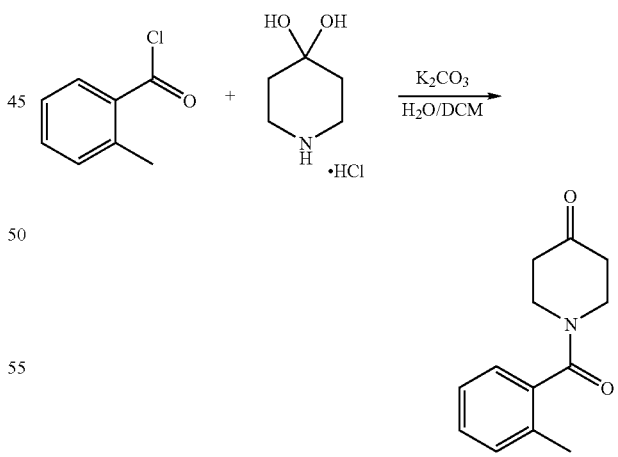

To a solution of 2-methylbenzoyl chloride (800 mg, 5.2 mmol) in 5 mL of DICHLOROMETHANE was added a mixture of piperidine-4,4-diol hydrochloride salt 800 mg, 5.2 mmol) and potassium carbonate (716 mg, 5.2 mmol) in 5 mL H₂O and stirred at room temperature for 2 hours. Layers were separated and aqueous layer was extracted with dichloromethane (3×10 mL). Organic layers were combined, dried, filtered and the filtrate was concentrated in vacuo to give the tile compound (1.2 g) as light yellow oil. MS (M+1): 218.0

Step B

The preparation of (3aR,7aS)-1-[1'-(2-methylbenzoyl)-1,4'-bipiperidin-4-yl]octahydro-2H-indol-2-one

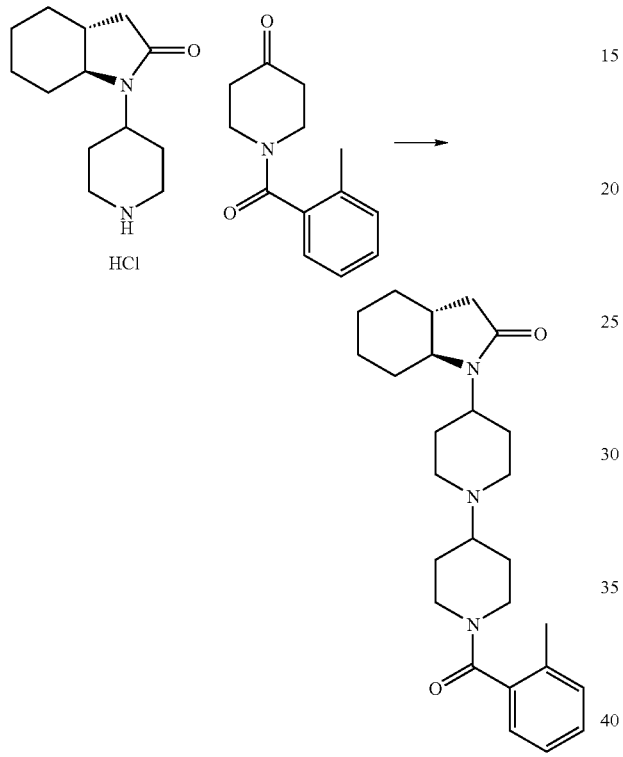

To a solution of (3aR,7aS)-1-piperidin-4-yloctahydro-2H-indol-2-one hydrochloride (70 mg, 0.27 mmol) in MeOH (4 mL) was added sodium methoxide (62 µl, 0.27 mmol) followed by 1-(2-methylbenzoyl)piperidin-4-one (60 mg, 0.27 mmol) and the mixture stirred at room temperature for 10 minutes. A solution containing sodium cyanoborohydride (28 mg, 0.41 mmol) and zinc chloride (18 mg, 0.13 mmol) in MeOH (1 mL) was then added and the mixture stirred at room temperature overnight. The reaction was quenched with water and solvents were removed under reduced pressure. The mixture was diluted in dichloromethane (30 mL) and 1N NaOH (7 mL) was added. The phases were separated and aqueous phase was extracted with dichloromethane (2×20 mL). The combined organic phases were dried and concentrated in vacuo. The crude compound was purified by high pH prep LCMS (40-60%) to provide the title compound as a white solid (37 mg, 37%). 1H NMR (400 MHz, CHLOROFORM-D): δ ppm 1.12-1.41 (m, 5H), 1.42-1.54 (m, 1H), 1.54-1.70 (m, 4H), 1.70-1.99 (m, 7H), 2.11-2.39 (m, 4H), 2.23 (s, 3H), 2.39-2.55 (m, 1H), 2.72 (t, J=12.50 Hz, 1H), 2.78-3.07 (m, 4H), 3.48 (d, J=12.11 Hz, 1H), 3.83-4.01 (m, 1H), 4.80 (d, J=12.50 Hz, 1H), 7.01-7.28 (m, 4H). MS (M+1): 424.2

Example 90 and 91

Ethyl (3S)-3-{4-[(3aR,7aS)-2-oxooctahydro-1H-indol-1-yl]piperidin-1-yl}pyrrolidine-1-carboxylate and ethyl (3R)-3-{4-[(3aR,7aS)-2-oxooctahydro-1H-indol-1-yl]piperidin-1-yl}pyrrolidine-1-carboxylate

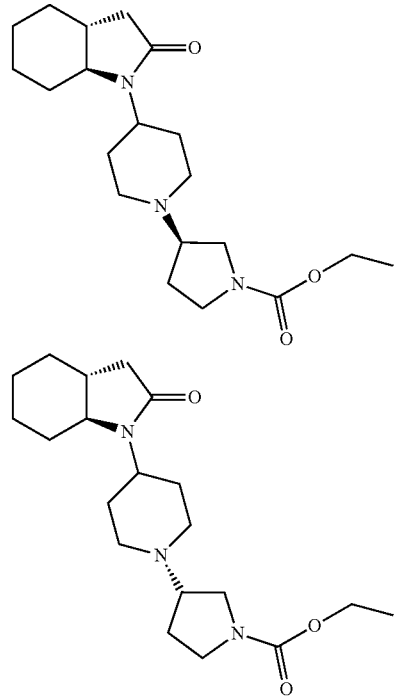

Step A

The Preparation of Mixture of Two Diastereomers

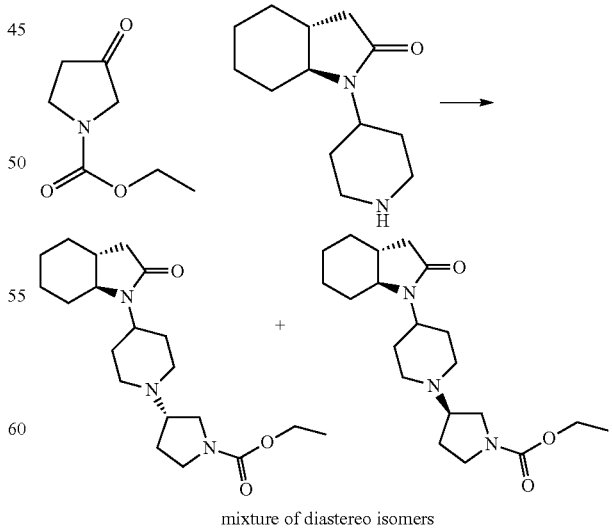

mixture of diastereo isomers (3aR,7aS)-1-(piperidin-4-yl)hexahydro-1H-indol-2(3H)-one (0.38 g, 1.44 mmol) was dissolved in MeOH (5 ml) and triethylamine (0.200 ml, 1.44 mmol) was added followed by 1-N-ethoxycarbonyl-3-pyrrolidinone (0.226 g, 1.44 mmol). After 15 minutes a solution of sodium cyanoborohydride (0.135 g, 2.15 mmol) and zinc chloride (0.098 g, 0.72 mmol) in methanol (1 ml) was added dropwise at room temperature. The mixture was stirred at room temperature over night. The solvent was then removed under reduced pressure and the residue was diluted in dichloromethane (60 mL) and washed with 1N NaOH (10 mL) followed by brine (5 mL) and concentrated under reduced pressure. The crude was then purified by using high pH prep LCMS to provide the mixture of two enantiomers (0.15 g). MS (M+1): 364.26

Step B

Separation of Diastereomers by Chiral HPLC

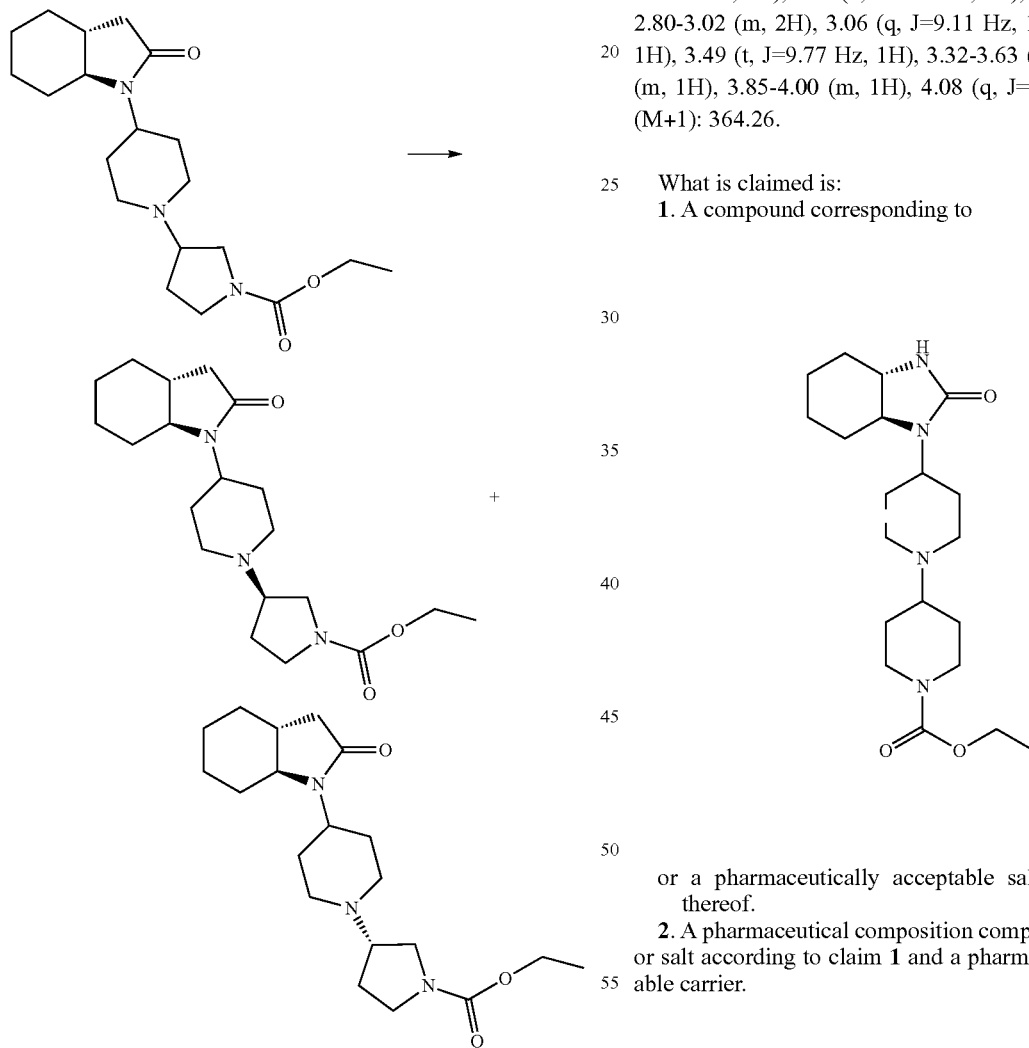

The mixture of two diastereo isomers was purified by chiral HPLC AD 30% isopropanol (ChiralPak AD, 21×250 mm, 20 μm particle size) to provide the pure diastereoisomers as Isomer 1 and Isomer 2 as a white solids.

Isomer 1: HPLC Retention time=8.75 min (40% isopropanol, ChiralPak AD, 4.6×250 mm, 20 μm particle size). 1H NMR (400 MHz, CHLOROFORM-D) δ ppm 1.07-1.45 (m, 3H), 1.22 (t, J=7.23 Hz, 3H), 1.50-2.17 (m, 13H), 2.30 (d, J=6.64 Hz, 1H), 2.33 (d, J=6.64 Hz, 1H), 2.62-2.88 (m, 2H), 2.92-3.12 (m, 3H), 3.18-3.35 (m, 1H), 3.50 (t, J=9.57 Hz, 1H), 3.53-3.64 (m, 1H), 3.64-3.73 (m, 1H), 3.87-4.02 (m, 1H), 4.09 (q, J=7.03 Hz, 2H). Ms (M+1): 364.26.

Isomer 2: HPLC Retention time=15.53 min (40% isopropanol, ChiralPak AD, 4.6×250 mm, 20 μm particle size. 1H NMR (400 MHz, CHLOROFORM-D): δ ppm 1.12-1.46 (m, 3H), 1.21 (t, J=7.23 Hz, 3H), 1.49-2.15 (m, 13H), 2.29 (d, J=6.64 Hz, 1H), 2.33 (d, J=6.25 Hz, 1H), 2.63-2.81 (m, 2H), 2.80-3.02 (m, 2H), 3.06 (q, J=9.11 Hz, 1H), 3.19-3.37 (m, 1H), 3.49 (t, J=9.77 Hz, 1H), 3.32-3.63 (m, 1H), 3.64-3.72 (m, 1H), 3.85-4.00 (m, 1H), 4.08 (q, J=7.03 Hz, 2H). MS (M+1): 364.26.

What is claimed is:

1. A compound corresponding to

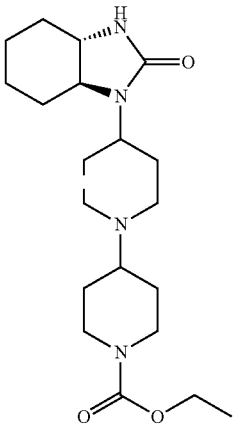

or a pharmaceutically acceptable salt or stereoisomer thereof.

2. A pharmaceutical composition comprising a compound or salt according to claim 1 and a pharmaceutically acceptable carrier.

* * * * *